(12) United States Patent
Davis et al.

(10) Patent No.: US 6,943,000 B2
(45) Date of Patent: Sep. 13, 2005

(54) JNK3 MODULATORS AND METHODS OF USE

(75) Inventors: Roger J. Davis, Princeton, MA (US); Richard A. Flavell, Guilford, CT (US); Pasko Rakic, New Haven, CT (US); Alan J. Whitmarsh, Shrewsbury, MA (US); Chia-Yi Kuan, Wallingford, CT (US); Derek Di Yang, Carmel, IN (US)

(73) Assignees: University of Massachusetts, Boston, MA (US); Yale University, New Haven, CT (US)

(*) Notice: Subject to any disclaimer, the term of this patent is extended or adjusted under 35 U.S.C. 154(b) by 0 days.

(21) Appl. No.: 09/165,522

(22) Filed: Oct. 2, 1998

(65) Prior Publication Data

US 2003/0023990 A1 Jan. 30, 2003

Related U.S. Application Data

(60) Provisional application No. 60/060,995, filed on Oct. 3, 1997.

(51) Int. Cl.[7] .............................. C12N 9/00; C12N 9/12; C12P 21/06; C12Q 1/48; C07H 21/04
(52) U.S. Cl. ................................ 435/194; 435/4; 435/6; 435/15; 435/69.1; 435/183; 435/193; 536/23.2; 536/23.4; 536/23.5
(58) Field of Search ........................ 435/4, 6, 7.1, 7.2, 435/15, 320.1, 325, 463, 40.51, 7.21; 514/14, 44; 536/23.2–23.7

(56) References Cited

U.S. PATENT DOCUMENTS

| | | |
|---|---|---|
| 5,534,426 A | 7/1996 | Karin et al. |
| 5,593,884 A | 1/1997 | Karin et al. |
| 5,605,808 A | 2/1997 | Karin et al. |
| 5,736,381 A | 4/1998 | Davis et al. ............. 435/252.3 |
| 5,804,399 A | 9/1998 | Karin et al. |
| 5,837,244 A | 11/1998 | Karin et al. |
| 5,877,309 A * | 3/1999 | McKay et al. ............. 536/24.5 |
| 5,994,513 A | 11/1999 | Karin et al. |
| 6,001,584 A | 12/1999 | Karin et al. |
| 6,043,083 A | 3/2000 | Davis et al. ................ 435/325 |
| 6,193,965 B1 | 2/2001 | Karin et al. |
| 6,465,618 B1 | 10/2002 | Nishida et al. ............. 530/350 |

FOREIGN PATENT DOCUMENTS

| | | |
|---|---|---|
| WO | WO 95/03323 | 2/1995 |
| WO | WO 95/03324 | 2/1995 |

OTHER PUBLICATIONS

Martin et al. Molecular Brain Res., 1996, vol. 35:47–57.*
Kuan et al., PNAS, 2003, vol. 100(25):15184–15189.*
Schwarzschild et al. J. Neuroscience, May 1997, vol. 17(10):3455–3466.*
Meldrum B, Brain Research Reviews, 1993, vol. 18:293–314.*
Sawyer et al. Molecular Biology and Biotechnology, A comprehensive Desk reference, Ed. Robert A. Myers, 1995, Wiley–VCH, USA pp. 38–45.*
Uhlmann et al. Molecular Biology and Biotechnology, A comprehensive Desk reference, Ed. Robert A. Myers, 1995, Wiley–VCH, USA pp. 648–653.*
Chauhan D et al. Interleukin–6 inhibits Fas–induced apoptosis and stress–activated protein kinase activation in multiple myeloma cells. Blood, Jan. 1, 1997, vol. 89:227–234, 1997*
Dickens et al., "A Cytoplasmic Inhibitor of the JNK Signal Transduction Pathway", Science, vol. 277, pp. 693–696 (1997).
Woodgett et al., "The Stress Activated Protein Kinase Pathway" *Cancer Surveys* 27:127–138 (1996).
Zhang et al., "A splicing variant of a death domain protein that is regulated by a mitogen–activated kinase is a substrate for c–Jun N–terminal kinase in the human central nervous system" *Proc. Natl. Acad. Sci. USA* 95:2586–2591 (1998).
Yang et al., "Absence of excitotoxicity–induced apoptosis in the hippocampus of mice lacking the Jnk3gene" *Nature* 389:865–870 (1997).
Batistatou et al., "Internucleosomal DNA Cleavage and Neuronal Cell Survival/Death" J. of Cell. Biol. 122(3):523–532, 1993.
Carboni et al., "Localization of the Messenger RNA for the c–Jun $NH_2$–Terminal Kinase Kinase in the . . . " Neuroscience 80(1):147–160, 1997.
Davis, R., "MAPKs: new JNK expands the group" TIBS 19:470–473, 1994.
Derijard et al., "JNK1: A Protein Kinase Stimulated by UV Light and Ha–Ras that Binds and Phosphorylates . . . " Cell 76:1025–1037, 1994.
Estus et al., "Altered Gene Expression in Neurons during Programmed Cell Death: Identification of c–jun . . . " J. of Cell Biol. 127(6–1):1717–1727, 1994.
Gomez et al., "JNK (c–jun $NH_2$–terminal Kinase) Is a Target for Antioxidants in T Lymphocytes" J. of Biol. Chem. 271(42):26335–26340, 1996.
Gupta et al., "Transcription Factor ATF2 Regulation by the JNK Signal Transduction Pathway" Science 267:389–393, 1995.

(Continued)

*Primary Examiner*—Manjunath N. Rao
(74) *Attorney, Agent, or Firm*—Fish & Richardson P.C.

(57) ABSTRACT

The c–Jun $NH_2$–terminal kinase (JNK) group of MAP kinases are activated by exposure of cells to environmental stress. The role of JNK in the brain was examined by targeted disruption of the gene that encodes the neuronal isoform JNK3. It was found that JNK3 is required for the normal response to seizure activity. Methods of screening for molecules and compounds that decrease JNK3 expression or activity are described. Such molecules or compounds are useful for treating disorders involving excitotoxicity such as seizure disorders, Alzheimer's disease, Huntington disease, Parkinson's disease, and ischaemia.

14 Claims, 24 Drawing Sheets

OTHER PUBLICATIONS

Gupta et al., "Selective interaction of JNK protein kinase isoforms with transcription factors" The EMBO Journal 15(11):2760–2770, 1996.

Ham et al., "A c–jun Dominant Negative Mutant Protects Sympathetic Neurons against Programmed Cell Death" Neuron 14:927–939, 1995.

Hitberg et al., "c–Jun is essential for normal mouse development and hepatogenesis " Nature 365:179–181, 1993.

Kuida et al., "Decreased apoptosis in the brain and premature letality in CPP32–deficient mice" Nature 384:368–372, 1996.

Kyriakis et al., "The stress–activated protein kinase subfamily of c–Jun kinases" Nature 369:156–160, 1994.

Lander et al., "Differential Activation of Mitogen–activated Protein Kinases by Nitric Oxide–related Species" J. of Biol. Chem. 271(33):19705–19709, 1996.

Lo, et al., "Reactive Oxygen Species Mediate Cytokine Activation of c–Jun $NH_2$–terminal Kinases" J. of Biol. Chem. 271(26):15703–15707, 1996.

Martin et al., "Developmental expression in the mouse nervous system of the $p49^{3F12}$ SAP kinase" Molecular Brain Res. 35:47–57, 1996.

Martin et al., "Inhibitors of Protein Synthesis and RNA Synthesis Prevent Neuronal Death Caused by Nerve Growth . . . " J. of Cell Biol. 106:829–844, 1988.

Mohit et al., "$p49^{3F12}$ Kinase: A Novel MAP Kinase Exposed in a Subset of Neurons in the Human Nervous System" Neuron 14:67–78, 1995.

Nadler et al., "Kainic Acid Neurotoxicity Toward Hippocampal Formation: Dependence on Specific Excitatory Pathways" Brain Res. 195:47–56, 1980.

Nishina et al., "Stress–signalling kinase Sek1 protects thymocytes from apoptosis mediated by CD95 and CD3" Nature 385:350–353, 1997.

Neumann–Haefelin et al., "Differential Expression of the Immediate Early Genes c–fos, c–jun, junB, and . . . " J. of Cerebral Blood Flow and Metabolism 14:206–216, 1994.

Oppenheim et al., "Naturally Occurring and Induced Neuronal Death in Chick Embryo in Vivo Requires Protein and RNA . . . " Developmental Biol. 138:104–113, 1990.

Raff et al., "Programmed Cell Death and the Control of Cell Survival: Lessons from the Nervous System" Science 262:695–700, 1993.

Ratan et al., "Oxidative Stress Induces Apoptosis in Embryonic Cortical Neurons" J. of Neurochemistry 62(1):376–379, 1994.

Sanchez et al., "Role of SAPK/ERK kinase–1 in the stress–activated pathway regulating transcription factor c–Jun" Nature 372(6508):794–798, 1994.

Thompson, C., "Apoptosis in the Pathogenesis and Treatment of Disease" Science 267:1456–1462, 1995.

Whitmarsh et al., "Transcription factor AP–1 regulation by mitogen–activated protein kinase signal transduction pathways" J. Mol. Med. 74:589–607, 1996.

Xia et al., "Opposing Effects of ERK and JNK–p38 MAP Kinases on Apoptosis" Science 270:1326–1331, 1995.

Yang et al., "Targeted disruption of the MKK4 gene causes embryonic death, inhibition of c–Jun . . . " Proc. Nat'l. Acad. Sci. USA 94:3004–3009, 1997.

* cited by examiner

FIG. 1A ttatgcaaga aactgttgaa ttagacccgt ttcctataga tgagaaacca tacaagctgt
ggtatttatg agcctccatt tcttatacta ctgcagtgaa ccaacattgg atgtgaaaat
tgccttttgt cagggattcg ataaacaagt ggatgtgtca tatattgcca aacattacaa
catgagcaaa agcaaagttg acaaccagtt ctacagtgtg gaagtgggag actcaacctt
cacagttctc aagcgctacc agaatctaaa gcctattggc tctggggctc agggcatagt
ttgtgccgcg tatgatgctg tccttgacag aaatgtggcc attaagaagc tcagcagacc
ctttcagaac caaacacatg ccaagagagc gtaccgggag ctggtcctca tgaagtgtgt
gaaccataaa aacattatta gtttattaaa tgtcttcaca ccccagaaaa cgctggagga
gttccaagat gtttacttag taatggaact gatggatgcc aacttatgtc aagtgattca
gatggaatta gaccatgagc gaatgtctta cctgctgtac caaatgttgt gtggcattaa
gcacctccat tctgctggaa ttattcacag ggatttaaaa ccaagtaaca ttgtagtcaa
gtctgattgc acattgaaaa tcctggactt tggactggcc aggacagcag gcacaagctt
catgatgact ccatatgtgg tgacacgtta ttacagagcc cctgaggtca tcctggggat
gggctacaag gagaacgtgg atatatggtc tgtgggatgc attatgggag aaatggttcg
ccacaaaatc ctctttccag gaagggacta tattgaccag tggaataagg taattgaaca
actaggaaca ccatgtccag aattcatgaa gaaattgcaa cccacagtaa gaaactatgt
ggagaatcgg cccaagtatg cgggactcac cttccccaaa ctcttcccag attccctctt
cccagcggac tccgagcaca ataaactcaa agccagccaa gccagggact tgttgtcaaa
gatgctagtg attgacccag caaaaagaat atcagtggac gacgccttac agcatcccta
catcaacgtc tggtatgacc cagccgaagt ggaggcgcct ccacctcaga tatatgacaa
gcagttggat gaaagagaac acacaattga agaatggaaa gaacttatct acaaggaagt
aatgaattca gaagaaaaga ctaaaaatgg tgtagtaaaa ggacagcctt ctccttcagg
tgcagcagtg aacagcagtg agagtctccc tccatcctcg tctgtcaatg acatctcctc
catgtccacc gaccagaccc tggcatctga cactgacagc agcctggaag cctcggcagg
accctgggt tgttgcaggt gactagccgc ctgcctgcga aacccagcgt tcttcaggag
atgat (SEQ ID NO: 1)

FIG. 1B

MSLHFLYYCSEPTLDVKIAFCQGFDKQVDVSYIAKHYNMSKSKVDNQFYSVEVGDSTFTVL
KRYQNLKPIGSGAQGIVCAAYDAVLDRNVAIKKLSRPFQNQTHAKRAYRELVLMKCVNHKN
IISLLNVFTPQKTLEEFQDVYLVMELMDANLCQVIQMELDHERMSYLLYQMLCGIKHLHSA
GIIHRDLKPSNIVVKSDCTLKILDFGLARTAGTSFMMTPYVVTRYYRAPEVILGMGYKENV
DIWSVGCIMGEMVRHKILFPGRDYIDQWNKVIEQLGTPCPEFMKKLQPTVRNYVENRPKYA
GLTFPKLFPDSLFPADSEHNKLKASQARDLLSKMLVIDPAKRISVDDALQHPYINVWYDPA
EVEAPPPQIYDKQLDEREHTIEEWKELIYKEVMNSEEKTKNGVVKGQPSPSGAAVNSSESL
PPSSSVNDISSMSTDQTLASDTDSSLEASAGPLGCCR (SEQ ID NO: 2)

FIG. 1C

```
GAGAAATGGCGTGGCAGGGGACCCAGCGAGCCCAGAGGGATTTTGCCGCTGCTTCCTCTAC
CCCTGTATTTCACGCAGCTCTCTAAATTGACTCAGCTCCAGGCTAGTGTGAGAAACACCAA
CAGCAGGCCCATCTCAGATCTTCACTATGGCAACTTATGCAAGAAACTGTTGAATTAGACC
CGTTTCCTATAGATGAGAAACCATACAAGCTGTGGTATTTATGAGCCTCCATTTCTTATAC
TACTGCAGTGAACCAACATTGGATGTGAAAATTGCCTTTTGTCAGGGATTCGATAAACAAG
TGGATGTGTCATATATTGCCAAACATTACAACATGAGCAAAAGCAAAGTTGACAACCAGTT
CTACAGTGTGGAAGTGGGAGACTCAACCTTCACAGTTCTCAAGCGCTACCAGAATCTAAAG
CCTATTGGCTCTGGGGCTCAGGGCATAGTTTGTGCCGCGTATGATGCTGTCCTTGACAGAA
ATGTGGCCATTAAGAAGCTCAGCAGACCCTTTCAGAACCAAACACATGCCAAGAGAGCGTA
CCGGGAGCTGGTCCTCATGAAGTGTGTGAACCATAAAAACATTATTAGTTTATTAAATGTC
TTCACACCCCAGAAAACGCTGGAGGAGTTCCAAGATGTTTACTTAGTAATGGAACTGATGG
ATGCCAACTTATGTCAAGTGATTCAGATGGAATTAGACCCATGAGCGAATGTCTTACCTGCT
GTACCAAATGTTGTGTGGCATTAAGCACCTCCATTCTGCTGGAATTATTCACAGGGATTTA
AAACCAAGTAACATTGTAGTCAAGTCTGATTGCACATTGAAAATCCTGGACTTTGGACTGG
CCAGGACAGCAGGCACAAGCTTCATGATGACTCCATATGTGGTGACACGTTATTACAGAGC
CCCTGAGGTCATCCTGGGGATGGGCTACAAGGAGAACGTGGATATATGGTCTGTGGGATGC
ATTATGGGAGAAATGGTTCGCCACAAAATCCTCTTTCCAGGAAGGGACTATATTGACCAGT
GGAATAAGGTAATTGAACAACTAGGAACACCATGTCCAGAATTCATGAAGAAATTGCAACC
CACAGTAAGAAACTATGTGGAGAATCGGCCCAAGTATGCGGGACTCACCTTCCCCAAACTC
TTCCCAGATTCCCTCTTCCCAGCGGACTCCGAGCACAATAAACTCAAAGCCAGCCAAGCCA
GGGACTTGTTGTCAAAGATGCTAGTGATTGACCCAGCAAAAAGAATATCAGTGGACGACGC
CTTACAGCATCCCTACATCAACGTCTGGTATGACCCAGCCGAAGTGGAGGCGCCTCCACCT
CAGATATATGACAAGCAGTTGGATGAAAGAGAACACACAATTGAAGAATGGAAAGAACTTA
TCTACAAGGAAGTAATGAATTCAGAAGAAAGACTAAAAATGGTGTAGTAAAAGGACAGCC
TTCTCCTTCAGGTGCAGCAGTGAACAGCAGTGAGAGTCTCCCTCCATCCTCGTCTGTCAAT
GACATCTCCTCCATGTCCACCGACCAGACCCTGGCATCTGACACTGACAGCAGCCTGGAAG
CCTCGGCAGGACCCCTGGGTTGTTGCAGGTGACTAGCCGCCTGCCTGCGAAACCCAGCGTT
CTTCAGGAGATGATGTGATGGAACACACACACACGCAGACACACACACACACACAAATGCA
GACACACAACATCAAGAAAACAGCAAGGGAGAGAATCCAAGCCTAAAATTAAATAAATCTT
TCAGCCTGCTTCTTCCCCAGGGTTCTGTATTGCAGCTAAGCTCAAATGTATATTTAACTTC
TAGTTGCTCTTGCTTTGGTCTTCTTCCAATGATGCTTACTACAGAAAGCAAATCAGACACA
ATTAGAGAAGCCTTTTCCATAAAGTGTAATTTTAATGGCTGCAAAACCGGCAACCTGTAAC
TGCCCTTTTAAATGGCATGACAAGGTGTGCAGTGGCCCCATCCAGCATGTGTGTCTCTA
TCTTGCATCTACCTGCTCCTTGGCCTAGTCAGATGGATGTAGATACAGATCCGCATGTGTC
TGTATTCATACAGCACTACTTACTTAGAGATGCTACTCTCAGTGTCCTCAGGGCTCTACCA
AGACATAATGCACTGGGGTACCACATGGTCCATTTCATGTGATCTATTACTCTGACATAAA
CCCATCTGTAATATATTGCCAGTATATAAGCTGTTTAGTTTGTTAATTGATTAAACTGTAT
GTCTTATAAGAAAACATGTAAAGGGGGAATATATTGGGGAGTGAGCTCTCTCAGACCCTT
GAAGATGTAGCTTCCAAATTTGAATGGATTAAATGGCACCTGTATACCA (SEQ ID NO:3)
```

FIG. 2A atctcagatc ttcactatgg caacttatgc aagaaactgt tgaattagac ccgtttccta
tagatgagaa accatacaag ctgtggtatt tatgagcctc catttcttatactactgcag
tgaaccaaca ttggatgtga aaattgcctt ttgtcaggga ttcgataaac aagtggatgt
gtcatatatt gccaaacatt acaacatgag caaaagcaaa gttgacaacc agttctacag
tgtggaagtg ggagactcaa ccttcacagt tctcaagcgc taccagaatc taaagcctat
tggctctggg gctcagggca tagtttgtgc cgcgtatgat gctgtccttg acagaaatgt
ggccattaag aagctcagca gacccttca gaaccaaaca catgccaaga gagcgtaccg
ggagctggtc ctcatgaagt gtgtgaacca taaaaacatt attagtttat taaatgtctt
cacacccag aaaacgctgg aggagttcca agatgtttac ttagtaatgg aactgatgga
tgccaactta tgtcaagtga ttcagatgga attagaccat gagcgaatgt cttacctgct
gtaccaaatg ttgtgtggca ttaagcacct ccattctgct ggaattattc acagggattt
aaaaccaagt aacattgtag tcaagtctga ttgcacattg aaaatcctgg actttggact
ggccaggaca gcaggcacaa gcttcatgat gactccatat gtggtgacac gttattacag
agcccctgag gtcatcctgg ggatgggcta caaggagaac gtggatatat ggtctgtggg
atgcattatg ggagaaatgg ttcgccacaa aatcctcttt ccaggaaggg actatattga
ccagtggaat aaggtaattg aacaactagg aacaccatgt ccagaattca tgaagaaatt
gcaacccaca gtaagaaact atgtggagaa tcggcccaag tatgcgggac tcaccttccc
caaactcttc ccagattccc tcttcccagc ggactccgag cacaataaac tcaaagccag
ccaagccagg gacttgttgt caaagatgct agtgattgac ccagcaaaaa gaatatcagt
ggacgacgcc ttacagcatc cctacatcaa cgtctggtat gacccagccg aagtggaggc
gcctccacct cagatatatg acaagcagtt ggatgaaaga gaacacacaa ttgaagaatg
gaaagaactt atctacaagg aagtaatgaa ttcagaagaa aagactaaaa atggtgtagt
aaaaggacag ccttctcctt cagcacaggt gcagcagtga acagcagtga gagtctccct
ccatcctcgt ctgtcaatga catctcctcc atgtccaccg accagaccct ggcatctgac
actgacagca gcctggaagc ctcggcagga cccctgggtt gttgcaggtg actagccgcc
tgcctgcgaa acccagcgtt cttcaggaga tgatgtgatg gaacacacac acacgcagac
acacacacac acacaaatgc agacacacaa catcaagaaa acagcaaggg agagaatcca

FIG. 2B

```
agcctaaaat taaataaatc tttcagcctg cttcttcccc agggttctgt attgcagcta
agctcaaatg tatatttaac ttctagttgc tcttgctttg gtcttcttcc aatgatgctt
actacagaaa gcaaatcaga cacaattaga gaa.
```
(SEQ ID NO:4)

FIG. 2C

```
MSLHFLYYCSEPTLDVKIAFCQGFDKQVDVSYIAKHYNMSKSKVDNQFYSVEVGDSTFTVL
KRYQNLKPIGSGAQGIVCAAYDAVLDRNVAIKKLSRPFQNQTHAKRAYRELVLMKCVNHKN
IISLLNVFTPQKTLEEFQDVYLVMELMDANLCQVIQMELDHERMSYLLYQMLCGIKHLHSA
GIIHRDLKPSNIVVKSDCTLKILDFGLARTAGTSFMMTPYVVTRYYRAPEVILGMGYKENV
DIWSVGCIMGEMVRHKILFPGRDYIDQWNKVIEQLGTPCPEFMKKLQPTVRNYVENRPKYA
GLTFPKLFPDSLFPADSEHNKLKASQARDLLSKMLVIDPAKRISVDDALQHPYINVWYDPA
EVEAPPPQIYDKQLDEREHTIEEWKELIYKEVMNSEEKTKNGVVKGQPSPSAQVQQ (SEQ ID NO: 5)
```

FIG. 2D

```
GAGAAATGGCGTGGCAGGGGACCCAGCGAGCCCAGAGGGATTTTGCCGCTGCTTCCTCTAC
CCCTGTATTTCACGCAGCTCTCTAAATTGACTCAGCTCCAGGCTAGTGTGAGAAACACCAA
CAGCAGGCCCATCTCAGATCTTCACTATGGCAACTTATGCAAGAAACTGTTGAATTAGACC
CGTTTCCTATAGATGAGAAACCATACAAGCTGTGGTATTTATGAGCCTCCATTTCTTATAC
TACTGCAGTGAACCAACATTGGATGTGAAAATTGCCTTTTGTCAGGGATTCGATAAACAAG
TGGATGTGTCATATATTGCCAAACATTACAACATGAGCAAAAGCAAAGTTGACAACCAGTT
CTACAGTGTGGAAGTGGGAGACTCAACCTTCACAGTTCTCAAGCGCTACCAGAATCTAAAG
CCTATTGGCTCTGGGGCTCAGGGCATAGTTTGTGCCGCGTATGATGCTGTCCTTGACAGAA
ATGTGGCCATTAAGAAGCTCAGCAGACCCTTTCAGAACCAAACACATGCCAAGAGAGCGTA
CCGGGAGCTGGTCCTCATGAAGTGTGTGAACCATAAAAACATTATTAGTTTATTAAATGTC
TTCACACCCCAGAAAACGCTGGAGGAGTTCCAAGATGTTTACTTAGTAATGGAACTGATGG
ATGCCAACTTATGTCAAGTGATTCAGATGGAATTAGACCATGAGCGAATGTCTTACCTGCT
GTACCAAATGTTGTGTGGCATTAAGCACCTCCATTCTGCTGGAATTATTCACAGGGATTTA
AAACCAAGTAACATTGTAGTCAAGTCTGATTGCACATTGAAAATCCTGGACTTTGGACTGG
CCAGGACAGCAGGCACAAGCTTCATGATGACTCCATATGTGGTGACACGTTATTACAGAGC
CCCTGAGGTCATCCTGGGGATGGGCTACAAGGAGAACGTGGATATATGGTCTGTGGGATGC
ATTATGGGAGAAATGGTTCGCCACAAAATCCTCTTTCCAGGAAGGGACTATATTGACCAGT
GGAATAAGGTAATTGAACAACTAGGAACACCATGTCCAGAATTCATGAAGAAATTGCAACC
CACAGTAAGAAACTATGTGGAGAATCGGCCCAAGTATGCGGGACTCACCTTCCCCAAACTC
TTCCCAGATTCCCTCTTCCCAGCGGACTCCGAGCACAATAAACTCAAAGCCAGCCAAGCCA
GGGACTTGTTGTCAAAGATGCTAGTGATTGACCCAGCAAAAAGAATATCAGTGGACGACGC
CTTACAGCATCCCTACATCAACGTCTGGTATGACCCAGCCGAAGTGGAGGCGCCTCCACCT
CAGATATATGACAAGCAGTTGGATGAAAGAGAACACACAATTGAAGAATGGAAAGAACTTA
TCTACAAGGAAGTAATGAATTCAGAAGAAAGACTAAAAATGGTGTAGTAAAAGGACAGCC
TTCTCCTTCAGCACAGGTGCAGCAGTGAACAGCAGTGAGAGTCTCCCTCCATCCTCGTCTG
TCAATGACATCTCCTCCATGTCCACCGACCAGACCCTGGCATCTGACACTGACAGCAGCCT
GGAAGCCTCGGCAGGACCCCTGGGTTGTTGCAGGTGACTAGCCGCCTGCCTGCGAAACCCA
GCGTTCTTCAGGAGATGATGTGATGGAACACACACACACGCAGACACACACACACACACAA
ATGCAGACACACAACATCAAGAAAACAGCAAGGGAGAGAATCCAAGCCTAAAATTAAATAA
ATCTTTCAGCCTGCTTCTTCCCCAGGGTTCTGTATTGCAGCTAAGCTCAAATGTATATTTA
ACTTCTAGTTGCTCTTGCTTTGGTCTTCTTCCAATGATGCTTACTACAGAAAGCAAATCAG
ACACAATTAGAGAAGCCTTTTCCATAAAGTGTAATTTTAATGGCTGCAAAACCGGCAACCT
GTAACTGCCCTTTTAAATGGCATGACAAGGTGTGCAGTGGCCCCATCCAGCATGTGTGTGT
CTCTATCTTGCATCTACCTGCTCCTTGGCCTAGTCAGATGGATGTAGATACAGATCGCAT
GTGTCTGTATTCATACAGCACTACTTACTTAGAGATGCTACTCTCAGTGTCCTCAGGGCTC
TACCAAGACATAATGCACTGGGGTACCACATGGTCCATTTCATGTGATCTATTACTCTGAC
ATAAACCCATCTGTAATATATTGCCAGTATATAAGCTGTTTAGTTTGTTAATTGATTAAAC
TGTATGTCTTATAAGAAAACATGTAAAGGGGGAATATATTGGGGGAGTGAGCTCTCTCAGA
CCCTTGAAGATGTAGCTTCCAAATTTGAATGGATTAAATGGCACCTGTATACCA (SEQ ID NO: 6)
```

FIG. 3A gagaaatggc gtggcagggg acccagcgag cccagaggga ttttgccgct gcttcctcta
cccctgtatt tcacgcagct ctctaaattg actcagctcc aggctagtgt gagaaacacc
aacagcaggc ccatctcaga tcttcactat ggcaacttat gcaagaaact gttgaattag
acccgtttcc tatagatgag aaaccataca agctgtggta tttatgagcc tccatttctt
atactactgc agtgaaccaa cattggatgt gaaaattgcc ttttgtcagg gattcgataa
acaagtggat gtgtcatata ttgccaaaca ttacaacatg agcaaaagca aagttgacaa
ccagttctac agtgtggaag tgggagactc aaccttcaca gttctcaagc gctaccagaa
tctaaagcct attggctctg gggctcaggg catagtttgt gccgcgtatg atgctgtcct
tgacagaaat gtggccatta agaagctcag cagacccttt cagaaccaaa cacatgccaa
gagagcgtac cgggagctgg tcctcatgaa gtgtgtgaac cataaaaaca ttattagttt
attaaatgtc ttcacacccc agaaaacgct ggaggagttc caagatgttt acttagtaat
ggaactgatg gatgccaact tatgtcaagt gattcagatg gaattagacc atgagcgaat
gtcttacctg ctgtaccaaa tgttgtgtgg cattaagcac ctccattctg ctggaattat
tcacagggat ttaaaaccaa gtaacattgt agtcaagtct gattgcacat tgaaaatcct
ggactttgga ctggccagga cagcaggcac aagcttcatg atgactccat atgtggtgac
acgttattac agagcccctg aggtcatcct ggggatgggc tacaaggaga acgtggatat
atggtctgtg ggatgcatta tgggagaaat ggttcgccac aaaatcctct ttccaggaag
ggactatatt gaccagtgga ataaggtaat tgaacaacta ggaacaccat gtccagaatt
catgaagaaa ttgcaaccca cagtaagaaa ctatgtggag aatcggccca gtatgcggg
actcaccttc cccaaactct cccagattc cctcttccca gcggactccg agcacaataa
actcaaagcc agccaagcca gggacttgtt gtcaaagatg ctagtgattg acccagcaaa
aagaatatca gtggacgacg ccttacagca tccctacatc aacgtctggt atgacccagc
cgaagtggag gcgcctccac ctcagatata tgacaagcag ttggatgaaa gagaacacac
aattgaagaa tggaaagaac ttatctacaa ggaagtaatg aattcagaag aaaagactaa
aaatggtgta gtaaaaggac agccttctcc ttcagcacag gtgcagcagt gaacagcagt
gagagtctcc ctccatcctc gtctgtcaat gacatctcct ccatgtccac cgaccagacc

FIG. 3B

```
ctggcatctg acactgacag cagcctggaa gcctcggcag gacccctggg ttgttgcagg
tgactagccg cctgcctgcg aaacccagcg ttcttcagga gatgatgtga tggaacacac
acacacgcag acacacacac acacacaaat gcagacacac aacatcaaga aaacagcaag
ggagagaatc caagcctaaa attaaataaa tctttcagcc tgcttcttcc ccagggttct
gtattgcagc taagctcaaa tgtatattta acttctagtt gctcttgctt tggtcttctt
ccaatgatgc ttactacaga aagcaaatca gacacaatta gagaagcctt ttccataaag
tgtaatttta atggctgcaa aaccggcaac ctgtaactgc ccttttaaat ggcatgacaa
ggtgtgcagt ggccccatcc agcatgtgtg tgtctctatc ttgcatctac ctgctccttg
gcctagtcag atggatgtag atacagatcc gcatgtgtct gtattcatac agcactactt
acttagagat gctactctca gtgtcctcag ggctctacca agacataatg cactggggta
ccacatggtc catttcatgt gatctattac tctgacataa acccatctgt aatatattgc
cagtatataa gctgtttagt ttgttaattg attaaactgt atgtcttata agaaaacatg
taaaggggga atatattggg ggagtgagct ctctcagacc cttgaagatg tagcttccaa
atttgaatgg attaaatggc acctgtatac ca      (SEQ ID NO: 7)
```

FIG. 3C

MSLHFLYYCSEPTLDVKIAFCQGFDKQVDVSYIAKHYNMSKSKVDNQFYSVEVGDSTF
TVLKRYQNLKPIGSGAQGIVCAAYDAVLDRNVAIKKLSRPFQNQTHAKRAYRELVLMK
CVNHKNIISLLNVFTPQKTLEEFQDVYLVMELMDANLCQVIQMELDHERMSYLLYQML
CGIKHLHSAGIIHRDLKPSNIVVKSDCTLKILDFGLARTAGTSFMMTPYVVTRYYRAP
EVILGMGYKENVDIWSVGCIMGEMVRHKILFPGRDYIDQWNKVIEQLGTPCPEFMKKL
QPTVRNYVENRPKYAGLTFPKLFPDSLFPADSEHNKLKASQARDLLSKMLVIDPAKRI
SVDDALQHPYINVWYDPAEVEAPPPQIYDKQLDEREHTIEEWKELIYKEVMNSEEKTK
NGVVKGQPSPSAQVQQ (SEQ ID NO: 8)

FIG. 4A

```
CCCTCCTTATTCCGGTTTGGAATGTGGCTAATGAAAGCCCAGTAGGAGGATTTCTGGGGCA
AACAGGTGGACCAGGATCCTGGTTCTCAGGCACGGAATGGCTATTGTGAGAGCGCCACCAG
CAGGACCATCGCAGATCTTGGTTATGGCTGCTCACGCAAGAGGCTGTTGATGTAGACCCCC
TTTCCCGTAGATGAGAAATCACACGAGCAGTGGTATTTATGAGCCTCCATTTCTTATACTA
CTGCAGTGAACCAACCTTGGATGTGAAAATTGCCTTTTGTCAGGTGTGTGTTCCTTACAGG
TAAAACAAAGGGATTCGACAAACACGTGGATGTGTCTTCTGTTGTCAAACATTACAACATG
AGCAAAAGCAAGGTAGATAACCAGTTCTACAGTGTGGAAGTGGGAGACTCAACCTTCACAG
TTCTAAAGCGCTACCAGAACCTGAAGCCGATCGGCTCTGGGGCTCAGGGAATAGTTTGTGC
TGCGTATGACGCTGTCCTCGACAGAAATGTGGCCATTAAGAAGCTCAGCAGACCCTTCCAG
AACCAAACTCATGCCAAGAGGGCTTACCGGGAGCTGGTCCTCATGAAGTGTGTGAACCATA
AAAACATTATTAGCTTATTAAATGTCTTTACACCCCAGAAAACACTGGAGGAGTTCCAAGA
TGTTTACTTAGTGATGGAACTGATGGACGCCAACTTGTGTCAGGTGATTCAGATGGAGCTG
GACCACGAGCGGATGTCGTACTTGCTGTACCAGATGCTGTCGGCGATCAAACACCTCCACT
CCGCTGGGATCATCCACAGGGACTTAAAACCCAGTAACATCGTAGTCAAGTCTGATTGCAC
ACTGAAAATCCTGGACTTTGGACTGGCCAGGACAGCGGGCACAAGCTTCATGATGACTCCG
TATGTGGTGACGAGATATTACAGAGCCCCGAGGTCATCCTGGGCATGGGCTACAAGGAGA
ACGTGGACATATGGTCTGTGGGCTGCATCATGGGAGAAATGGTTCGTCACAAAATCCTCTT
TCCCGGAAGGGACTATATTGACCAGTGGAACAAAGTCATAGAGCAGCTAGGAACTCCGTGT
CCAGAATTCATGAAGAAATTGCAGCCCACCGTCAGAAACTACGTGGAGAACCGGCCCAAGT
ATGCAGGCCTCACCTTCCCCAAGCTCTTTCCAGATTCCCTCTTCCCAGCGGATTCCGAGCA
CAATAAACTTAAAGCCAGCCAAGCCAGGGACTTGTTGTCAAAGATGTTAGTGATTGACCCA
GCGAAGAGGATATCGGTGGATGACGCATTGCAGCATCCGTACATCAACGTTTGGTACGACC
CTGCTGAAGTGGAGGCGCCTCCGCCTCAGATATATGACAAGCAATTGGATGAAAGGGAGCA
CACCATCGAAGAATGGAAAGAACTCATCTACAAGGAAGTAATGAACTCAGAAGAGAAGACT
AAGAACGGCGTAGTCAAAGGCCAGCCCTCACCTTCAGGTGCAGCAGTGAACAGCAGTGAGA
GTCTCCCTCCATCCTCATCTGTCAACGACATCTCCTCCATGTCCACCGACCAGACCCTCGC
ATCCGACACTGACAGCAGCCTGGAAGCCTCGGCGGGACCGCTGGGTTGTTGCAGGTGACTA
GCCGCCTGCCTGCGAAACCCAGCGTTCTTCAGGAGATGACGCCATGATAGAACACAGCGCA
CATGCACACACACAGAGCTTGTACACACACACACACACACACACACACGCACGCACGCACG
CACGCAAGCACGCACGCACGCACAAATGCACTCACGCAATGTCAAGAAAAAAAAAGTAGC
GAGAGAGAGCGAGAGAGCCAACGTAAAACTAAGTTAAATCTTTCTGCGTGCTTCTCCAGAG
TTCTGTATCGCAGCTGAGCTGAAATGTATACTTAACTTCTAGTCGCGCTCGCTCGACTTTG
GTCTCCCTCCGGCAGTGCTTACT          (SEQ ID NO: 9)
```

FIG. 4B

MSKSKVDNQFYSVEVGDSTFTVLKRYQNLKPIGSGAQGIVCAAYDAVLDRNVAIKKLSRPF
QNQTHAKRAYRELVLMKCVNHKNIISLLNVFTPQKTLEEFQDVYLVMELMDANLCQVIQME
LDHERMSYLLYQMLSAIKHLHSAGIIHRDLKPSNIVVKSDCTLKILDFGLARTAGTSFMMT
PYVVTRYYRAPEVILGMGYKENVDIWSVGCIMGEMVRHKILFPGRDYIDQWNKVIEQLGTP
CPEFMKKLQPTVRNYVENRPKYAGLTFPKLFPDSLFPADSEHNKLKASQARDLLSKMLVID
PAKRISVDDALQHPYINVWYDPAEVEAPPPQIYDKQLDEREHTIEEWKELIYKEVMNSEEK
TKNGVVKGQPSPSGAAVNSSESLPPSSSVNDISSMSTDQTLASDTDSSLEASAGPLGCCR (SEQ ID NO:10)

FIG. 5A

GGGGCTTGAGTGAGCTAAAGATTGGGTCTTCTTGGAAATCACCTGTCTGTTATTATTTTA
AACAATCGCTACACCTCCAAAGACTCTGCTCCTTACTCCGGTTTGGAATGTGGCTAATGAC
TACCCAGTAGGGAGGATTTCTGGGGCAAACAGCCGGACCAGGATCCTAGTTCTCAGGCACG
GAATGGCTATTGTGAGAACAGCACCAGCAGGATCATCGCAGATCTTGGTTATGGCCACTCA
GGCAAGACGCTGTTGAGTTAAGACCCCTTTCCCATAGATGAGAAGCCACAGAAGCAGTGGT
ATTTATGAGCCTCCATTTCTTATACTACTGCAGTGAACCAACCTTGGATGTGAAAATTGCC
TTTTGTCAGGGATTCGATAAACACGTGGATGTGTCATCTATTGCCAAACATTACAACATGA
GCAAAAGCAAGGTGGACAACCAGTTCTACAGTGTGGAAGTGGGGACTCAACCTTCACCGT
TCTTAAGCGCTACCAGAACCTGAAGCCAATTGGCTCTGGGGCTCAGGGAATAGTCTGTGCT
GCGTACGACGCTGTCCTTGACAGAAATGTGGCCATTAAGAAGCTCAGCAGACCCTTCCAGA
ACCAAACTCACGCCAAGAGGGCTTACCGGGAGCTGGTGCTCATGAAGTGTGTGAACCATAA
AAACATTATTAGCTTATTAAATGTTTTACACCCCAGAAAACGCTGGAGGAGTTCCAAGAT
GTCTACTTAGTGATGGAACTGATGGACGCCAACCTGTGTCAGGTGATTCAGATGGAGCTGG
ACCACGAGCGGATGTCTTACTTGCTGTACCAGATGCTGTGTGGCATCAAGCACCTCCACTC
CGCTGGGATCATCCACAGGGACTTAAAACCCAGTAACATTGTAGTCAAGTCTGATTGCACA
CTGAAAATCCTCGACTTCGGACTGGCCAGGACAGCGGGTACAAGCTTCATGATGACTCCGT
ATGTGGTGACGCGATATTACAGAGCCCTGAGGTCATCCTGGGCATGGGCTACAAGGAGAA
CGTGGACATATGGTCTGTGGGATGCATCATGGGAGAAATGGTTCGCCACAAAATCCTCTTT
CCCGGAAGGAGCTATATTGACCAGTGGAACAAAGTCATCGAGCAGCTAGGAACTCCGTGTC
CAGAGTTCATGAAGAAATTGCAGCCCACAGTCAGAAACTACGTGGAGAATCGGCCCAAGTA
CGCAGGACTCACCTTCCCCAAGCTCTTTCCAGATTCCCTCTTCCCAGCGGATTCTGAGCAC
AATAAACTTAAAGCCAGCCAAGCCAGGGATTTGTTGTCTAAGATGTTAGTGATTGACCCAG
TGAAGAGGATATCGGTGGACGACGCACTGCAGCATCCGTACATCAACGTTTGGTACGACCC
GGCTGAAGTGGAGGCGCCTCCGCCTCAGATATATGATAAGCAGCTGGATGAAAGGGAGCAC
ACCATCGAAGAATGGAAAGAACTTATCTACAAGGAGGTAATGAACTCAGAAGAGAAGACTA
AGAATGGCGTAGTCAAAAGCCAGCCCTCGCCTTCAGCACAGGTGCAGCAGTGAACAGCAGT
GAGAGTCTCCCTCCATCCTCGGCTGTCAACGACATCTCCTCCATGTCCACCGACCAGACCC
TCGCATCTGACACTGACAGCAGCCTGGAGGCCTCGGCGGGACCGTTGGGTTGTTGCAGGTG
ACTAGCCGCCTGCCTGCGAAACCCAGCGTTCTTCAGGAGATGACGCGATAGAACACAGCAC
ACATGCACACACACAGCTTGCTCTCACACACACTCAGCTTGCTCACACACACACACACACA
TACACACAAACACACACTGTCTCTCTCACACACACACACTGTCACAACGCACTCACGAA
AGGTCAAGAAAAAATAACAATAGAGAGATCCAACATAAAATTAAGTTAAATTTTCTGCG
TGCTTCTCCAAAGTTCTGTATCACAGCTGAGCTGAAATGTATACTTAACTTCTAGTTGCGC
TCGCTTTGGTTTCCCTCCAGCAGTGCTTACTACACAAGACAAATCAGACACAATTAGAGAA
ACCTTTCCCTAAAGTGTAACTTAAGTGGCTGCAGAACCAGCAACCTGTAACTGCCCTTCAA
ATGGCATGAGGAGGTGGGCACGGGTCCCGCCCAGCATGTGTGTGTCTCTATCTCGCGTCTA
CCTGCTCTTCCGGCCTAGTCAGATGGATGTAGATACAGATCCCGCATGTCTGTATTCAA
ACAGCACTTAGAGATGCTCCTGTCAGTGTCCTCCAGGCTCCACCAAGACACACACCGGGGT
ACCACATGGTCCATTTCATGTGATCTATTACTCTGACATAAATCCATCTGTAATATATTGC
CAGTATATAAGCTGTTTAGTTTGTTAATTGCTTAAGCTGTATGTCTTATAAGAGACTATGT
AAAGGGGGAAAATGGAGGCGTGAACTCTCAGACCCTTGAAGATGTAGCTTCCGAATTTGAC
CGTTAAATGGCACCGTATACC (SEQ ID NO: 11)

FIG. 5B

MSLHFLYYCSEPTLDVKIAFCQGFDKHVDVSSIAKHYNMSKSKVDNQFYSVEVGDSTFTVL
KRYQNLKPIGSGAQGIVCAAYDAVLDRNVAIKKLSRPFQNQTHAKRAYRELVLMKCVNHKN
IISLLNVFTPQKTLEEFQDVYLVMELMDANLCQVIQMELDHERMSYLLYQMLCGIKHLHSA
GIIHRDLKPSNIVVKSDCTLKILDFGLARTAGTSFMMTPYVVTRYYRAPEVILGMGYKENV
DIWSVGCIMGEMVRHKILFPGRSYIDQWNKVIEQLGTPCPEFMKKLQPTVRNYVENRPKYA
GLTFPKLFPDSLFPADSEHNKLKASQARDLLSKMLVIDPVKRISVDDALQHPYINVWYDPA
EVEAPPPQIYDKQLDEREHTIEEWKELIYKEVMNSEEKTKNGVVKSQPSPSAQVQQ (SEQ ID NO: 12)

Fig. 9A

```
agcaactttc ctgacccaga ggaccggtaa caagtggccg ggagcaactt ttgcaaatct
cttctgcgcc ttaaggctgc caccgagact gtaaagaaaa ggagaagagg aacctatact
cataccagtt cgcacaggcc taagttgggc gaggcctagc cgcggctgcc tagcgtcccc
cccccccctca cagcggagga ggggacagtt gttggaggcc gggcggcaga cccgatcgcg
ggcctccacc gagaattccg tgacgactgg tcagcaccgc cggagagccg ctgttgctgg
gactggtctg cgggctccaa ggaaccgctg ctccccgaga gcgctccgtg agtgaccgcg
acttttcaaa gctcggcatc gcgcggagtc ctaccaacgt gagtgctagc ggagtcttaa
ccctgcgctc cctggagcga actggggagg agggctcagg gggaagcact gccgtctgga
gcgcacgctc taaacaaact ttgttacaga agcagggacg cgcgggtatc cccccgcttc
ccggcgcgct gttgcggccc cgaaacttct gcgcacagcc caggctaacc ccgcgtgaag
tgacggaccg ttctatgact gcaaagatgg aaacgacctt ctacgacgat gccctcaacg
cctcgttcct ccagtccgag agcggtgcct acggctacag taaccctaag atcctaaaac
agagcatgac cttgaacctg gccgacccgg tgggcagtct gaagccgcac ctccgcgcca
agaactcgga ccttctcacg tcgcccgacg tcgggctgct caagctggcg tcgccggagc
tggagcgcct gatcatccag tccagcaatg ggcacatcac cactacaccg accccccaccc
agttcttgtg ccccaagaac gtgaccgacg agcaggaggg cttcgccgag ggcttcgtgc
gcgccctggc tgaactgcat agccagaaca cgcttcccag tgtcacctcc gcggcacagc
cggtcagcgg ggcgggcatg gtggctcccg cggtggcctc agtagcaggc gctggcggcg
gtggtggcta cagcgccagc ctgcacagtg agcctccggt ctacgccaac ctcagcaact
tcaacccggg tgcgctgagc agcggcggtg gggcgccctc ctatggcgcg gccgggctgg
cctttccctc gcagccgcag cagcagcagc agccgcctca gccgccgcac cacttgcccc
aacagatccc ggtgcagcac ccgcggctgc aagccctgaa ggaagagccg cagaccgtgc
cggagatgcc gggagagacg ccgcccctgt ccctatcga catggagtct caggagcgga
tcaaggcaga gaggaagcgc atgaggaacc gcattgccgc ctccaagtgc cggaaaagga
agctggagcg gatcgctcgg ctagaggaaa aagtgaaaac cttgaaagcg caaaactccg
agctggcatc cacggccaac atgctcaggg aacaggtggc acagcttaag cagaaagtca
tgaaccacgt taacagtggg tgccaactca tgctaacgca gcagttgcaa acgttttgag
aacagactgt cagggctgag gggcaatgga agaaaaaaaa taacagagac aaacttgaga
acttgactgg ttgcgacaga gaaaaaaaaa gtgtccgagt actgaagcca agggtacaca
agatggactg ggttcggact gacggcgccc ccagtgtgct ctggagtggg aaggacgtgg
cgcgcctggc tttggcgtgg agccagagag caggcctatt ggccggcaga ctttgcggag
cgctgtgccg cgcgcgacca gaacgatgga cttttcgtta acattgacca agaactgcat
ggacctaaca ttcgatctca ttcagtatta aagggggggtg ggaggggtta caaactgcaa
tagagactgt agattgcttc tgtagtgctc cttaacacaa agcagggagg gctgggaagg
gggggaggct tgtaagtgcc aggctagact gcagatgaac tccccctggcc tgcctctctc
aactgtgtat gtacatatat attttttttt aatttgatga aagctgatta ctgtcaataa
acagcttcct gcctttgtaa gttattccat gtttgtttgt ttgggtgtcc tgcccagtgt
ttgtaaataa gagatttgaa gcattctgag tttaccattt gtaataaagt ataataattt
tttatgtttt gtttctgaaa atttccagaa aggatattta agaaaataca ataaactatt
gaaaagt    (SEQ ID NO:13)
```

Fig. 9B

```
            MTAKMETTFYDDALNASFLQSESGAYGYSNPKILKQSMTLNLAD
PVGSLKPHLRAKNSDLLTSPDVGLLKLASPELERLIIQSSNGHITTTPTPTQFLCPKN
VTDEQEGFAEGFVRALAELHSQNTLPSVTSAAQPVSGAGMVAPAVASVAGAGGGGGYS
ASLHSEPPVYANLSNFNPGALSSGGGAPSYGAAGLAFPSQPQQQQQPPQPPHHLPQQI
PVQHPRLQALKEEPQTVPEMPGETPPLSPIDMESQERIKAERKRMRNRIAASKCRKRK
LERIARLEEKVKTLKAQNSELASTANMLREQVAQLKQKVMNHVNSGCQLMLTQQLQTF
(SEQ ID NO:14)
```

Fig. 10A

```
ataccagaga ctcaaaaaaa aaaaaaaagt tccagattgc tggacaatga cccgggtctc
atcccttgac cctgggaacc gggtccacat tgaatcaggt gcgaatgttc gctcgccttc
tctgcctttc ccgcctcccc tcccccggcc gcggccccgg ttccccccct gcgctgcacc
ctcagagttg gctgcagccg gcgagctgtt cccgtcaatc cctccctcct ttacacagga
tgtccatatt aggacatctg cgtcagcagg tttccacggc cggtccctgt tgttctgggg
gggggaccat ctccgaaatc ctacacgcgg aaggtctagg agaccccta agatcccaaa
tgtgaacact cataggtgaa agatgtatgc caagacgggg gttgaaagcc tggggcgtag
agttgacgac agagcgcccg cagagggcct tggggcgcgc ttccccccc ttccagttcc
gcccagtgac gtaggaagtc catccattca cagcgcttct ataaaggcgc cagctgaggc
gcctactact ccaaccgcga ctgcagcgag caactgagaa gactggatag agccggcggt
tccgcgaacg agcagtgacc gcgctcccac ccagctctgc tctgcagctc ccaccagtgt
ctacccctgg accccttgcc gggctttccc caaacttcga ccatgatgtt ctcgggtttc
aacgccgact acgaggcgtc atcctcccgc tgcagtagcg cctccccggc cgggacagc
ctttcctact accattcccc agccgactcc ttctccagca tgggctctcc tgtcaacaca
caggtgagtt tggctttgtg tagccgccag gtccgcgctg agggtcgccg tggaggagac
actggggtgt gactcgcagg ggcgggggg tcttcctttt tcgctctgga gggagactgg
cgcggtcaga gcagccttag cctgggaacc caggacttgt ctgagcgcgt gcacacttgt
catagtaaga cttagtgacc ccttcccgcg cggcaggttt attctgagtg gcctgcctgc
attcttctct cggccgactt gtttctgaga tcagccgggg ccaacaagtc tcgagcaaag
agtcgctaac tagagtttgg gaggcggcaa accgcggcaa tcccccctcc cggggcagcc
tggagcaggg aggagggagg agggaggagg gtgctgcggg cgggtgtgta aggcagtttc
attgataaaa agcgagttca ttctggagac tccggagcag cgcctgcgtc agcgcagacg
tcagggatat ttataacaaa cccccttttcg agcgagtgat gccgaaggga taacgggaac
gcagcagtag gatggaggag aaaggctgcg ctgcggaatt caagggagga tattgggaga
gcttttatct ccgatgaggt gcatacagga agacataagc agtctctgac cggaatgctt
ctctctccct gcttcatgcg acactagggc cacttgctcc acctgtgtct ggaacctcct
cgctcacctc cgctttcctc ttttttgtttt gtttcaggac ttttgcgcag atctgtccgt
ctctagtgcc aactttatcc ccacggtgac agccatctcc accagcccag acctgcagtg
gctggtgcag cccactctgg tctcctccgt ggccccatcg cagaccagag cgccccatcc
ttacggactc cccacccagt ctgctggggc ttacgccaga gcgggaatgg tgaagaccgt
gtcaggaggc agagcgcaga gcatcggcag aaggggcaaa gtagagcagg tgagcagcga
ttctggacct ttgtgggctg gggggggggg ggggggcgga gactgacgca cagaccacac
aacagagaag ggacgctact gactgcactt cctgaccagg agctgtggct gctagcccctt
tccctccctt gtcagatttt gacagttgga cccaagacaa actctagaca gtttccctga
cagcttccta cttcattctc tagccgggga gcttctttgt tccctgctaa aagatctcac
tttaaatgca aatcacactc tgcctgccaa ctgcaggtta gaaaaactgc ttcaccgaga
ggtgcgggtg ctgtaggagc cagtttcact ggggtgactg aatggaggtg acactagaca
accttaactg aatgttggtc cttttcttct atagctatct cctgaagagg aagagaaacg
gagaatccga agggaacgga ataagatggc tgcagccaag tgccggaatc ggaggaggga
gctgacagat acactccaag cggtaggttg aaccagctgc tgctcctgaa actttattaa
agttggagct tgggactatg ggcgcaggt ccttgagcat gcccgtgtct tatgctttct
tatatctctc cctatgcagg agacagatca acttgaagat gagaagtctg cgttgcagac
tgagattgcc aatctgctga aagagaagga aaaactggag tttattttgg cagcccaccg
acctgcctgc aagatccccg atgaccttgg cttcccagag gagatgtctg tggcctccct
ggatttgact ggaggtctgc ctgaggcttc caccccagag tctgaggagg ccttcacccc
gcccccttctc aacgaccctg agcccaagcc atccttggag ccagtcaaga gcatcagcaa
cgtggagctg aaggcagaac cctttgatga cttcttgttt ccggcatcat ctaggcccag
tggctcagag acctcccgct ctgtgccaga tgtggacctg tccggttcct tctatgcagc
agactgggag cctctgcaca gcaattcctt ggggatgggg cccatggtca cagagctgga
gccctgtgt actcccgtgg tcacctgtac tccgggctgc actacttaca cgtcttcctt
tgtcttcacc taccctgaag ctgactcctt cccaagctgt gccgctgccc accgaaaggg
cagcagcagc aacgagccct cctccgactc cctgagctca cccacgctgc tggccctgtg
```

Fig. 10B

```
agcagtcaga gaaggcaagg cagccggcat ccagacgtgc cactgcccga gctggtgcat
tacagagagg agaaacacgt cttccctcga aggttcccgt cgacctaggg aggaccttac
ctgttcgtga aacacaccag gctgtgggcc tcaaggactt gcaagcatcc acatctggcc
tccagtcctc acctcttcca gagatgtagc aaaaacaaaa caaaacaaaa caaaaaaccg
catggagtgt gttgttccta gtgacacctg agagctggta gttagtagag catgtgagtc
aaggcctggt ctgtgtctct tttctctttc tccttagttt tctcatagca ctaactaatc
tgttgggttc attattggaa ttaacctggt gctggattgt atctagtgca gctgatttta
acaataccta ctgtgttcct ggcaatagcg tgttccaatt agaaacgacc aatattaaac
taagaaaaga taggacttta ttttccagta gatagaaatc aatagctata tccatgtact
gtagtccttc agcgtcaatg ttcattgtca tgttactgat catgcattgt cgaggtggtc
tgaatgttct gacattaaca gttttccatg aaaacgtttt tattgtgttt tcaatttatt
tattaagatg gattctcaga tatttatatt tttattttat ttttttctac cctgaggtct
ttcgacatgt ggaaagtgaa tttgaatgaa aaatttttaag cattgtttgc ttattgttcc
aggacattgt caataaaagc atttaagttg aatgcgacca ccttcttgct ctctttattc
tcagttt   (SEQ ID NO:15)
```

Fig. 10C

MMFSGFNADYEASSSRCSSASPAGDSLSYYHSPADSFSSMGSPV
NTQDFCADLSVSSANFIPTVTAISTSPDLQWLVQPTLVSSVAPSQTRAPHPYGLPTQS
AGAYARAGMVKTVSGGRAQSIGRRGKVEQLSPEEEEKRRIRRERNKMAAAKCRNRRRE
LTDTLQAETDQLEDEKSALQTEIANLLKEKEKLEFILAAHRPACKIPDDLGFPEEMSV
ASLDLTGGLPEASTPESEEAFTLPLLNDPEPKPSLEPVKSISNVELKAEPFDDLFPA
SSRPSGSETSRSVPDVDLSGSFYAADWEPLHSNSLGMGPMVTELEPLCTPVVTCTPGC
TTYTSSFVFTYPEADSFPSCAAAHRKGSSSNEPSSDSLSSPTLLAL    (SEQ ID NO:16)

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 1505 base pairs
      (B) TYPE: nucleic acid
      (C) STRANDEDNESS: double
      (D) TOPOLOGY: linear (ii) MOLECULE TYPE: DNA (ix) FEATURE:
      (A) NAME/KEY: Coding Sequence
      (B) LOCATION: 68...1459

(xi) SEQUENCE DESCRIPTION: SEQ ID NO: 1:

```
TTATGCAAGA AACTGTTGAA TTAGACCCGT TTCCTATAGA TGAGAAACCA TACAAGCTG              60

GGTATTT ATG AGC CTC CAT TTC TTA TAC TAC TGC AGT GAA CCA ACA TTG             109
        Met Ser Leu His Phe Leu Tyr Tyr Cys Ser Glu Pro Thr Leu
          1               5                  10

GAT GTG AAA ATT GCC TTT TGT CAG GGA TTC GAT AAA CAA GTG GAT GTG            157
Asp Val Lys Ile Ala Phe Cys Gln Gly Phe Asp Lys Gln Val Asp Val
 15                  20                  25                  30

TCA TAT ATT GCC AAA CAT TAC AAC ATG AGC AAA AGC AAA GTT GAC AAC            205
Ser Tyr Ile Ala Lys His Tyr Asn Met Ser Lys Ser Lys Val Asp Asn
                 35                  40                  45

CAG TTC TAC AGT GTG GAA GTG GGA GAC TCA ACC TTC ACA GTT CTC AAG            253
Gln Phe Tyr Ser Val Glu Val Gly Asp Ser Thr Phe Thr Val Leu Lys
             50                  55                  60
```

-continued

```
CGC TAC CAG AAT CTA AAG CCT ATT GGC TCT GGG GCT CAG GGC ATA GTT    301
Arg Tyr Gln Asn Leu Lys Pro Ile Gly Ser Gly Ala Gln Gly Ile Val
         65                  70                  75

TGT GCC GCG TAT GAT GCT GTC CTT GAC AGA AAT GTG GCC ATT AAG AAG    349
Cys Ala Ala Tyr Asp Ala Val Leu Asp Arg Asn Val Ala Ile Lys Lys
 80                  85                  90

CTC AGC AGA CCC TTT CAG AAC CAA ACA CAT GCC AAG AGA GCG TAC CGG    397
Leu Ser Arg Pro Phe Gln Asn Gln Thr His Ala Lys Arg Ala Tyr Arg
 95                 100                 105                 110

GAG CTG GTC CTC ATG AAG TGT GTG AAC CAT AAA AAC ATT ATT AGT TTA    445
Glu Leu Val Leu Met Lys Cys Val Asn His Lys Asn Ile Ile Ser Leu
                    115                 120                 125

TTA AAT GTC TTC ACA CCC CAG AAA ACG CTG GAG GAG TTC CAA GAT GTT    493
Leu Asn Val Phe Thr Pro Gln Lys Thr Leu Glu Glu Phe Gln Asp Val
                130                 135                 140

TAC TTA GTA ATG GAA CTG ATG GAT GCC AAC TTA TGT CAA GTG ATT CAG    541
Tyr Leu Val Met Glu Leu Met Asp Ala Asn Leu Cys Gln Val Ile Gln
            145                 150                 155

ATG GAA TTA GAC CAT GAG CGA ATG TCT TAC CTG CTG TAC CAA ATG TTG    589
Met Glu Leu Asp His Glu Arg Met Ser Tyr Leu Leu Tyr Gln Met Leu
        160                 165                 170

TGT GGC ATT AAG CAC CTC CAT TCT GCT GGA ATT ATT CAC AGG GAT TTA    637
Cys Gly Ile Lys His Leu His Ser Ala Gly Ile Ile His Arg Asp Leu
175                 180                 185                 190

AAA CCA AGT AAC ATT GTA GTC AAG TCT GAT TGC ACA TTG AAA ATC CTG    685
Lys Pro Ser Asn Ile Val Val Lys Ser Asp Cys Thr Leu Lys Ile Leu
                    195                 200                 205

GAC TTT GGA CTG GCC AGG ACA GCA GGC ACA AGC TTC ATG ATG ACT CCA    733
Asp Phe Gly Leu Ala Arg Thr Ala Gly Thr Ser Phe Met Met Thr Pro
                210                 215                 220

TAT GTG GTG ACA CGT TAT TAC AGA GCC CCT GAG GTC ATC CTG GGG ATG    781
Tyr Val Val Thr Arg Tyr Tyr Arg Ala Pro Glu Val Ile Leu Gly Met
            225                 230                 235

GGC TAC AAG GAG AAC GTG GAT ATA TGG TCT GTG GGA TGC ATT ATG GGA    829
Gly Tyr Lys Glu Asn Val Asp Ile Trp Ser Val Gly Cys Ile Met Gly
        240                 245                 250

GAA ATG GTT CGC CAC AAA ATC CTC TTT CCA GGA AGG GAC TAT ATT GAC    877
Glu Met Val Arg His Lys Ile Leu Phe Pro Gly Arg Asp Tyr Ile Asp
255                 260                 265                 270

CAG TGG AAT AAG GTA ATT GAA CAA CTA GGA ACA CCA TGT CCA GAA TTC    925
Gln Trp Asn Lys Val Ile Glu Gln Leu Gly Thr Pro Cys Pro Glu Phe
                    275                 280                 285

ATG AAG AAA TTG CAA CCC ACA GTA AGA AAC TAT GTG GAG AAT CGG CCC    973
Met Lys Lys Leu Gln Pro Thr Val Arg Asn Tyr Val Glu Asn Arg Pro
                290                 295                 300

AAG TAT GCG GGA CTC ACC TTC CCC AAA CTC TTC CCA GAT TCC CTC TT    1021
Lys Tyr Ala Gly Leu Thr Phe Pro Lys Leu Phe Pro Asp Ser Leu Phe
            305                 310                 315

CCA GCG GAC TCC GAG CAC AAT AAA CTC AAA GCC AGC CAA GCC AGG GA    1069
Pro Ala Asp Ser Glu His Asn Lys Leu Lys Ala Ser Gln Ala Arg Asp
        320                 325                 330

TTG TTG TCA AAG ATG CTA GTG ATT GAC CCA GCA AAA AGA ATA TCA GT    1117
Leu Leu Ser Lys Met Leu Val Ile Asp Pro Ala Lys Arg Ile Ser Val
335                 340                 345                 350

GAC GAC GCC TTA CAG CAT CCC TAC ATC AAC GTC TGG TAT GAC CCA GC    1165
Asp Asp Ala Leu Gln His Pro Tyr Ile Asn Val Trp Tyr Asp Pro Ala
                    355                 360                 365

GAA GTG GAG GCG CCT CCA CCT CAG ATA TAT GAC AAG CAG TTG GAT GA    1213
Glu Val Glu Ala Pro Pro Pro Gln Ile Tyr Asp Lys Gln Leu Asp Glu
                370                 375                 380
```

-continued

```
AGA GAA CAC ACA ATT GAA GAA TGG AAA GAA CTT ATC TAC AAG GAA GT      1261
Arg Glu His Thr Ile Glu Glu Trp Lys Glu Leu Ile Tyr Lys Glu Val
            385                 390                 395

ATG AAT TCA GAA GAA AAG ACT AAA AAT GGT GTA GTA AAA GGA CAG CC      1309
Met Asn Ser Glu Glu Lys Thr Lys Asn Gly Val Val Lys Gly Gln Pro
    400                 405                 410

TCT CCT TCA GGT GCA GCA GTG AAC AGC AGT GAG AGT CTC CCT CCA TC      1357
Ser Pro Ser Gly Ala Ala Val Asn Ser Ser Glu Ser Leu Pro Pro Ser
415                 420                 425                 430

TCG TCT GTC AAT GAC ATC TCC TCC ATG TCC ACC GAC CAG ACC CTG GC      1405
Ser Ser Val Asn Asp Ile Ser Ser Met Ser Thr Asp Gln Thr Leu Ala
                435                 440                 445

TCT GAC ACT GAC AGC AGC CTG GAA GCC TCG GCA GGA CCC CTG GGT TG      1453
Ser Asp Thr Asp Ser Ser Leu Glu Ala Ser Ala Gly Pro Leu Gly Cys
            450                 455                 460

TGC AGG TGACTAGCCG CCTGCCTGCG AAACCCAGCG TTCTTCAGGA GATGAT         1505
Cys Arg
```

(2) INFORMATION FOR SEQ ID NO: 2:

(i) SEQUENCE CHARACTERISTICS:
        (A) LENGTH: 464 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 2:

```
Met Ser Leu His Phe Leu Tyr Tyr Cys Ser Glu Pro Thr Leu Asp Val
 1               5                  10                  15

Lys Ile Ala Phe Cys Gln Gly Phe Asp Lys Gln Val Asp Val Ser Tyr
            20                  25                  30

Ile Ala Lys His Tyr Asn Met Ser Lys Ser Lys Val Asp Asn Gln Phe
        35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
    210                 215                 220
```

```
Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
            245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
            275                 280                 285

Lys Leu Gln Pro Thr Val Arg Asn Tyr Val Glu Asn Arg Pro Lys Tyr
290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
                340                 345                 350

Ala Leu Gln His Pro Tyr Ile Asn Val Trp Tyr Asp Pro Ala Glu Val
                355                 360                 365

Glu Ala Pro Pro Pro Gln Ile Tyr Asp Lys Gln Leu Asp Glu Arg Glu
370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Gly Ala Ala Val Asn Ser Ser Glu Ser Leu Pro Pro Ser Ser Ser
                420                 425                 430

Val Asn Asp Ile Ser Ser Met Ser Thr Asp Gln Thr Leu Ala Ser Asp
                435                 440                 445

Thr Asp Ser Ser Leu Glu Ala Ser Ala Gly Pro Leu Gly Cys Cys Arg
450                 455                 460
```

(2) INFORMATION FOR SEQ ID NO: 3:

(i) SEQUENCE CHARACTERISTICS:
        (A) LENGTH: 2367 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 3:

```
GAGAAATGGC GTGGCAGGGG ACCCAGCGAG CCCAGAGGGA TTTTGCCGCT GCTTCCTCT      60

CCCCTGTATT TCACGCAGCT CTCTAAATTG ACTCAGCTCC AGGCTAGTGT GAGAAACA      120

AACAGCAGGC CCATCTCAGA TCTTCACTAT GGCAACTTAT GCAAGAAACT GTTGAATT      180

ACCCGTTTCC TATAGATGAG AAACCATACA AGCTGTGGTA TTTATGAGCC TCCATTTC      240

ATACTACTGC AGTGAACCAA CATTGGATGT GAAAATTGCC TTTTGTCAGG GATTCGAT      300

ACAAGTGGAT GTGTCATATA TTGCCAAACA TTACAACATG AGCAAAAGCA AAGTTGAC      360

CCAGTTCTAC AGTGTGGAAG TGGGAGACTC AACCTTCACA GTTCTCAAGC GCTACCAG      420

TCTAAAGCCT ATTGGCTCTG GGCTCAGGG CATAGTTTGT GCCGCGTATG ATGCTGTC      480

TGACAGAAAT GTGGCCATTA AGAAGCTCAG CAGACCCTTT CAGAACCAAA CACATGCC      540

GAGAGCGTAC CGGGAGCTGG TCCTCATGAA GTGTGTGAAC CATAAAAACA TTATTAGT      600
```

```
ATTAAATGTC TTCACACCCC AGAAAACGCT GGAGGAGTTC CAAGATGTTT ACTTAGTA      660

GGAACTGATG GATGCCAACT TATGTCAAGT GATTCAGATG GAATTAGACC ATGAGCGA      720

GTCTTACCTG CTGTACCAAA TGTTGTGTGG CATTAAGCAC CTCCATTCTG CTGGAATT      780

TCACAGGGAT TTAAAACCAA GTAACATTGT AGTCAAGTCT GATTGCACAT TGAAAATC      840

GGACTTTGGA CTGGCCAGGA CAGCAGGCAC AAGCTTCATG ATGACTCCAT ATGTGGTG      900

ACGTTATTAC AGAGCCCCTG AGGTCATCCT GGGGATGGGC TACAAGGAGA ACGTGGAT      960

ATGGTCTGTG GGATGCATTA TGGGAGAAAT GGTTCGCCAC AAAATCCTCT TTCCAGG       1020

GGACTATATT GACCAGTGGA ATAAGGTAAT TGAACAACTA GGAACACCAT GTCCAGA       1080

CATGAAGAAA TTGCAACCCA CAGTAAGAAA CTATGTGGAG AATCGGCCCA AGTATGC       1140

ACTCACCTTC CCCAAACTCT TCCCAGATTC CCTCTTCCCA GCGGACTCCG AGCACAA       1200

ACTCAAAGCC AGCCAAGCCA GGGACTTGTT GTCAAAGATG CTAGTGATTG ACCCAGC       1260

AAGAATATCA GTGGACGACG CCTTACAGCA TCCCTACATC AACGTCTGGT ATGACCC       1320

CGAAGTGGAG GCGCCTCCAC CTCAGATATA TGACAAGCAG TTGGATGAAA GAGAACA       1380

AATTGAAGAA TGGAAAGAAC TTATCTACAA GGAAGTAATG AATTCAGAAG AAAAGAC       1440

AAATGGTGTA GTAAAAGGAC AGCCTTCTCC TTCAGGTGCA GCAGTGAACA GCAGTGA       1500

TCTCCCTCCA TCCTCGTCTG TCAATGACAT CTCCTCCATG TCCACCGACC AGACCCT       1560

ATCTGACACT GACAGCAGCC TGGAAGCCTC GGCAGGACCC CTGGGTTGTT GCAGGTG       1620

AGCCGCCTGC CTGCGAAACC CAGCGTTCTT CAGGAGATGA TGTGATGGAA CACACAC       1680

CGCAGACACA CACACACACA CAAATGCAGA CACACAACAT CAAGAAAACA GCAAGGG       1740

GAATCCAAGC CTAAAATTAA ATAAATCTTT CAGCCTGCTT CTTCCCCAGG GTTCTGT       1800

GCAGCTAAGC TCAAATGTAT ATTTAACTTC TAGTTGCTCT TGCTTTGGTC TTCTTCC       1860

GATGCTTACT ACAGAAAGCA AATCAGACAC AATTAGAGAA GCCTTTTCCA TAAAGTG       1920

TTTTAATGGC TGCAAAACCG GCAACCTGTA ACTGCCCTTT TAAATGGCAT GACAAGG       1980

GCAGTGGCCC CATCCAGCAT GTGTGTGTCT CTATCTTGCA TCTACCTGCT CCTTGGC       2040

GTCAGATGGA TGTAGATACA GATCCGCATG TGTCTGTATT CATACAGCAC TACTTAC       2100

GAGATGCTAC TCTCAGTGTC CTCAGGGCTC TACCAAGACA TAATGCACTG GGGTACC       2160

TGGTCCATTT CATGTGATCT ATTACTCTGA CATAAACCCA TCTGTAATAT ATTGCCA       2220

TATAAGCTGT TTAGTTTGTT AATTGATTAA ACTGTATGTC TTATAAGAAA ACATGTA       2280

GGGGAATATA TTGGGGGAGT GAGCTCTCTC AGACCCTTGA AGATGTAGCT TCCAAAT       2340

AATGGATTAA ATGGCACCTG TATACCA                                       2367
```

(2) INFORMATION FOR SEQ ID NO: 4:

(i) SEQUENCE CHARACTERISTICS:
        (A) LENGTH: 1773 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: Coding Sequence
        (B) LOCATION: 92...1357

(xi) SEQUENCE DESCRIPTION: SEQ ID NO: 4:

```
ATCTCAGATC TTCACTATGG CAACTTATGC AAGAAACTGT TGAATTAGAC CCGTTTCCT      60
```

-continued

| | |
|---|---|
| TAGATGAGAA ACCATACAAG CTGTGGTATT T ATG AGC CTC CAT TTC TTA TAC<br>                                                                Met Ser Leu His Phe Leu Tyr<br>                                                                 1               5 | 112 |
| TAC TGC AGT GAA CCA ACA TTG GAT GTG AAA ATT GCC TTT TGT CAG GGA<br>Tyr Cys Ser Glu Pro Thr Leu Asp Val Lys Ile Ala Phe Cys Gln Gly<br>          10                    15                    20 | 160 |
| TTC GAT AAA CAA GTG GAT GTG TCA TAT ATT GCC AAA CAT TAC AAC ATG<br>Phe Asp Lys Gln Val Asp Val Ser Tyr Ile Ala Lys His Tyr Asn Met<br>     25                    30                    35 | 208 |
| AGC AAA AGC AAA GTT GAC AAC CAG TTC TAC AGT GTG GAA GTG GGA GAC<br>Ser Lys Ser Lys Val Asp Asn Gln Phe Tyr Ser Val Glu Val Gly Asp<br>40                    45                    50                    55 | 256 |
| TCA ACC TTC ACA GTT CTC AAG CGC TAC CAG AAT CTA AAG CCT ATT GGC<br>Ser Thr Phe Thr Val Leu Lys Arg Tyr Gln Asn Leu Lys Pro Ile Gly<br>                   60                    65                    70 | 304 |
| TCT GGG GCT CAG GGC ATA GTT TGT GCC GCG TAT GAT GCT GTC CTT GAC<br>Ser Gly Ala Gln Gly Ile Val Cys Ala Ala Tyr Asp Ala Val Leu Asp<br>                  75                    80                    85 | 352 |
| AGA AAT GTG GCC ATT AAG AAG CTC AGC AGA CCC TTT CAG AAC CAA ACA<br>Arg Asn Val Ala Ile Lys Lys Leu Ser Arg Pro Phe Gln Asn Gln Thr<br>          90                    95                    100 | 400 |
| CAT GCC AAG AGA GCG TAC CGG GAG CTG GTC CTC ATG AAG TGT GTG AAC<br>His Ala Lys Arg Ala Tyr Arg Glu Leu Val Leu Met Lys Cys Val Asn<br>     105                   110                   115 | 448 |
| CAT AAA AAC ATT ATT AGT TTA TTA AAT GTC TTC ACA CCC CAG AAA ACG<br>His Lys Asn Ile Ile Ser Leu Leu Asn Val Phe Thr Pro Gln Lys Thr<br>120                   125                   130                 135 | 496 |
| CTG GAG GAG TTC CAA GAT GTT TAC TTA GTA ATG GAA CTG ATG GAT GCC<br>Leu Glu Glu Phe Gln Asp Val Tyr Leu Val Met Glu Leu Met Asp Ala<br>                   140                   145                 150 | 544 |
| AAC TTA TGT CAA GTG ATT CAG ATG GAA TTA GAC CAT GAG CGA ATG TCT<br>Asn Leu Cys Gln Val Ile Gln Met Glu Leu Asp His Glu Arg Met Ser<br>               155                   160                 165 | 592 |
| TAC CTG CTG TAC CAA ATG TTG TGT GGC ATT AAG CAC CTC CAT TCT GCT<br>Tyr Leu Leu Tyr Gln Met Leu Cys Gly Ile Lys His Leu His Ser Ala<br>          170                   175                  180 | 640 |
| GGA ATT ATT CAC AGG GAT TTA AAA CCA AGT AAC ATT GTA GTC AAG TCT<br>Gly Ile Ile His Arg Asp Leu Lys Pro Ser Asn Ile Val Val Lys Ser<br>           185                   190                 195 | 688 |
| GAT TGC ACA TTG AAA ATC CTG GAC TTT GGA CTG GCC AGG ACA GCA GGC<br>Asp Cys Thr Leu Lys Ile Leu Asp Phe Gly Leu Ala Arg Thr Ala Gly<br>200                   205                   210                 215 | 736 |
| ACA AGC TTC ATG ATG ACT CCA TAT GTG GTG ACA CGT TAT TAC AGA GCC<br>Thr Ser Phe Met Met Thr Pro Tyr Val Val Thr Arg Tyr Tyr Arg Ala<br>                   220                   225                 230 | 784 |
| CCT GAG GTC ATC CTG GGG ATG GGC TAC AAG GAG AAC GTG GAT ATA TGG<br>Pro Glu Val Ile Leu Gly Met Gly Tyr Lys Glu Asn Val Asp Ile Trp<br>          235                   240                 245 | 832 |
| TCT GTG GGA TGC ATT ATG GGA GAA ATG GTT CGC CAC AAA ATC CTC TTT<br>Ser Val Gly Cys Ile Met Gly Glu Met Val Arg His Lys Ile Leu Phe<br>          250                   255                 260 | 880 |
| CCA GGA AGG GAC TAT ATT GAC CAG TGG AAT AAG GTA ATT GAA CAA CTA<br>Pro Gly Arg Asp Tyr Ile Asp Gln Trp Asn Lys Val Ile Glu Gln Leu<br>     265                   270                   275 | 928 |
| GGA ACA CCA TGT CCA GAA TTC ATG AAG AAA TTG CAA CCC ACA GTA AGA<br>Gly Thr Pro Cys Pro Glu Phe Met Lys Lys Leu Gln Pro Thr Val Arg<br>280                   285                   290                 295 | 976 |
| AAC TAT GTG GAG AAT CGG CCC AAG TAT GCG GGA CTC ACC TTC CCC AA<br>Asn Tyr Val Glu Asn Arg Pro Lys Tyr Ala Gly Leu Thr Phe Pro Lys<br>                   300                   305                 310 | 1024 |

```
CTC TTC CCA GAT TCC CTC TTC CCA GCG GAC TCC GAG CAC AAT AAA CT      1072
Leu Phe Pro Asp Ser Leu Phe Pro Ala Asp Ser Glu His Asn Lys Leu
                315                 320                 325

AAA GCC AGC CAA GCC AGG GAC TTG TTG TCA AAG ATG CTA GTG ATT GA      1120
Lys Ala Ser Gln Ala Arg Asp Leu Leu Ser Lys Met Leu Val Ile Asp
            330                 335                 340

CCA GCA AAA AGA ATA TCA GTG GAC GAC GCC TTA CAG CAT CCC TAC AT      1168
Pro Ala Lys Arg Ile Ser Val Asp Asp Ala Leu Gln His Pro Tyr Ile
        345                 350                 355

AAC GTC TGG TAT GAC CCA GCC GAA GTG GAG GCG CCT CCA CCT CAG AT      1216
Asn Val Trp Tyr Asp Pro Ala Glu Val Glu Ala Pro Pro Pro Gln Ile
360                 365                 370                 375

TAT GAC AAG CAG TTG GAT GAA AGA GAA CAC ACA ATT GAA GAA TGG AA      1264
Tyr Asp Lys Gln Leu Asp Glu Arg Glu His Thr Ile Glu Glu Trp Lys
                380                 385                 390

GAA CTT ATC TAC AAG GAA GTA ATG AAT TCA GAA GAA AAG ACT AAA AA      1312
Glu Leu Ile Tyr Lys Glu Val Met Asn Ser Glu Glu Lys Thr Lys Asn
            395                 400                 405

GGT GTA GTA AAA GGA CAG CCT TCT CCT TCA GCA CAG GTG CAG CAG          1357
Gly Val Val Lys Gly Gln Pro Ser Pro Ser Ala Gln Val Gln Gln
        410                 415                 420

TGAACAGCAG TGAGAGTCTC CCTCCATCCT CGTCTGTCAA TGACATCTCC TCCATGT      1417

CCGACCAGAC CCTGGCATCT GACACTGACA GCAGCCTGGA AGCCTCGGCA GGACCCC      1477

GTTGTTGCAG GTGACTAGCC GCCTGCCTGC GAAACCCAGC GTTCTTCAGG AGATGAT      1537

ATGGAACACA CACACACGCA GACACACACA CACACACAAA TGCAGACACA CAACATC      1597

AAAACAGCAA GGGAGAGAAT CCAAGCCTAA AATTAAATAA ATCTTTCAGC CTGCTTC      1657

CCCAGGGTTC TGTATTGCAG CTAAGCTCAA ATGTATATTT AACTTCTAGT TGCTCTT      1717

TTGGTCTTCT TCCAATGATG CTTACTACAG AAAGCAAATC AGACACAATT AGAGAA      1773

(2) INFORMATION FOR SEQ ID NO: 5:

(i) SEQUENCE CHARACTERISTICS:
        (A) LENGTH: 422 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 5:

Met Ser Leu His Phe Leu Tyr Tyr Cys Ser Glu Pro Thr Leu Asp Val
 1               5                  10                  15

Lys Ile Ala Phe Cys Gln Gly Phe Asp Lys Gln Val Asp Val Ser Tyr
                20                  25                  30

Ile Ala Lys His Tyr Asn Met Ser Lys Ser Lys Val Asp Asn Gln Phe
            35                  40                  45

Tyr Ser Val Glu Val Gly Asp Ser Thr Phe Thr Val Leu Lys Arg Tyr
        50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
```

```
                 115                 120                 125
Val Phe Thr Pro Gln Lys Thr Leu Glu Glu Phe Gln Asp Val Tyr Leu
        130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Ala Gln Val Gln Gln
            420

(2) INFORMATION FOR SEQ ID NO: 6:

(i) SEQUENCE CHARACTERISTICS:
        (A) LENGTH: 2372 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 6:

GAGAAATGGC GTGGCAGGGG ACCCAGCGAG CCCAGAGGGA TTTTGCCGCT GCTTCCTCT      60

CCCCTGTATT TCACGCAGCT CTCTAAATTG ACTCAGCTCC AGGCTAGTGT GAGAAACA      120

AACAGCAGGC CCATCTCAGA TCTTCACTAT GGCAACTTAT GCAAGAAACT GTTGAATT      180

ACCCGTTTCC TATAGATGAG AAACCATACA AGCTGTGGTA TTTATGAGCC TCCATTTC      240
```

```
ATACTACTGC AGTGAACCAA CATTGGATGT GAAAATTGCC TTTTGTCAGG GATTCGAT         300
ACAAGTGGAT GTGTCATATA TTGCCAAACA TTACAACATG AGCAAAAGCA AAGTTGAC         360
CCAGTTCTAC AGTGTGGAAG TGGGAGACTC AACCTTCACA GTTCTCAAGC GCTACCAG         420
TCTAAAGCCT ATTGGCTCTG GGGCTCAGGG CATAGTTTGT GCCGCGTATG ATGCTGTC         480
TGACAGAAAT GTGGCCATTA AGAAGCTCAG CAGACCCTTT CAGAACCAAA CACATGCC         540
GAGAGCGTAC CGGGAGCTGG TCCTCATGAA GTGTGTGAAC CATAAAAACA TTATTAGT         600
ATTAAATGTC TTCACACCCC AGAAAACGCT GGAGGAGTTC AAGATGTTT ACTTAGTA          660
GGAACTGATG GATGCCAACT TATGTCAAGT GATTCAGATG GAATTAGACC ATGAGCGA         720
GTCTTACCTG CTGTACCAAA TGTTGTGTGG CATTAAGCAC CTCCATTCTG CTGGAATT         780
TCACAGGGAT TTAAAACCAA GTAACATTGT AGTCAAGTCT GATTGCACAT TGAAAATC         840
GGACTTTGGA CTGGCCAGGA CAGCAGGCAC AAGCTTCATG ATGACTCCAT ATGTGGTG         900
ACGTTATTAC AGAGCCCCTG AGGTCATCCT GGGGATGGGC TACAAGGAGA ACGTGGAT         960
ATGGTCTGTG GGATGCATTA TGGGAGAAAT GGTTCGCCAC AAAATCCTCT TTCCAGG         1020
GGACTATATT GACCAGTGGA ATAAGGTAAT TGAACAACTA GGAACACCAT GTCCAGA         1080
CATGAAGAAA TTGCAACCCA CAGTAAGAAA CTATGTGGAG AATCGGCCCA AGTATGC         1140
ACTCACCTTC CCCAAACTCT TCCCAGATTC CCTCTTCCCA GCGGACTCCG AGCACAA         1200
ACTCAAAGCC AGCCAAGCCA GGGACTTGTT GTCAAAGATG CTAGTGATTG ACCCAGC         1260
AAGAATATCA GTGGACGACG CCTTACAGCA TCCCTACATC AACGTCTGGT ATGACCC         1320
CGAAGTGGAG GCGCCTCCAC CTCAGATATA TGACAAGCAG TTGGATGAAA GAGAACA         1380
AATTGAAGAA TGGAAAGAAC TTATCTACAA GGAAGTAATG AATTCAGAAG AAAAGAC         1440
AAATGGTGTA GTAAAAGGAC AGCCTTCTCC TTCAGCACAG GTGCAGCAGT GAACAGC         1500
GAGAGTCTCC CTCCATCCTC GTCTGTCAAT GACATCTCCT CCATGTCCAC CGACCAG         1560
CTGGCATCTG ACACTGACAG CAGCCTGGAA GCCTCGGCAG GACCCCTGGG TTGTTGC         1620
TGACTAGCCG CCTGCCTGCG AAACCCAGCG TTCTTCAGGA GATGATGTGA TGGAACA         1680
ACACACGCAG ACACACACAC ACACACAAAT GCAGACACAC AACATCAAGA AAACAGC         1740
GGAGAGAATC CAAGCCTAAA ATTAAATAAA TCTTTCAGCC TGCTTCTTCC CCAGGGT         1800
GTATTGCAGC TAAGCTCAAA TGTATATTTA ACTTCTAGTT GCTCTTGCTT TGGTCTT         1860
CCAATGATGC TTACTACAGA AAGCAAATCA GACACAATTA GAAGAGCCTT TTCCATA         1920
TGTAATTTTA ATGGCTGCAA AACCGGCAAC CTGTAACTGC CCTTTTAAAT GGCATGA         1980
GGTGTGCAGT GGCCCCATCC AGCATGTGTG TGTCTCTATC TTGCATCTAC CTGCTCC         2040
GCCTAGTCAG ATGGATGTAG ATACAGATCC GCATGTGTCT GTATTCATAC AGCACTA         2100
ACTTAGAGAT GCTACTCTCA GTGTCCTCAG GGCTCTACCA AGACATAATG CACTGGG         2160
CCACATGGTC CATTTCATGT GATCTATTAC TCTGACATAA ACCCATCTGT AATATAT         2220
CAGTATATAA GCTGTTTAGT TTGTTAATTG ATTAAACTGT ATGTCTTATA AGAAAAC         2280
TAAAGGGGGA ATATATTGGG GGAGTGAGCT CTCTCAGACC CTTGAAGATG TAGCTTC         2340
ATTTGAATGG ATTAAATGGC ACCTGTATAC CA                                    2372
```

(2) INFORMATION FOR SEQ ID NO: 7:

(i) SEQUENCE CHARACTERISTICS:
    (A) LENGTH: 2372 base pairs
    (B) TYPE: nucleic acid (C) STRANDEDNESS: double
        (D) TOPOLOGY: linear (ii) MOLECULE TYPE: DNA (ix) FEATURE:
        (A) NAME/KEY: Coding Sequence
        (B) LOCATION: 224...1489

(xi) SEQUENCE DESCRIPTION: SEQ ID NO: 7:

```
GAGAAATGGC GTGGCAGGGG ACCCAGCGAG CCCAGAGGGA TTTTGCCGCT GCTTCCTCT        60

CCCCTGTATT TCACGCAGCT CTCTAAATTG ACTCAGCTCC AGGCTAGTGT GAGAAACA        120

AACAGCAGGC CCATCTCAGA TCTTCACTAT GGCAACTTAT GCAAGAAACT GTTGAATT        180

ACCCGTTTCC TATAGATGAG AAACCATACA AGCTGTGGTA TTT ATG AGC CTC CAT        235
                                              Met Ser Leu His
                                                1

TTC TTA TAC TAC TGC AGT GAA CCA ACA TTG GAT GTG AAA ATT GCC TTT        283
Phe Leu Tyr Tyr Cys Ser Glu Pro Thr Leu Asp Val Lys Ile Ala Phe
  5              10                 15                  20

TGT CAG GGA TTC GAT AAA CAA GTG GAT GTG TCA TAT ATT GCC AAA CAT        331
Cys Gln Gly Phe Asp Lys Gln Val Asp Val Ser Tyr Ile Ala Lys His
             25                 30                  35

TAC AAC ATG AGC AAA AGC AAA GTT GAC AAC CAG TTC TAC AGT GTG GAA        379
Tyr Asn Met Ser Lys Ser Lys Val Asp Asn Gln Phe Tyr Ser Val Glu
         40                 45                  50

GTG GGA GAC TCA ACC TTC ACA GTT CTC AAG CGC TAC CAG AAT CTA AAG        427
Val Gly Asp Ser Thr Phe Thr Val Leu Lys Arg Tyr Gln Asn Leu Lys
     55                 60                  65

CCT ATT GGC TCT GGG GCT CAG GGC ATA GTT TGT GCC GCG TAT GAT GCT        475
Pro Ile Gly Ser Gly Ala Gln Gly Ile Val Cys Ala Ala Tyr Asp Ala
 70                 75                  80

GTC CTT GAC AGA AAT GTG GCC ATT AAG AAG CTC AGC AGA CCC TTT CAG        523
Val Leu Asp Arg Asn Val Ala Ile Lys Lys Leu Ser Arg Pro Phe Gln
 85                 90                  95                 100

AAC CAA ACA CAT GCC AAG AGA GCG TAC CGG GAG CTG GTC CTC ATG AAG        571
Asn Gln Thr His Ala Lys Arg Ala Tyr Arg Glu Leu Val Leu Met Lys
             105                110                 115

TGT GTG AAC CAT AAA AAC ATT ATT AGT TTA TTA AAT GTC TTC ACA CCC        619
Cys Val Asn His Lys Asn Ile Ile Ser Leu Leu Asn Val Phe Thr Pro
         120                125                 130

CAG AAA ACG CTG GAG GAG TTC CAA GAT GTT TAC TTA GTA ATG GAA CTG        667
Gln Lys Thr Leu Glu Glu Phe Gln Asp Val Tyr Leu Val Met Glu Leu
     135                140                 145

ATG GAT GCC AAC TTA TGT CAA GTG ATT CAG ATG GAA TTA GAC CAT GAG        715
Met Asp Ala Asn Leu Cys Gln Val Ile Gln Met Glu Leu Asp His Glu
 150                155                 160

CGA ATG TCT TAC CTG CTG TAC CAA ATG TTG TGT GGC ATT AAG CAC CTC        763
Arg Met Ser Tyr Leu Leu Tyr Gln Met Leu Cys Gly Ile Lys His Leu
165                 170                 175                 180

CAT TCT GCT GGA ATT ATT CAC AGG GAT TTA AAA CCA AGT AAC ATT GTA        811
His Ser Ala Gly Ile Ile His Arg Asp Leu Lys Pro Ser Asn Ile Val
             185                190                 195

GTC AAG TCT GAT TGC ACA TTG AAA ATC CTG GAC TTT GGA CTG GCC AGG        859
Val Lys Ser Asp Cys Thr Leu Lys Ile Leu Asp Phe Gly Leu Ala Arg
         200                205                 210

ACA GCA GGC ACA AGC TTC ATG ATG ACT CCA TAT GTG GTG ACA CGT TAT        907
Thr Ala Gly Thr Ser Phe Met Met Thr Pro Tyr Val Val Thr Arg Tyr
     215                220                 225

TAC AGA GCC CCT GAG GTC ATC CTG GGG ATG GGC TAC AAG GAG AAC GTG        955
Tyr Arg Ala Pro Glu Val Ile Leu Gly Met Gly Tyr Lys Glu Asn Val
```

```
                230                 235                 240
GAT ATA TGG TCT GTG GGA TGC ATT ATG GGA GAA ATG GTT CGC CAC AA         1003
Asp Ile Trp Ser Val Gly Cys Ile Met Gly Glu Met Val Arg His Lys
245                 250                 255                 260

ATC CTC TTT CCA GGA AGG GAC TAT ATT GAC CAG TGG AAT AAG GTA AT         1051
Ile Leu Phe Pro Gly Arg Asp Tyr Ile Asp Gln Trp Asn Lys Val Ile
                265                 270                 275

GAA CAA CTA GGA ACA CCA TGT CCA GAA TTC ATG AAG AAA TTG CAA CC         1099
Glu Gln Leu Gly Thr Pro Cys Pro Glu Phe Met Lys Lys Leu Gln Pro
            280                 285                 290

ACA GTA AGA AAC TAT GTG GAG AAT CGG CCC AAG TAT GCG GGA CTC AC         1147
Thr Val Arg Asn Tyr Val Glu Asn Arg Pro Lys Tyr Ala Gly Leu Thr
        295                 300                 305

TTC CCC AAA CTC TTC CCA GAT TCC CTC TTC CCA GCG GAC TCC GAG CA         1195
Phe Pro Lys Leu Phe Pro Asp Ser Leu Phe Pro Ala Asp Ser Glu His
    310                 315                 320

AAT AAA CTC AAA GCC AGC CAA GCC AGG GAC TTG TTG TCA AAG ATG CT         1243
Asn Lys Leu Lys Ala Ser Gln Ala Arg Asp Leu Leu Ser Lys Met Leu
325                 330                 335                 340

GTG ATT GAC CCA GCA AAA AGA ATA TCA GTG GAC GAC GCC TTA CAG CA         1291
Val Ile Asp Pro Ala Lys Arg Ile Ser Val Asp Asp Ala Leu Gln His
                345                 350                 355

CCC TAC ATC AAC GTC TGG TAT GAC CCA GCC GAA GTG GAG GCG CCT CC         1339
Pro Tyr Ile Asn Val Trp Tyr Asp Pro Ala Glu Val Glu Ala Pro Pro
            360                 365                 370

CCT CAG ATA TAT GAC AAG CAG TTG GAT GAA AGA GAA CAC ACA ATT GA         1387
Pro Gln Ile Tyr Asp Lys Gln Leu Asp Glu Arg Glu His Thr Ile Glu
        375                 380                 385

GAA TGG AAA GAA CTT ATC TAC AAG GAA GTA ATG AAT TCA GAA GAA AA         1435
Glu Trp Lys Glu Leu Ile Tyr Lys Glu Val Met Asn Ser Glu Glu Lys
    390                 395                 400

ACT AAA AAT GGT GTA GTA AAA GGA CAG CCT TCT CCT TCA GCA CAG GT         1483
Thr Lys Asn Gly Val Val Lys Gly Gln Pro Ser Pro Ser Ala Gln Val
405                 410                 415                 420

CAG CAG TGAACAGCAG TGAGAGTCTC CCTCCATCCT CGTCTGTCAA TGACATCTCC         1539
Gln Gln

TCCATGTCCA CCGACCAGAC CCTGGCATCT GACACTGACA GCAGCCTGGA AGCCTCG         1599

GGACCCCTGG GTTGTTGCAG GTGACTAGCC GCCTGCCTGC GAAACCCAGC GTTCTTC         1659

AGATGATGTG ATGGAACACA CACACGCA GACACACACA CACACACAAA TGCAGAC           1719

CAACATCAAG AAAACAGCAA GGGAGAGAAT CCAAGCCTAA AATTAAATAA ATCTTTC         1779

CTGCTTCTTC CCCAGGGTTC TGTATTGCAG CTAAGCTCAA ATGTATATTT AACTTCT         1839

TGCTCTTGCT TTGGTCTTCT TCCAATGATG CTTACTACAG AAAGCAAATC AGACACA         1899

AGAGAAGCCT TTTCCATAAA GTGTAATTTT AATGGCTGCA AAACCGGCAA CCTGTAA         1959

CCCTTTTAAA TGGCATGACA AGGTGTGCAG TGGCCCCATC CAGCATGTGT GTGTCTC         2019

CTTGCATCTA CCTGCTCCTT GGCCTAGTCA GATGGATGTA GATACAGATC CGCATGT         2079

TGTATTCATA CAGCACTACT TACTTAGAGA TGCTACTCTC AGTGTCCTCA GGGCTCT         2139

AAGACATAAT GCACTGGGGT ACCACATGGT CCATTTCATG TGATCTATTA CTCTGAC         2199

AACCCATCTG TAATATATTG CCAGTATATA AGCTGTTTAG TTTGTTAATT GATTAAA         2259

TATGTCTTAT AAGAAAACAT GTAAAGGGGG AATATATTGG GGGAGTGAGC TCTCTCA         2319

CCTTGAAGAT GTAGCTTCCA AATTTGAATG GATTAAATGG CACCTGTATA CCA            2372
```

(2) INFORMATION FOR SEQ ID NO: 8:

(i) SEQUENCE CHARACTERISTICS:
    (A) LENGTH: 422 amino acids
    (B) TYPE: amino acid
    (D) TOPOLOGY: linear (ii) MOLECULE TYPE: protein (v) FRAGMENT TYPE: internal (xi) SEQUENCE DESCRIPTION: SEQ ID NO: 8:

```
Met Ser Leu His Phe Leu Tyr Tyr Cys Ser Glu Pro Thr Leu Asp Val
 1               5                  10                  15

Lys Ile Ala Phe Cys Gln Gly Phe Asp Lys Gln Val Asp Val Ser Tyr
            20                  25                  30

Ile Ala Lys His Tyr Asn Met Ser Lys Ser Val Asp Asn Gln Phe
            35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
 65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
                100                 105                 110

Val Leu Met Lys Cys Val Asn His Lys Asn Ile Ile Ser Leu Leu Asn
            115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
    195                 200                 205

Gly Leu Ala Arg Thr Ala Gly Thr Ser Phe Met Met Thr Pro Tyr Val
210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
    275                 280                 285

Lys Leu Gln Pro Thr Val Arg Asn Tyr Val Glu Asn Arg Pro Lys Tyr
290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
```

-continued

```
                355                 360                 365
Glu Ala Pro Pro Pro Gln Ile Tyr Asp Lys Gln Leu Asp Glu Arg Glu
        370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Ala Gln Val Gln Gln
            420
```

(2) INFORMATION FOR SEQ ID NO: 9:

(i) SEQUENCE CHARACTERISTICS:
        (A) LENGTH: 1975 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: Coding Sequence
        (B) LOCATION: 364...1641

(xi) SEQUENCE DESCRIPTION: SEQ ID NO: 9:

```
CCCTCCTTAT TCCGGTTTGG AATGTGGCTA ATGAAAGCCC AGTAGGAGGA TTTCTGGGG         60

AAACAGGTGG ACCAGGATCC TGGTTCTCAG GCACGGAATG GCTATTGTGA GAGCGCCA         120

AGCAGGACCA TCGCAGATCT TGGTTATGGC TGCTCACGCA AGAGGCTGTT GATGTAGA         180

CCCTTTCCCG TAGATGAGAA ATCACACGAG CAGTGGTATT TATGAGCCTC CATTTCTT         240

ACTACTGCAG TGAACCAACC TTGGATGTGA AAATTGCCTT TTGTCAGGTG TGTGTTCC         300

ACAGGTAAAA CAAAGGGATT CGACAAACAC GTGGATGTGT CTTCTGTTGT CAAACATT         360

AAC ATG AGC AAA AGC AAG GTA GAT AAC CAG TTC TAC AGT GTG GAA GTG        408
    Met Ser Lys Ser Lys Val Asp Asn Gln Phe Tyr Ser Val Glu Val
     1               5                  10                  15

GGA GAC TCA ACC TTC ACA GTT CTA AAG CGC TAC CAG AAC CTG AAG CCG        456
Gly Asp Ser Thr Phe Thr Val Leu Lys Arg Tyr Gln Asn Leu Lys Pro
                20                  25                  30

ATC GGC TCT GGG GCT CAG GGA ATA GTT TGT GCT GCG TAT GAC GCT GTC        504
Ile Gly Ser Gly Ala Gln Gly Ile Val Cys Ala Ala Tyr Asp Ala Val
            35                  40                  45

CTC GAC AGA AAT GTG GCC ATT AAG AAG CTC AGC AGA CCC TTC CAG AAC        552
Leu Asp Arg Asn Val Ala Ile Lys Lys Leu Ser Arg Pro Phe Gln Asn
        50                  55                  60

CAA ACT CAT GCC AAG AGG GCT TAC CGG GAG CTG GTC CTC ATG AAG TGT        600
Gln Thr His Ala Lys Arg Ala Tyr Arg Glu Leu Val Leu Met Lys Cys
    65                  70                  75

GTG AAC CAT AAA AAC ATT ATT AGC TTA TTA AAT GTC TTT ACA CCC CAG        648
Val Asn His Lys Asn Ile Ile Ser Leu Leu Asn Val Phe Thr Pro Gln
80                  85                  90                  95

AAA ACA CTG GAG GAG TTC CAA GAT GTT TAC TTA GTG ATG GAA CTG ATG        696
Lys Thr Leu Glu Glu Phe Gln Asp Val Tyr Leu Val Met Glu Leu Met
                100                 105                 110

GAC GCC AAC TTG TGT CAG GTG ATT CAG ATG GAG CTG GAC CAC GAG CGG        744
Asp Ala Asn Leu Cys Gln Val Ile Gln Met Glu Leu Asp His Glu Arg
            115                 120                 125

ATG TCG TAC TTG CTG TAC CAG ATG CTG TCG GCG ATC AAA CAC CTC CAC        792
Met Ser Tyr Leu Leu Tyr Gln Met Leu Ser Ala Ile Lys His Leu His
        130                 135                 140
```

```
TCC GCT GGG ATC ATC CAC AGG GAC TTA AAA CCC AGT AAC ATC GTA GTC      840
Ser Ala Gly Ile Ile His Arg Asp Leu Lys Pro Ser Asn Ile Val Val
145             150                 155

AAG TCT GAT TGC ACA CTG AAA ATC CTG GAC TTT GGA CTG GCC AGG ACA      888
Lys Ser Asp Cys Thr Leu Lys Ile Leu Asp Phe Gly Leu Ala Arg Thr
160             165                 170                 175

GCG GGC ACA AGC TTC ATG ATG ACT CCG TAT GTG GTG ACG AGA TAT TAC      936
Ala Gly Thr Ser Phe Met Met Thr Pro Tyr Val Val Thr Arg Tyr Tyr
                180                 185                 190

AGA GCC CCC GAG GTC ATC CTG GGC ATG GGC TAC AAG GAG AAC GTG GAC      984
Arg Ala Pro Glu Val Ile Leu Gly Met Gly Tyr Lys Glu Asn Val Asp
                195                 200                 205

ATA TGG TCT GTG GGC TGC ATC ATG GGA GAA ATG GTT CGT CAC AAA AT      1032
Ile Trp Ser Val Gly Cys Ile Met Gly Glu Met Val Arg His Lys Ile
                210                 215                 220

CTC TTT CCC GGA AGG GAC TAT ATT GAC CAG TGG AAC AAA GTC ATA GA      1080
Leu Phe Pro Gly Arg Asp Tyr Ile Asp Gln Trp Asn Lys Val Ile Glu
225                 230                 235

CAG CTA GGA ACT CCG TGT CCA GAA TTC ATG AAG AAA TTG CAG CCC AC      1128
Gln Leu Gly Thr Pro Cys Pro Glu Phe Met Lys Lys Leu Gln Pro Thr
240                 245                 250                 255

GTC AGA AAC TAC GTG GAG AAC CGG CCC AAG TAT GCA GGC CTC ACC TT      1176
Val Arg Asn Tyr Val Glu Asn Arg Pro Lys Tyr Ala Gly Leu Thr Phe
                260                 265                 270

CCC AAG CTC TTT CCA GAT TCC CTC TTC CCA GCG GAT TCC GAG CAC AA      1224
Pro Lys Leu Phe Pro Asp Ser Leu Phe Pro Ala Asp Ser Glu His Asn
                275                 280                 285

AAA CTT AAA GCC AGC CAA GCC AGG GAC TTG TTG TCA AAG ATG TTA GT      1272
Lys Leu Lys Ala Ser Gln Ala Arg Asp Leu Leu Ser Lys Met Leu Val
                290                 295                 300

ATT GAC CCA GCG AAG AGG ATA TCG GTG GAT GAC GCA TTG CAG CAT CC      1320
Ile Asp Pro Ala Lys Arg Ile Ser Val Asp Asp Ala Leu Gln His Pro
305                 310                 315

TAC ATC AAC GTT TGG TAC GAC CCT GCT GAA GTG GAG GCG CCT CCG CC      1368
Tyr Ile Asn Val Trp Tyr Asp Pro Ala Glu Val Glu Ala Pro Pro Pro
320                 325                 330                 335

CAG ATA TAT GAC AAG CAA TTG GAT GAA AGG GAG CAC ACC ATC GAA GA      1416
Gln Ile Tyr Asp Lys Gln Leu Asp Glu Arg Glu His Thr Ile Glu Glu
                340                 345                 350

TGG AAA GAA CTC ATC TAC AAG GAA GTA ATG AAC TCA GAA GAG AAG AC      1464
Trp Lys Glu Leu Ile Tyr Lys Glu Val Met Asn Ser Glu Glu Lys Thr
                355                 360                 365

AAG AAC GGC GTA GTC AAA GGC CAG CCC TCA CCT TCA GGT GCA GCA GT      1512
Lys Asn Gly Val Val Lys Gly Gln Pro Ser Pro Ser Gly Ala Ala Val
                370                 375                 380

AAC AGC AGT GAG AGT CTC CCT CCA TCC TCA TCT GTC AAC GAC ATC TC      1560
Asn Ser Ser Glu Ser Leu Pro Pro Ser Ser Ser Val Asn Asp Ile Ser
385                 390                 395

TCC ATG TCC ACC GAC CAG ACC CTC GCA TCC GAC ACT GAC AGC AGC CT      1608
Ser Met Ser Thr Asp Gln Thr Leu Ala Ser Asp Thr Asp Ser Ser Leu
400                 405                 410                 415

GAA GCC TCG GCG GGA CCG CTG GGT TGT TGC AGG TGACTAGCCG CCTGCCT      1661
Glu Ala Ser Ala Gly Pro Leu Gly Cys Cys Arg
                420                 425

AAACCCAGCG TTCTTCAGGA GATGACGCCA TGATAGAACA CAGCGCACAT GCACACA       1721

AGAGCTTGTA CACACACACA CACACACACA CACGCACACG CACGCACGCA CGCAAGC       1781

CACGCACGCA CAAATGCACT CACGCAATGT CAAGAAAAAA AAAAGTAGCG AGAGAGA       1841

AGAGAGCCAA CGTAAAACTA AGTTAAATCT TTCTGCGTGC TTCTCCAGAG TTCTGTA       1901
```

```
CAGCTGAGCT GAAATGTATA CTTAACTTCT AGTCGCGCTC GCTCGACTTT GGTCTCC      1961

CGGCAGTGCT TACT                                                    1975
```

(2) INFORMATION FOR SEQ ID NO: 10:

(i) SEQUENCE CHARACTERISTICS:
        (A) LENGTH: 426 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 10:

```
Met Ser Lys Ser Lys Val Asp Asn Gln Phe Tyr Ser Val Glu Val Gly
 1               5                  10                  15

Asp Ser Thr Phe Thr Val Leu Lys Arg Tyr Gln Asn Leu Lys Pro Ile
             20                  25                  30

Gly Ser Gly Ala Gln Gly Ile Val Cys Ala Ala Tyr Asp Ala Val Leu
         35                  40                  45

Asp Arg Asn Val Ala Ile Lys Lys Leu Ser Arg Pro Phe Gln Asn Gln
     50                  55                  60

Thr His Ala Lys Arg Ala Tyr Arg Glu Leu Val Leu Met Lys Cys Val
 65                  70                  75                  80

Asn His Lys Asn Ile Ile Ser Leu Leu Asn Val Phe Thr Pro Gln Lys
                 85                  90                  95

Thr Leu Glu Glu Phe Gln Asp Val Tyr Leu Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Ser Ala Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Met Val Arg His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Asn Tyr Val Glu Asn Arg Pro Lys Tyr Ala Gly Leu Thr Phe Pro
            260                 265                 270

Lys Leu Phe Pro Asp Ser Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Pro Ala Lys Arg Ile Ser Val Asp Asp Ala Leu Gln His Pro Tyr
305                 310                 315                 320
```

```
Ile Asn Val Trp Tyr Asp Pro Ala Glu Val Glu Ala Pro Pro Gln
            325                 330             335

Ile Tyr Asp Lys Gln Leu Asp Glu Arg Glu His Thr Ile Glu Glu Trp
            340                 345             350

Lys Glu Leu Ile Tyr Lys Glu Val Met Asn Ser Glu Lys Thr Lys
            355                 360             365

Asn Gly Val Val Lys Gly Gln Pro Ser Pro Ser Gly Ala Ala Val Asn
    370             375             380

Ser Glu Ser Leu Pro Pro Ser Ser Val Asn Asp Ile Ser Ser
385             390             395             400

Met Ser Thr Asp Gln Thr Leu Ala Ser Asp Thr Asp Ser Ser Leu Glu
            405             410             415

Ala Ser Ala Gly Pro Leu Gly Cys Cys Arg
            420             425
```

(2) INFORMATION FOR SEQ ID NO: 11:

(i) SEQUENCE CHARACTERISTICS:
        (A) LENGTH: 2522 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: Coding Sequence
        (B) LOCATION: 310...1575

(xi) SEQUENCE DESCRIPTION: SEQ ID NO: 11:

```
GGGGCTTGAG TGAGCTAAAG ATTGGGTCTT CTTGGAAATC ACCTGTCTGT TATTATTTT        60

AAACAATCGC TACACCTCCA AAGACTCTGC TCCTTACTCC GGTTTGGAAT GTGGCTAA        120

ACTACCCAGT AGGGAGGATT TCTGGGGCAA ACAGCCGGAC CAGGATCCTA GTTCTCAG        180

ACGGAATGGC TATTGTGAGA ACAGCACCAG CAGGATCATC GCAGATCTTG GTTATGGC        240

CTCAGGCAAG ACGCTGTTGA GTTAAGACCC CTTTCCCATA GATGAGAAGC CACAGAAG        300

GTGGTATTT ATG AGC CTC CAT TTC TTA TAC TAC TGC AGT GAA CCA ACC T        351
           Met Ser Leu His Phe Leu Tyr Tyr Cys Ser Glu Pro Thr Leu
               1               5                   10

GAT GTG AAA ATT GCC TTT TGT CAG GGA TTC GAT AAA CAC GTG GAT GTG        399
Asp Val Lys Ile Ala Phe Cys Gln Gly Phe Asp Lys His Val Asp Val
 15                  20                  25                  30

TCA TCT ATT GCC AAA CAT TAC AAC ATG AGC AAA AGC AAG GTG GAC AAC        447
Ser Ser Ile Ala Lys His Tyr Asn Met Ser Lys Ser Lys Val Asp Asn
             35                  40                  45

CAG TTC TAC AGT GTG GAA GTG GGG GAC TCA ACC TTC ACC GTT CTT AAG        495
Gln Phe Tyr Ser Val Glu Val Gly Asp Ser Thr Phe Thr Val Leu Lys
             50                  55                  60

CGC TAC CAG AAC CTG AAG CCA ATT GGC TCT GGG GCT CAG GGA ATA GTC        543
Arg Tyr Gln Asn Leu Lys Pro Ile Gly Ser Gly Ala Gln Gly Ile Val
             65                  70                  75

TGT GCT GCG TAC GAC GCT GTC CTT GAC AGA AAT GTG GCC ATT AAG AAG        591
Cys Ala Ala Tyr Asp Ala Val Leu Asp Arg Asn Val Ala Ile Lys Lys
 80                  85                  90

CTC AGC AGA CCC TTC CAG AAC CAA ACT CAC GCC AAG AGG GCT TAC CGG        639
Leu Ser Arg Pro Phe Gln Asn Gln Thr His Ala Lys Arg Ala Tyr Arg
 95                 100                 105                 110

GAG CTG GTG CTC ATG AAG TGT GTG AAC CAT AAA AAC ATT ATT AGC TTA        687
Glu Leu Val Leu Met Lys Cys Val Asn His Lys Asn Ile Ile Ser Leu
                115                 120                 125
```

-continued

```
TTA AAT GTT TTT ACA CCC CAG AAA ACG CTG GAG GAG TTC CAA GAT GTC      735
Leu Asn Val Phe Thr Pro Gln Lys Thr Leu Glu Glu Phe Gln Asp Val
            130                 135                 140

TAC TTA GTG ATG GAA CTG ATG GAC GCC AAC CTG TGT CAG GTG ATT CAG      783
Tyr Leu Val Met Glu Leu Met Asp Ala Asn Leu Cys Gln Val Ile Gln
            145                 150                 155

ATG GAG CTG GAC CAC GAG CGG ATG TCT TAC TTG CTG TAC CAG ATG CTG      831
Met Glu Leu Asp His Glu Arg Met Ser Tyr Leu Leu Tyr Gln Met Leu
    160                 165                 170

TGT GGC ATC AAG CAC CTC CAC TCC GCT GGG ATC ATC CAC AGG GAC TTA      879
Cys Gly Ile Lys His Leu His Ser Ala Gly Ile Ile His Arg Asp Leu
175                 180                 185                 190

AAA CCC AGT AAC ATT GTA GTC AAG TCT GAT TGC ACA CTG AAA ATC CTC      927
Lys Pro Ser Asn Ile Val Val Lys Ser Asp Cys Thr Leu Lys Ile Leu
                195                 200                 205

GAC TTC GGA CTG GCC AGG ACA GCG GGT ACA AGC TTC ATG ATG ACT CCG      975
Asp Phe Gly Leu Ala Arg Thr Ala Gly Thr Ser Phe Met Met Thr Pro
            210                 215                 220

TAT GTG GTG ACG CGA TAT TAC AGA GCC CCT GAG GTC ATC CTG GGC AT      1023
Tyr Val Val Thr Arg Tyr Tyr Arg Ala Pro Glu Val Ile Leu Gly Met
            225                 230                 235

GGC TAC AAG GAG AAC GTG GAC ATA TGG TCT GTG GGA TGC ATC ATG GG      1071
Gly Tyr Lys Glu Asn Val Asp Ile Trp Ser Val Gly Cys Ile Met Gly
    240                 245                 250

GAA ATG GTT CGC CAC AAA ATC CTC TTT CCC GGA AGG AGC TAT ATT GA      1119
Glu Met Val Arg His Lys Ile Leu Phe Pro Gly Arg Ser Tyr Ile Asp
255                 260                 265                 270

CAG TGG AAC AAA GTC ATC GAG CAG CTA GGA ACT CCG TGT CCA GAG TT      1167
Gln Trp Asn Lys Val Ile Glu Gln Leu Gly Thr Pro Cys Pro Glu Phe
                275                 280                 285

ATG AAG AAA TTG CAG CCC ACA GTC AGA AAC TAC GTG GAG AAT CGG CC      1215
Met Lys Lys Leu Gln Pro Thr Val Arg Asn Tyr Val Glu Asn Arg Pro
            290                 295                 300

AAG TAC GCA GGA CTC ACC TTC CCC AAG CTC TTT CCA GAT TCC CTC TT      1263
Lys Tyr Ala Gly Leu Thr Phe Pro Lys Leu Phe Pro Asp Ser Leu Phe
            305                 310                 315

CCA GCG GAT TCT GAG CAC AAT AAA CTT AAA GCC AGC CAA GCC AGG GA      1311
Pro Ala Asp Ser Glu His Asn Lys Leu Lys Ala Ser Gln Ala Arg Asp
    320                 325                 330

TTG TTG TCT AAG ATG TTA GTG ATT GAC CCA GTG AAG AGG ATA TCG GT      1359
Leu Leu Ser Lys Met Leu Val Ile Asp Pro Val Lys Arg Ile Ser Val
335                 340                 345                 350

GAC GAC GCA CTG CAG CAT CCG TAC ATC AAC GTT TGG TAC GAC CCG GC      1407
Asp Asp Ala Leu Gln His Pro Tyr Ile Asn Val Trp Tyr Asp Pro Ala
                355                 360                 365

GAA GTG GAG GCG CCT CCG CCT CAG ATA TAT GAT AAG CAG CTG GAT GA      1455
Glu Val Glu Ala Pro Pro Pro Gln Ile Tyr Asp Lys Gln Leu Asp Glu
            370                 375                 380

AGG GAG CAC ACC ATC GAA GAA TGG AAA GAA CTT ATC TAC AAG GAG GT      1503
Arg Glu His Thr Ile Glu Glu Trp Lys Glu Leu Ile Tyr Lys Glu Val
            385                 390                 395

ATG AAC TCA GAA GAG AAG ACT AAG AAT GGC GTA GTC AAA AGC CAG CC      1551
Met Asn Ser Glu Glu Lys Thr Lys Asn Gly Val Val Lys Ser Gln Pro
    400                 405                 410

TCG CCT TCA GCA CAG GTG CAG CAG TGAACAGCAG TGAGAGTCTC CCTCCATC      1605
Ser Pro Ser Ala Gln Val Gln Gln
415                 420

CGGCTGTCAA CGACATCTCC TCCATGTCCA CCGACCAGAC CCTCGCATCT GACACTG       1665
```

-continued

```
GCAGCCTGGA GGCCTCGGCG GGACCGTTGG GTTGTTGCAG GTGACTAGCC GCCTGCC        1725

GAAACCCAGC GTTCTTCAGG AGATGACGCG ATAGAACACA GCACACATGC ACACACA        1785

CTTGCTCTCA CACACACTCA GCTTGCTCAC ACACACACAC ACACATACAC ACAAACA        1845

ACTGTCTCTC TCTCACACAC ACACACTGTC ACAACGCACT CACGAAAGGT CAAGAAA        1905

ATAACAATAG AGAGATCCAA CATAAAATTA AGTTAAATTT TTCTGCGTGC TTCTCCA        1965

TTCTGTATCA CAGCTGAGCT GAAATGTATA CTTAACTTCT AGTTGCGCTC GCTTTGG        2025

CCCTCCAGCA GTGCTTACTA CACAAGACAA ATCAGACACA ATTAGAGAAA CCTTTCC        2085

AAGTGTAACT TAAGTGGCTG CAGAACCAGC AACCTGTAAC TGCCCTTCAA ATGGCAT        2145

GAGGTGGGCA CGGGTCCCGC CCAGCATGTG TGTGTCTCTA TCTCGCGTCT ACCTGCT        2205

CCGGCCTAGT CAGATGGATG TAGATACAGA TCCCGCATGT GTCTGTATTC AAACAGC        2265

TAGAGATGCT CCTGTCAGTG TCCTCCAGGC TCCACCAAGA CACACACCGG GGTACCA        2325

GGTCCATTTC ATGTGATCTA TTACTCTGAC ATAAATCCAT CTGTAATATA TTGCCAG        2385

ATAAGCTGTT TAGTTTGTTA ATTGCTTAAG CTGTATGTCT TATAAGAGAC TATGTAA        2445

GGGAAAATGG AGGCGTGAAC TCTCAGACCC TTGAAGATGT AGCTTCCGAA TTTGACC        2505

AAATGGCACC GTATACC                                                   2522
```

(2) INFORMATION FOR SEQ ID NO: 12:

(i) SEQUENCE CHARACTERISTICS:
        (A) LENGTH: 422 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 12:

```
Met Ser Leu His Phe Leu Tyr Tyr Cys Ser Glu Pro Thr Leu Asp Val
 1               5                  10                  15

Lys Ile Ala Phe Cys Gln Gly Phe Asp Lys His Val Asp Val Ser Ser
            20                  25                  30

Ile Ala Lys His Tyr Asn Met Ser Lys Ser Lys Val Asp Asn Gln Phe
        35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190
```

```
Ser Asn Ile Val Val Lys Ser Asp Cys Thr Leu Lys Ile Leu Asp Phe
        195                 200                 205
Gly Leu Ala Arg Thr Ala Gly Thr Ser Phe Met Met Thr Pro Tyr Val
        210                 215                 220
Val Thr Arg Tyr Tyr Arg Ala Pro Glu Val Ile Leu Gly Met Gly Tyr
225                 230                 235                 240
Lys Glu Asn Val Asp Ile Trp Ser Val Gly Cys Ile Met Gly Glu Met
                245                 250                 255
Val Arg His Lys Ile Leu Phe Pro Gly Arg Ser Tyr Ile Asp Gln Trp
            260                 265                 270
Asn Lys Val Ile Glu Gln Leu Gly Thr Pro Cys Pro Glu Phe Met Lys
        275                 280                 285
Lys Leu Gln Pro Thr Val Arg Asn Tyr Val Glu Asn Arg Pro Lys Tyr
        290                 295                 300
Ala Gly Leu Thr Phe Pro Lys Leu Phe Pro Asp Ser Leu Phe Pro Ala
305                 310                 315                 320
Asp Ser Glu His Asn Lys Leu Lys Ala Ser Gln Ala Arg Asp Leu Leu
                325                 330                 335
Ser Lys Met Leu Val Ile Asp Pro Val Lys Arg Ile Ser Val Asp Asp
            340                 345                 350
Ala Leu Gln His Pro Tyr Ile Asn Val Trp Tyr Asp Pro Ala Glu Val
        355                 360                 365
Glu Ala Pro Pro Pro Gln Ile Tyr Asp Lys Gln Leu Asp Glu Arg Glu
370                 375                 380
His Thr Ile Glu Glu Trp Lys Glu Leu Ile Tyr Lys Glu Val Met Asn
385                 390                 395                 400
Ser Glu Glu Lys Thr Lys Asn Gly Val Val Lys Ser Gln Pro Ser Pro
                405                 410                 415
Ser Ala Gln Val Gln Gln
            420

(2) INFORMATION FOR SEQ ID NO: 13:

(i) SEQUENCE CHARACTERISTICS:
        (A) LENGTH: 2347 base pairs
        (B) TYPE: nucleic acid
        (C) STRANDEDNESS: double
        (D) TOPOLOGY: linear (ii) MOLECULE TYPE: DNA (ix) FEATURE:
        (A) NAME/KEY: Coding Sequence
        (B) LOCATION: 615...1616

(xi) SEQUENCE DESCRIPTION: SEQ ID NO: 13:

AGCAACTTTC CTGACCCAGA GGACCGGTAA CAAGTGGCCG GGAGCAACTT TTGCAAATC        60

CTTCTGCGCC TTAAGGCTGC CACCGAGACT GTAAAGAAAA GGAGAAGAGG AACCTATA       120

CATACCAGTT CGCACAGGCC TAAGTTGGGC GAGGCCTAGC CGCGGCTGCC TAGCGTCC       180

CCCCCCCTCA CAGCGGAGGA GGGGACAGTT GTTGGAGGCC GGGCGGCAGA CCCGATCG       240

GGCCTCCACC GAGAATTCCG TGACGACTGG TCAGCACCGC CGGAGAGCCG CTGTTGCT       300

GACTGGTCTG CGGGCTCCAA GGAACCGCTG CTCCCCGAGA GCGCTCCGTG AGTGACCG       360

ACTTTTCAAA GCTCGGCATC GCGCGGAGTC CTACCAACGT GAGTGCTAGC GGAGTCTT       420

CCCTGCGCTC CCTGGAGCGA ACTGGGGAGG AGGGCTCAGG GGAAGCACT GCCGTCTG        480
```

-continued

```
GCGCACGCTC TAAACAAACT TGTTACAGA AGCAGGGACG CGCGGGTATC CCCCCGCT           540

CCGGCGCGCT GTTGCGGCCC CGAAACTTCT GCGCACAGCC CAGGCTAACC CCGCGTGA           600

TGACGGACCG TTCT ATG ACT GCA AAG ATG GAA ACG ACC TTC TAC GAC GAT          650
              Met Thr Ala Lys Met Glu Thr Thr Phe Tyr Asp Asp
                1               5                      10

GCC CTC AAC GCC TCG TTC CTC CAG TCC GAG AGC GGT GCC TAC GGC TAC          698
Ala Leu Asn Ala Ser Phe Leu Gln Ser Glu Ser Gly Ala Tyr Gly Tyr
            15                  20                  25

AGT AAC CCT AAG ATC CTA AAA CAG AGC ATG ACC TTG AAC CTG GCC GAC          746
Ser Asn Pro Lys Ile Leu Lys Gln Ser Met Thr Leu Asn Leu Ala Asp
        30                  35                  40

CCG GTG GGC AGT CTG AAG CCG CAC CTC CGC GCC AAG AAC TCG GAC CTT          794
Pro Val Gly Ser Leu Lys Pro His Leu Arg Ala Lys Asn Ser Asp Leu
45                  50                  55                  60

CTC ACG TCG CCC GAC GTC GGG CTG CTC AAG CTG GCG TCG CCG GAG CTG          842
Leu Thr Ser Pro Asp Val Gly Leu Leu Lys Leu Ala Ser Pro Glu Leu
                65                  70                  75

GAG CGC CTG ATC ATC CAG TCC AGC AAT GGG CAC ATC ACC ACT ACA CCG          890
Glu Arg Leu Ile Ile Gln Ser Ser Asn Gly His Ile Thr Thr Thr Pro
            80                  85                  90

ACC CCC ACC CAG TTC TTG TGC CCC AAG AAC GTG ACC GAC GAG CAG GAG          938
Thr Pro Thr Gln Phe Leu Cys Pro Lys Asn Val Thr Asp Glu Gln Glu
        95                  100                 105

GGC TTC GCC GAG GGC TTC GTG CGC GCC CTG GCT GAA CTG CAT AGC CAG          986
Gly Phe Ala Glu Gly Phe Val Arg Ala Leu Ala Glu Leu His Ser Gln
110                 115                 120

AAC ACG CTT CCC AGT GTC ACC TCC GCG GCA CAG CCG GTC AGC GGG GC          1034
Asn Thr Leu Pro Ser Val Thr Ser Ala Ala Gln Pro Val Ser Gly Ala
125                 130                 135                 140

GGC ATG GTG GCT CCC GCG GTG GCC TCA GTA GCA GGC GCT GGC GGC GG          1082
Gly Met Val Ala Pro Ala Val Ala Ser Val Ala Gly Ala Gly Gly Gly
                145                 150                 155

GGT GGC TAC AGC GCC AGC CTG CAC AGT GAG CCT CCG GTC TAC GCC AA          1130
Gly Gly Tyr Ser Ala Ser Leu His Ser Glu Pro Pro Val Tyr Ala Asn
            160                 165                 170

CTC AGC AAC TTC AAC CCG GGT GCG CTG AGC AGC GGC GGT GGG GCG CC          1178
Leu Ser Asn Phe Asn Pro Gly Ala Leu Ser Ser Gly Gly Gly Ala Pro
        175                 180                 185

TCC TAT GGC GCG GCC GGG CTG GCC TTT CCC TCG CAG CCG CAG CAG CA          1226
Ser Tyr Gly Ala Ala Gly Leu Ala Phe Pro Ser Gln Pro Gln Gln Gln
190                 195                 200

CAG CAG CCG CCT CAG CCG CCG CAC CAC TTG CCC CAA CAG ATC CCG GT          1274
Gln Gln Pro Pro Gln Pro Pro His His Leu Pro Gln Gln Ile Pro Val
205                 210                 215                 220

CAG CAC CCG CGG CTG CAA GCC CTG AAG GAA GAG CCG CAG ACC GTG CC          1322
Gln His Pro Arg Leu Gln Ala Leu Lys Glu Glu Pro Gln Thr Val Pro
                225                 230                 235

GAG ATG CCG GGA GAG ACG CCG CCC CTG TCC CCT ATC GAC ATG GAG TC          1370
Glu Met Pro Gly Glu Thr Pro Pro Leu Ser Pro Ile Asp Met Glu Ser
            240                 245                 250

CAG GAG CGG ATC AAG GCA GAG AGG AAG CGC ATG AGG AAC CGC ATT GC          1418
Gln Glu Arg Ile Lys Ala Glu Arg Lys Arg Met Arg Asn Arg Ile Ala
        255                 260                 265

GCC TCC AAG TGC CGG AAA AGG AAG CTG GAG CGG ATC GCT CGG CTA GA          1466
Ala Ser Lys Cys Arg Lys Arg Lys Leu Glu Arg Ile Ala Arg Leu Glu
270                 275                 280

GAA AAA GTG AAA ACC TTG AAA GCG CAA AAC TCC GAG CTG GCA TCC AC          1514
Glu Lys Val Lys Thr Leu Lys Ala Gln Asn Ser Glu Leu Ala Ser Thr
285                 290                 295                 300
```

-continued

```
GCC AAC ATG CTC AGG GAA CAG GTG GCA CAG CTT AAG CAG AAA GTC AT      1562
Ala Asn Met Leu Arg Glu Gln Val Ala Gln Leu Lys Gln Lys Val Met
            305                 310                 315

AAC CAC GTT AAC AGT GGG TGC CAA CTC ATG CTA ACG CAG CAG TTG CA      1610
Asn His Val Asn Ser Gly Cys Gln Leu Met Leu Thr Gln Gln Leu Gln
            320                 325                 330

ACG TTT TGAGAACAGA CTGTCAGGGC TGAGGGGCAA TGGAAGAAAA AAAATAACAG      1666
Thr Phe
AGACAAACTT GAGAACTTGA CTGGTTGCGA CAGAGAAAAA AAAAGTGTCC GAGTACT      1726

GCCAAGGGTA CACAAGATGG ACTGGGTTCG GACTGACGGC GCCCCCAGTG TGCTCTG      1786

TGGGAAGGAC GTGGCGCGCC TGGCTTTGGC GTGGAGCCAG AGAGCAGGCC TATTGGC      1846

CAGACTTTGC GGAGCGCTGT GCCGCGCGCG ACCAGAACGA TGGACTTTTC GTTAACA      1906

ACCAAGAACT GCATGGACCT AACATTCGAT CTCATTCAGT ATTAAAGGGG GGTGGGA      1966

GTTACAAACT GCAATAGAGA CTGTAGATTG CTTCTGTAGT GCTCCTTAAC ACAAAGC      2026

GAGGGCTGGG AAGGGGGGGA GGCTTGTAAG TGCCAGGCTA GACTGCAGAT GAACTCC      2086

GGCCTGCCTC TCTCAACTGT GTATGTACAT ATATATTTTT TTTTAATTTG ATGAAAG      2146

ATTACTGTCA ATAAACAGCT TCCTGCCTTT GTAAGTTATT CCATGTTTGT TTGTTTG      2206

GTCCTGCCCA GTGTTTGTAA ATAAGAGATT TGAAGCATTC TGAGTTTACC ATTTGTA      2266

AAGTATATAA TTTTTTTATG TTTTGTTTCT GAAAATTTCC AGAAAGGATA TTTAAGA      2326

TACAATAAAC TATTGAAAAG T                                              2347
```

(2) INFORMATION FOR SEQ ID NO: 14:

(i) SEQUENCE CHARACTERISTICS:
        (A) LENGTH: 334 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO: 14:

```
Met Thr Ala Lys Met Glu Thr Thr Phe Tyr Asp Asp Ala Leu Asn Ala
 1               5                  10                  15

Ser Phe Leu Gln Ser Glu Ser Gly Ala Tyr Gly Tyr Ser Asn Pro Lys
            20                  25                  30

Ile Leu Lys Gln Ser Met Thr Leu Asn Leu Ala Asp Pro Val Gly Ser
            35                  40                  45

Leu Lys Pro His Leu Arg Ala Lys Asn Ser Asp Leu Leu Thr Ser Pro
     50                  55                  60

Asp Val Gly Leu Leu Lys Leu Ala Ser Pro Glu Leu Glu Arg Leu Ile
 65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
            115                 120                 125

Ser Val Thr Ser Ala Ala Gln Pro Val Ser Gly Ala Gly Met Val Ala
            130                 135                 140

Pro Ala Val Ala Ser Val Ala Gly Ala Gly Gly Gly Gly Tyr Ser
145                 150                 155                 160
```

```
Ala Ser Leu His Ser Glu Pro Pro Val Tyr Ala Asn Leu Ser Asn Phe
            165                 170                 175
Asn Pro Gly Ala Leu Ser Ser Gly Gly Ala Pro Ser Tyr Gly Ala
        180                 185                 190
Ala Gly Leu Ala Phe Pro Ser Gln Pro Gln Gln Gln Gln Pro Pro
        195                 200                 205
Gln Pro Pro His His Leu Pro Gln Gln Ile Pro Val Gln His Pro Arg
210                 215                 220
Leu Gln Ala Leu Lys Glu Glu Pro Gln Thr Val Pro Glu Met Pro Gly
225                 230                 235                 240
Glu Thr Pro Pro Leu Ser Pro Ile Asp Met Glu Ser Gln Glu Arg Ile
                245                 250                 255
Lys Ala Glu Arg Lys Arg Met Arg Asn Arg Ile Ala Ala Ser Lys Cys
            260                 265                 270
Arg Lys Arg Lys Leu Glu Arg Ile Ala Arg Leu Glu Glu Lys Val Lys
            275                 280                 285
Thr Leu Lys Ala Gln Asn Ser Glu Leu Ala Ser Thr Ala Asn Met Leu
290                 295                 300
Arg Glu Gln Val Ala Gln Leu Lys Gln Lys Val Met Asn His Val Asn
305                 310                 315                 320
Ser Gly Cys Gln Leu Met Leu Thr Gln Gln Leu Gln Thr Phe
                325                 330
```

(2) INFORMATION FOR SEQ ID NO: 15:

(i) SEQUENCE CHARACTERISTICS:
        (A) LENGTH: 3967 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 15:

```
ATACCAGAGA CTCAAAAAAA AAAAAAAAGT TCCAGATTGC TGGACAATGA CCCGGGTCT      60
ATCCCTTGAC CCTGGGAACC GGGTCCACAT TGAATCAGGT GCGAATGTTC GCTCGCCT     120
TCTGCCTTTC CCGCCTCCCC TCCCCCGGCC GCGGCCCCGG TTCCCCCCCT GCGCTGCA     180
CTCAGAGTTG GCTGCAGCCG GCGAGCTGTT CCCGTCAATC CCTCCCTCCT TTACACAG     240
TGTCCATATT AGGACATCTG CGTCAGCAGG TTTCCACGGC CGGTCCCTGT TGTTCTGG     300
GGGGGACCAT CTCCGAAATC CTACACGCGG AAGGTCTAGG AGACCCCCTA AGATCCCA     360
TGTGAACACT CATAGGTGAA AGATGTATGC CAAGACGGGG GTTGAAAGCC TGGGGCGT     420
AGTTGACGAC AGAGCGCCCG CAGAGGGCCT TGGGGCGCGC TTCCCCCCCC TTCCAGTT     480
GCCCAGTGAC GTAGGAAGTC CATCCATTCA CAGCGCTTCT ATAAAGGCGC CAGCTGAG     540
GCCTACTACT CCAACCGCGA CTGCAGCGAG CAACTGAGAA GACTGGATAG AGCCGGCG     600
TCCGCGAACG AGCAGTGACC GCGCTCCCAC CCAGCTCTGC TCTGCAGCTC CCACCAGT     660
CTACCCCTGG ACCCCTTGCC GGGCTTTCCC CAAACTTCGA CCATGATGTT CTCGGGTT     720
AACGCCGACT ACGAGGCGTC ATCCTCCCGC TGCAGTAGCG CCTCCCCGGC CGGGGACA     780
CTTTCCTACT ACCATTCCCC AGCCGACTCC TTCTCCAGCA TGGGCTCTCC TGTCAACA     840
CAGGTGAGTT TGGCTTTGTG TAGCCGCCAG GTCCGCGCTG AGGGTCGCCG TGGAGGAG     900
ACTGGGGTGT GACTCGCAGG GGCGGGGGGG TCTTCCTTTT TCGCTCTGGA GGGAGACT     960
CGCGGTCAGA GCAGCCTTAG CCTGGGAACC CAGGACTTGT CTGAGCGCGT GCACACT     1020
```

-continued

```
CATAGTAAGA CTTAGTGACC CCTTCCCGCG CGGCAGGTTT ATTCTGAGTG GCCTGCC      1080
ATTCTTCTCT CGGCCGACTT GTTTCTGAGA TCAGCCGGGG CCAACAAGTC TCGAGCA      1140
AGTCGCTAAC TAGAGTTTGG GAGGCGGCAA ACCGCGGCAA TCCCCCCTCC CGGGGCA      1200
TGGAGCAGGG AGGAGGGAGG AGGGAGGAGG GTGCTGCGGG CGGGTGTGTA AGGCAGT      1260
ATTGATAAAA AGCGAGTTCA TTCTGGAGAC TCCGGAGCAG CGCCTGCGTC AGCGCAG      1320
TCAGGGATAT TTATAACAAA CCCCCTTTCG AGCGAGTGAT GCCGAAGGGA TAACGGG      1380
GCAGCAGTAG GATGGAGGAG AAAGGCTGCG CTGCGGAATT CAAGGGAGGA TATTGGG      1440
GCTTTTATCT CCGATGAGGT GCATACAGGA AGACATAAGC AGTCTCTGAC CGGAATG      1500
CTCTCTCCCT GCTTCATGCG ACACTAGGGC CACTTGCTCC ACCTGTGTCT GGAACCT      1560
CGCTCACCTC CGCTTTCCTC TTTTTGTTTT GTTTCAGGAC TTTTGCGCAG ATCTGTC      1620
CTCTAGTGCC AACTTTATCC CCACGGTGAC AGCCATCTCC ACCAGCCCAG ACCTGCA      1680
GCTGGTGCAG CCCACTCTGG TCTCCTCCGT GGCCCCATCG CAGACCAGAG CGCCCCA      1740
TTACGGACTC CCCACCCAGT CTGCTGGGGC TTACGCCAGA GCGGGAATGG TGAAGAC      1800
GTCAGGAGGC AGAGCGCAGA GCATCGGCAG AAGGGGCAAA GTAGAGCAGG TGAGCAG      1860
TTCTGGACCT TTGTGGGCTG GGGGGGGGGG GGGGGCGGA GACTGACGCA CAGACCA      1920
AACAGAGAAG GGACGCTACT GACTGCACTT CCTGACCAGG AGCTGTGGCT GCTAGCC      1980
TCCCTCCCTT GTCAGATTTT GACAGTTGGA CCCAAGACAA ACTCTAGACA GTTTCCC      2040
CAGCTTCCTA CTTCATTCTC TAGCCGGGGA GCTTCTTTGT TCCCCTGCTA AAGATCT      2100
TTTAAATGCA AATCACACTC TGCCTGCCAA CTGCAGGTTA GAAAAACTGC TTCACCG      2160
GGTGCGGGTG CTGTAGGAGC CAGTTTCACT GGGGTGACTG AATGGAGGTG ACACTAG      2220
ACCTTAACTG AATGTTGGTC CTTTTCTTCT ATAGCTATCT CCTGAAGAGG AAGAGAA      2280
GAGAATCCGA AGGGAACGGA ATAAGATGGC TGCAGCCAAG TGCCGGAATC GGAGGAG      2340
GCTGACAGAT ACACTCCAAG CGGTAGGTTG AACCAGCTGC TGCTCCTGAA ACTTTAT      2400
AGTTGGAGCT TGGGACTATG GGCGCAGGGT CCTTGAGCAT GCCCGTGTCT TATGCTT      2460
TATATCTCTC CCTATGCAGG AGACAGATCA ACTTGAAGAT GAGAAGTCTG CGTTGCA      2520
TGAGATTGCC AATCTGCTGA AAGAGAAGGA AAAACTGGAG TTTATTTTGG CAGCCCA      2580
ACCTGCCTGC AAGATCCCCG ATGACCTTGG CTTCCCAGAG GAGATGTCTG TGGCCTC      2640
GGATTTGACT GGAGGTCTGC CTGAGGCTTC CACCCCAGAG TCTGAGGAGG CCTTCAC      2700
GCCCCTTCTC AACGACCCTG AGCCCAAGCC ATCCTTGGAG CCAGTCAAGA GCATCAG      2760
CGTGGAGCTG AAGGCAGAAC CCTTTGATGA CTTCTTGTTT CCGGCATCAT CTAGGCC      2820
TGGCTCAGAG ACCTCCCGCT CTGTGCCAGA TGTGGACCTG TCCGGTTCCT TCTATGC      2880
AGACTGGGAG CCTCTGCACA GCAATTCCTT GGGGATGGGG CCCATGGTCA CAGAGCT      2940
GCCCCTGTGT ACTCCCGTGG TCACCTGTAC TCCGGGCTGC ACTACTTACA CGTCTTC      3000
TGTCTTCACC TACCCTGAAG CTGACTCCTT CCCAAGCTGT GCCGCTGCCC ACCGAAA      3060
CAGCAGCAGC AACGAGCCCT CCTCCGACTC CCTGAGCTCA CCCACGCTGC TGGCCCT      3120
AGCAGTCAGA GAAGGCAAGG CAGCCGGCAT CCAGACGTGC CACTGCCCGA GCTGGTG      3180
TACAGAGAGG AGAAACACGT CTTCCCTCGA AGGTTCCCGT CGACCTAGGG AGGACCT      3240
CTGTTCGTGA ACACACCAG GCTGTGGGCC TCAGGACTT GCAAGCATCC ACATCTG       3300
TCCAGTCCTC ACCTCTTCCA GAGATGTAGC AAAAACAAAA CAAAACAAAA CAAAAAA     3360
```

```
CATGGAGTGT GTTGTTCCTA GTGACACCTG AGAGCTGGTA GTTAGTAGAG CATGTGA      3420

AAGGCCTGGT CTGTGTCTCT TTTCTCTTTC TCCTTAGTTT TCTCATAGCA CTAACTA      3480

TGTTGGGTTC ATTATTGGAA TTAACCTGGT GCTGGATTGT ATCTAGTGCA GCTGATT      3540

ACAATACCTA CTGTGTTCCT GGCAATAGCG TGTTCCAATT AGAAACGACC AATATTA      3600

TAAGAAAAGA TAGGACTTTA TTTTCCAGTA GATAGAAATC AATAGCTATA TCCATGT      3660

GTAGTCCTTC AGCGTCAATG TTCATTGTCA TGTTACTGAT CATGCATTGT CGAGGTG      3720

TGAATGTTCT GACATTAACA GTTTTCCATG AAAACGTTTT TATTGTGTTT TCAATTT      3780

TATTAAGATG GATTCTCAGA TATTTATATT TTTATTTTAT TTTTTTCTAC CCTGAGG      3840

TTCGACATGT GGAAAGTGAA TTTGAATGAA AAATTTTAAG CATTGTTTGC TTATTGT      3900

AGGACATTGT CAATAAAAGC ATTTAAGTTG AATGCGACCA CCTTCTTGCT CTCTTTA      3960

TCAGTTT                                                              3967
```

(2) INFORMATION FOR SEQ ID NO: 16:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Met Phe Ser Gly Phe Asn Ala Asp Tyr Glu Ala Ser Ser Ser Arg
  1               5                  10                  15

Cys Ser Ser Ala Ser Pro Ala Gly Asp Ser Leu Ser Tyr Tyr His Ser
                 20                  25                  30

Pro Ala Asp Ser Phe Ser Ser Met Gly Ser Pro Val Asn Thr Gln Asp
             35                  40                  45

Phe Cys Ala Asp Leu Ser Val Ser Ser Ala Asn Phe Ile Pro Thr Val
         50                  55                  60

Thr Ala Ile Ser Thr Ser Pro Asp Leu Gln Trp Leu Val Gln Pro Thr
 65                  70                  75                  80

Leu Val Ser Ser Val Ala Pro Ser Gln Thr Arg Ala Pro His Pro Tyr
                 85                  90                  95

Gly Leu Pro Thr Gln Ser Ala Gly Ala Tyr Ala Arg Ala Gly Met Val
            100                 105                 110

Lys Thr Val Ser Gly Gly Arg Ala Gln Ser Ile Gly Arg Arg Gly Lys
            115                 120                 125

Val Glu Gln Leu Ser Pro Glu Glu Glu Lys Arg Arg Ile Arg Arg
            130                 135                 140

Glu Arg Asn Lys Met Ala Ala Ala Lys Cys Arg Asn Arg Arg Arg Glu
145                 150                 155                 160

Leu Thr Asp Thr Leu Gln Ala Glu Thr Asp Gln Leu Glu Asp Glu Lys
                165                 170                 175

Ser Ala Leu Gln Thr Glu Ile Ala Asn Leu Leu Lys Glu Lys Glu Lys
            180                 185                 190

Leu Glu Phe Ile Leu Ala Ala His Arg Pro Ala Cys Lys Ile Pro Asp
        195                 200                 205

Asp Leu Gly Phe Pro Glu Glu Met Ser Val Ala Ser Leu Asp Leu Thr
    210                 215                 220

Gly Gly Leu Pro Glu Ala Ser Thr Pro Glu Ser Glu Glu Ala Phe Thr
225                 230                 235                 240
```

```
Leu Pro Leu Leu Asn Asp Pro Glu Pro Lys Pro Ser Leu Glu Pro Val
            245                 250                 255

Lys Ser Ile Ser Asn Val Glu Leu Lys Ala Glu Pro Phe Asp Asp Phe
            260                 265                 270

Leu Phe Pro Ala Ser Ser Arg Pro Ser Gly Ser Glu Thr Ser Arg Ser
            275                 280                 285

Val Pro Asp Val Asp Leu Ser Gly Ser Phe Tyr Ala Ala Asp Trp Glu
        290                 295                 300

Pro Leu His Ser Asn Ser Leu Gly Met Gly Pro Met Val Thr Glu Leu
305                 310                 315                 320

Glu Pro Leu Cys Thr Pro Val Val Thr Cys Thr Pro Gly Cys Thr Thr
                325                 330                 335

Tyr Thr Ser Ser Phe Val Phe Thr Tyr Pro Glu Ala Asp Ser Phe Pro
            340                 345                 350

Ser Cys Ala Ala Ala His Arg Lys Gly Ser Ser Ser Asn Glu Pro Ser
            355                 360                 365

Ser Asp Ser Leu Ser Ser Pro Thr Leu Leu Ala Leu
370                 375                 380

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

AAGAAATGGA GGCTCATAAA TACCACAGCT                                           30

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

ATTGGAAGAA GACCAAAGCA AGAGCAACTA                                           30

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

TAAGTAAGTA GTGCTGTATG AATACAGACA                                           30

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
```

-continued

```
        (D) TOPOLOGY: linear (ii) MOLECULE TYPE: DNA (xi) SEQUENCE DESCRIPTION: SEQ ID NO: 20:

TACTGGCAAT ATATTACAGA TGGGTTTATG                              30

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

GTGTGCAGCT TATGATGCTA TTCTTGAA                                28

(2) INFORMATION FOR SEQ ID NO: 22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

CGCGTCACCA CATACGGAGT CATC                                    24

(2) INFORMATION FOR SEQ ID NO: 23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

CTGGAGGAGT TCCAAGATGT CTACT                                   25

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

TGGAAAGAGC TTGGGGAAGG TGAG                                    24
```

JNK3 MODULATORS AND METHODS OF USE

This application claims priority from provisional application Ser. No. 60/060,995, filed Oct. 3, 1997.

STATEMENT AS TO FEDERALLY SPONSORED RESEARCH

This invention was made, in part, with support from the National Institutes of Health. The government may have certain rights in the invention.

FIELD OF THE INVENTION

The invention relates to screening assays for the detection of inhibitors of protein kinase expression or activity.

BACKGROUND OF THE INVENTION

Apoptosis, or programmed cell death, is a prominent feature of the nervous system during normal development and in adult brain exposed to environmental stress (Kuida et al., Nature, 384:368–372, 1996; Ratan et al., Neurochem., 62:376–379, 1994; Raff et al., Science, 262:695–700, 1993). Stress-induced apoptosis has been implicated in a variety of neurological diseases (Thompson, Science, 267:1456–1462, 1995) and requires de novo protein and RNA synthesis (Martin et al., J. Cell. Biol., 106:829–844, 1988; Oppenheim et al., Dev. Biol., 138:104–113, 1990). Increased expression of c-Jun protein is associated with neuronal damage following global ischemia (Neumann-Haefelin et al., Cerebral Flow Metab,, 14:206–216, 1994) or transection of nerve axons in vivo (Neumann-Haefelin, supra). Increased expression and phosphorylation of c-Jun have been observed in vitro prior to the apoptotic death of sympathetic neurons deprived of nerve growth factor (NGF) (Ham et al., Neuron, 14:927–939, 1995). Moreover, expression of a dominant negative mutant c-Jun, or treatment with c-Jun antibody protects NGF-deprived sympathetic neurons from apoptosis (Ham et al., supra; Estus et al., J. Cell. Biol., 127:1717–1727, 1994). However, the requirement of c-Jun for stress-induced neuronal apoptosis has not been tested in vivo since c-Jun deficient mice die during mid-gestation (Hilberg et al., Nature, 365:179–181, 1993).

Protein phosphorylation is one important mechanism involved in the activation of c-Jun in response to environmental stress signals (Whitmarsh et al., J. Mol. Med., 74:589–607, 1996). c-Jun N-terminal kinase (JNK, also known as SAPK) is a serine/threonine protein kinase that phosphorylates two residues (Ser-63 and Ser-73) on the $NH_2$-terminal activation domain of c-Jun (Whitmarsh et al., supra; Dèrijard et al., Cell, 76:1025–1037, 1994; Kyriakis et al., Nature, 369:156–160, 1994). Map kinase kinase (MKK) 4 (also known as SEK1) is a direct activator of JNK in response to environmental stresses and mitogenic factors (Whitmarsh et al, supra; Dèrijard et al, supra; Nishina et al., Nature, 385:350–353, 1997; Yang et al., Proc. Nat. Acad. Sci. USA, 94:3004–3009, 1997; Sanchez et al., Nature, 372:794–798, 1994). JNK also phosphorylates ATF2 and other Jun-family proteins which function as components of the AP-1 transcription factor complex (Whitmarsh et al., supra; Gupta et al., Science, 267:389–393, 1995; Gupta et al., EMBO J., 15:2760–2770, 1996). The phosphorylation of these transcription factors by JNK leads to increased AP-1 transcriptional activity (Whitmarsh et al., supra). Conversely, the induction of AP-1 transcriptional activity is selectively blocked in cells lacking MKK4 (Yang et al., supra).

JNK has been implicated in the apoptosis of NGF-differentiated PC12 pheochromocytoma cells (Xia et al., Science, 270:1326–1311, 1995), one model system of neuronal cell death in vivo (Batistatou et al., J. Cell. Biol., 122:523–532, 1993). When differentiated PC12 cells are deprived of nerve growth factor (NGF), JNK activation is observed prior to apoptotic death (Xia et al., supra). Transfection studies using constitutively activated and dominant negative mutant components of the JNK signaling pathway established that JNK is involved in NGF withdrawal-induced apoptosis of PC12 cells (Xia et al., supra).

Ten JNK isoforms, resulting from alternative splicing of three different genes have been identified (D+e,fra e+ee rijard et al., supra; Kyriakis et al., supra; Gupta et al., supra; Martin et al., Brain Res. Mol. Brain Res., 35:47–57, 1996). Although the JNK1 and JNK2 isoforms are widely expressed in murine tissues, including the brain, the JNK3 isoforms are predominantly expressed in the brain and, to a lesser extent, in the heart and testis.

SUMMARY OF THE INVENTION

The invention is based on the discovery that mice lacking the JNK3 gene (JNK3(−/−)) develop normally and are resistant to excitotoxic damage, and that JNK3 plays a role in stress-induced seizure activity, AP-1 transcriptional activation, and kainate-induced apoptosis of hippocampal neurons. Thus, JNK3 is a mediator of kainate/glutamate excitotoxicity and a target for limiting or preventing excitotoxic damage.

The invention features a method of identifying a candidate compound that modulates JNK3 expression. The method includes the steps of incubating a cell that can express a JNK3 protein with a compound under conditions and for a time sufficient for the cell to express the JNK3 protein when the candidate compound is not present. The expression of JNK3 is then measured in the cell in the presence of the compound. The expression of JNK3 is also measured in a control cell under the same conditions and for the same time. The amount of JNK3 expression in the cell incubated in the presence of the compound and in the control cell is compared. A difference in JNK3 expression indicates that the compound modulates JNK3 expression. In an embodiment of this method, the compound decreases JNK3 expression.

In another embodiment, the invention features a method of identifying a candidate compound that modulates JNK3 activity. The method includes the steps of incubating a cell that has JNK3 activity with a compound under conditions and for a time sufficient for the cell to express JNK3 activity when the candidate compound is not present. The activity of JNK3 is then measured in the cell in the presence of the compound. The activity of JNK3 is also measured in a control cell under the same conditions and for the same time. The amount of JNK3 activity in the cell incubated in the presence of the compound and in the control cell is compared. A difference in JNK3 activity indicates that the compound modulates JNK3 activity. In an embodiment of this method, the compound decreases JNK3 activity.

The invention also includes a method of identifying a compound that modulates the binding of a JNK3 polypeptide to a substrate. The method involves comparing the amount of a JNK3 polypeptide bound to a substrate in the presence and absence of a selected compound. A difference in the amount of binding of a JNK3 polypeptide to the substrate indicates that the selected compound modulates the binding of a JNK3 polypeptide. In an embodiment of this method, the binding of a JNK3 polypeptide to a substrate is decreased.

Another feature of the invention is a method for generating a totipotent mouse cell comprising at least one inactivated JNK3 gene. The method includes: a) providing a plurality of totipotent mouse cells; b) introducing into the cells a DNA construct that includes a mouse JNK3 gene disrupted by the insertion of a sequence into the gene, thus the disruption prevents expression of functional JNK3; c) incubating the cells so that homologous recombination occurs between the chromosomal sequence encoding JNK3 and the introduced DNA construct; and d) identifying a totipotent mouse cell that has at least one inactivated JNK gene.

Also featured in the invention is a method for generating a mouse homozygous for an inactivated JNK3 gene. The method includes the steps of: a) providing a totipotent mouse cell that contains at least one inactivated JNK3 gene; b) inserting the cell into a mouse embryo and implanting the embryo into a female mouse; c) permitting the embryo to develop into a neonatal mouse; d) permitting the neonatal mouse to reach sexual maturity; e) mating two of the sexually mature mice to obtain a mouse homozygous for the inactivated JNK3 gene. Such a mouse (homozygous JNK3 (−/−)) is resistant to excitotoxic damage.

The invention also features methods of treating a patient having or at risk for a disorder of the nervous system involving excitotoxicity. The methods include administering to the patient a therapeutically effective amount of a compound that inhibits JNK3 expression, or a therapeutically effective amount of a compound that inhibits JNK3 activity. An antisense nucleic acid molecule or ribozyme can be used as the inhibitory compound. Disorders that can be treated by these methods include dementias including Alzheimer's disease, neurodegenerative diseases such as Huntington disease, cerebrovascular disorders such as ischemia, amyotrophic lateral sclerosis, trauma including that caused by heat or cold, motor neuron disease, Parkinson's disease, or seizure disorders including epilepsy. Neuroendocrine disorders such as those that affect pituitary glands, adrenal glands, testis, or pancreas (e.g., β-cells) can be treated with JNK3 modulators.

The invention also includes a transgenic non-human mammal having a transgene disrupting expression of a JNK3 gene, the transgene being chromosomally integrated into germ cells of the mammal. In an embodiment of the invention, the mammal is a mouse. The germ cells of the mammal can be homozygous for the transgene and the disruption of JNK3 gene expression can be the result of a null mutation. Another embodiment of the invention includes a cell line descended from a cell of the mammal having the transgene disrupting expression of a JNK3 gene.

A DNA construct comprising a disrupted mouse JNK3 gene is also featured in the invention. The disruption is by insertion of a sequence into the gene such that the disruption prevents or modifies the expression of functional JNK3.

Unless otherwise specified, "JNK3" can refer both to nucleic acids and polypeptides, such as the sequences shown in FIGS. 1A–5B (SEQ ID NOS:1–12; see also, GenBank accession number: U34819 which corresponds to SEQ ID NO:1 and SEQ ID NO:2; U34820 which corresponds to SEQ ID NO:4 and SEQ ID NO:5; U07620 which corresponds to SEQ ID NO:7 and SEQ ID NO:8; L27128 which corresponds to SEQ ID NO:9 and SEQ ID NO:10; and L35236 which corresponds to SEQ ID NO:11 and SEQ ID NO:12). SEQ ID NO:3 and SEQ ID NO:6 represent deduced nucleotide sequences based on the presumed overlap between the sequences represented by SEQ ID NOS:1 and 4 with the sequence represented by SEQ ID NO:7. JNK3 also refers to polypeptides that are at least 85% identical to the amino acid sequences listed above, and to the nucleic acids encoding those polypeptides. Examples of these sequences and methods of isolating them are found in Gupta et al., supra, 1996; Kyriakis et al., supra; Martin et al., Brain Res. Mol. Brain Res., 35:45–57, 1996; and Mohit et al., Neuron, 14:67–78, 1995.

A "control" cell is a cell that is generally the same, e.g., genotypically and phenotypically, as the cell to which it is being compared (e.g., the cells can be sister cells), but which is not exposed to a test compound.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated in their entirety. In case of conflict, the present specification, including definitions, will control. In addition, the materials, methods, and examples are illustrative only and not intended to be limiting.

Other features and advantages of the invention will be apparent from the following detailed description and from the claims.

BRIEF DESCRIPTION OF THE DRAWINGS

FIG. 1A is a schematic representation of the nucleic acid sequence of GenBank Accession No. U34819 (SEQ ID NO:1).

FIG. 1B is a schematic representation of the amino acid sequence of GenBank Accession No. U34819 (SEQ ID NO:2).

FIG. 1C is a schematic representation of the nucleic acid sequence of SEQ ID NO:3.

FIG. 2A–B is a schematic representation of the nucleic acid sequence of GenBank Accession No. U34820 (SEQ ID NO:4).

FIG. 2C is a schematic representation of the amino acid sequence of GenBank Accession No. U34820 (SEQ ID NO:5).

FIG. 2D is a schematic representation of the nucleic acid sequence of SEQ ID NO:6.

FIG. 3A–B is a schematic representation of the nucleic acid sequence of GenBank Accession No. U07620 (SEQ ID NO:7).

FIG. 3C is a schematic representation of the amino acid sequence of GenBank Accession No. U07620 (SEQ ID NO:8).

FIG. 4A is a schematic representation of the nucleic acid sequence of GenBank Accession No. L27128 (SEQ ID NO:9).

FIG. 4B is a schematic representation of the amino acid sequence of GenBank Accession No. L27128 (SEQ ID NO:10).

FIG. 5A is a schematic representation of the nucleic acid sequence of GenBank Accession No. L35236 (SEQ ID NO:11)

FIG. 5B is a schematic representation of the amino acid sequence of GenBank Accession No. L35236 (SEQ ID NO:12).

FIG. 9A is a schematic representation of the nucleic acid sequence of murine c-Jun (GenBank Accession No. X12740; SEQ ID NO:13).

FIG. 9B is a schematic representation of the amino acid sequence of murine c-Jun (GenBank Accession No. X12740; SEQ ID NO:14).

FIG. 10A-B is a schematic representation of the nucleic acid sequence of murine c-Fos (GenBank Accession No. V00727; SEQ ID NO:15).

FIG. 10C is a schematic representation of the amino acid sequence of murine c-Fos (GenBank Accession No. V00727; SEQ ID NO:16)

DETAILED DESCRIPTION

Figure 6:
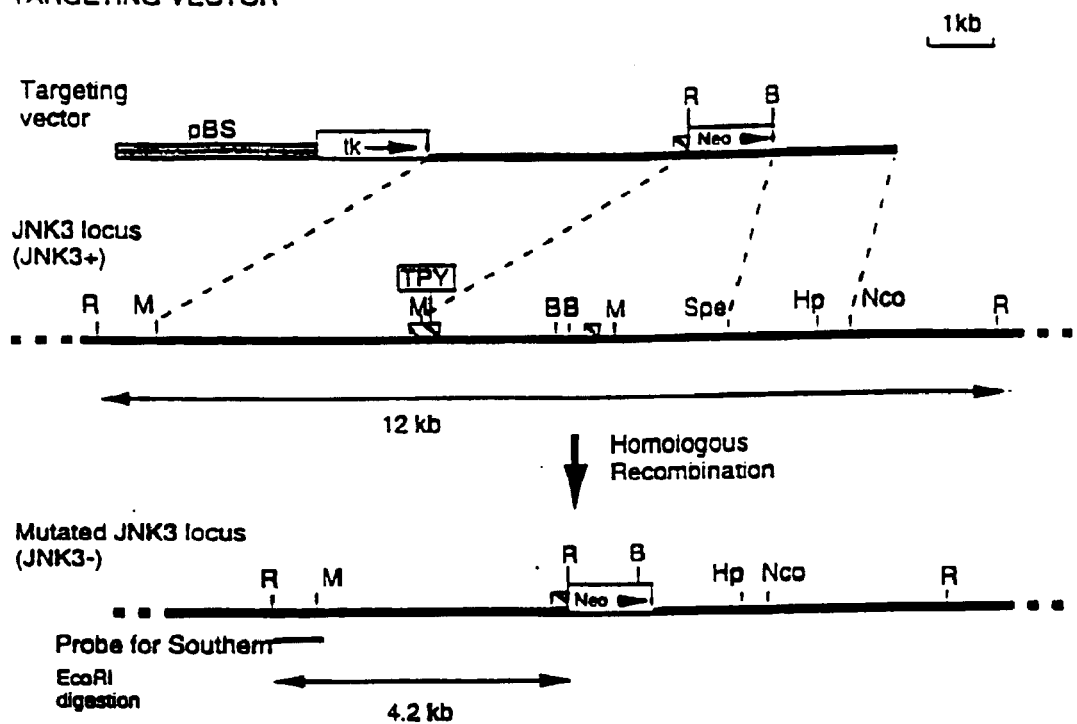
FIG. 6 is a diagram of the wild type JNK3 gene locus, targeting vector, and the mutated or disrupted JNK3 gene locus.

JNK protein kinase phosphorylates c-Jun and subsequently increases AP-1 transcriptional activity in response to a specific group of stress signals (Whitmarsh et al, supra; Yang et al., supra). The neural-specific expression of JNK3 may render neurons particularly susceptible to physiological stress. In the experiments described herein, a remarkable resistance to kainic acid (KA)-induced seizures and apoptosis has been observed in JNK3-deficient mice. The resistance to KA neurotoxicity may be due to the elimination of a specific stress-response pathway mediated by the JNK3 isoform of JNK protein kinase. First, the administration of KA caused the phosphorylation of the $NH_2$-terminal activation domain of c-Jun and markedly increased AP-1 transcriptional activity in wild-type, but not in JNK3-deficient mice. Second, there was prolonged expression of phosphorylated c-Jun within the most vulnerable area of the hippocampus, further indicating that JNK activity may lead to neuronal apoptosis.

The findings reported herein are consistent with the dependence of KA neurotoxicity on excitatory circuitry (Nadler et al., Brain Res. 195:47–56, 1980). Since JNK3 is widely expressed in the nervous system and its activity is increased by many different stress signals (Gupta et al., supra), JNK3 may be involved in stress-induced apoptosis caused by a wide range of environmental insults.

The identification of JNK3 as a critical mediator of KA-induced excitatory neurotoxicity has clinical implications. The amino acid sequence of mouse, rat and human JNK3 is highly conserved (Kyriakis et al., supra; Gupta et al., supra; Martin et al., supra; Mohit et al., Neuron. 14:67–78, 1995). Moreover, the expression of the human JNK3 gene is also restricted to the nervous system and neuroendocrine system, is widely expressed in many brain subregions (Gupta et al., supra; Mohit et al., supra). It is therefore likely that the human and rodent JNK3 protein kinases have related or identical physiological functions. Neurotoxicity of the excitatory amino acids has been implicated in many neurological disorders ranging from acute ischemia to chronic neurodegenerative diseases (Choi, Neuron, 1:623–634, 1988; Lipton et al., N. Engl. J. Med. 330:613–622, 1994; Rothman et al., Annu. Neurol. 19:105–111, 1986). Previous therapeutic strategies have been focused on the prevention of calcium influx through cell surface channels, such as the NMDA-type glutamate receptor. To date, these approaches have only met with mixed results (Lipton et al., supra). JNK3 is therefore a target for therapeutic interventions when excitatory neurotoxicity involves JNK3-mediated apoptosis.

In the experiments described infra, homologous recombination was used to generate JNK3-deficient mice, and their responses to noxious stimuli were examined. KA, a potent excitotoxic chemical, elicits limbic seizures and neuronal cell death. The neurotoxicity of KA derives from the direct stimulation of the glutamate receptor at postsynaptic sites, and an indirect increase in the release of excitatory amino acids from presynaptic sites. It is well-documented that systemic application of KA induces the expression of various cellular immediate early genes (cIEGs), including c-Jun and c-Fos. Thus, the application of KA triggers a stress-response pathway in the brain in vivo. The experiments detailed infra demonstrate that KA induces phosphorylation of c-Jun and an increase in AP-1 transcriptional activity in the brain of wild-type mice. However, these effects of KA are markedly suppressed in the brains of JNK3-deficient mice. Moreover, JNK3-deficient mice exhibit a remarkable resistance to KA-induced seizures and apoptosis of hippocampal neurons. These normal mice treated with KA represent a useful model of human disorders of the nervous system involving excitotoxicity.

Based on these experimental results, JNK3 was found to be an exceptional target for limiting excitotoxic damage. In particular, JNK3 is a target in screening protocols including protocols to screen for molecules that regulate JNK3 gene expression, JNK3 binding to its substrates, and JNK3 activity, as described below. The molecules found in these screens that effectively decrease JNK3 expression or activity are candidate drugs to be used to treat disorders of the nervous system involving excitotoxicity, including seizure disorders such as epilepsy, cerebrovascular disorders including ischemia, metabolic imbalance (e.g., hypoglycemia), injury due to extreme heat or cold, trauma (e.g., irradiation, spinal cord injury, pressure, and ionic imbalance), dementias such as Alzheimer's disease, Parkinson's disease, and neurodegenerative disorders (e.g., Huntington disease), and motoneuron disease (including amyotrophic lateral sclerosis) (Thompson, Science, 267:1456–1462, 1995; Coyle et al., Science, 262:689–695, 1993).

Methods of Screening for Molecules that Inhibit JNK3 Activity

The following assays and screens can be used to identify compounds that are effective inhibitors of JNK3 activity. The assays and screens can be done by physical selection of molecules from libraries, and computer comparisons of digital models of compounds in molecular libraries and a digital model of the JNK3 active site. The inhibitors identified in the assays and screens may act by, but are not limited to, binding to JNK3 (e.g., from mouse or human), binding to intracellular proteins that bind to JNK3, compounds that interfere with the interaction between JNK3 and its substrates, compounds that modulate the activity of a JNK3 gene, or compounds that modulate the expression of a JNK3 gene or a JNK3 protein.

Assays can also be used to identify molecules that bind to JNK3 regulatory sequences (e.g., promoter sequences), thus modulating gene expression. See, e.g., Platt, *J. Biol. Chem.,* 269:28558–28562, 1994.

The compounds that can be screened by the methods described herein include, but are not limited to, peptides and other organic compounds (e.g., peptidomimetics) that bind to a JNK3 protein or inhibit its activity in any way. Such compounds may include, but are not limited to, peptides; for example, soluble peptides, including but not limited to members of random peptide libraries (see, e.g., Lam et al., Nature 354:82–84, 1991; Houghten et al., Nature 354:84–86, 1991), and combinatorial chemistry-derived molecular libraries made of D-and/or L-amino acids, phosphopeptides (including, but not limited to, members of random or partially degenerate, directed phosphopeptide libraries; see, e.g., Songyang et al., Cell 72:767–778, 1993), and small organic or inorganic molecules.

Compounds and molecules are screened to identify those that affect expression of a JNK3 gene or some other gene involved in regulating the expression of JNK3 (e.g., by interacting with the regulatory region or transcription factors of a gene). Compounds are also screened to identify those that affect the activity of such proteins (e.g., by inhibiting JNK3 activity) or the activity of a molecule involved in the regulation of JNK3.

Computer modeling or searching technologies are used to identify compounds, or identify modified compounds that modulate or are candidates to modulate the expression or activity of a JNK3 protein. For example, compounds likely to interact with the active site of the JWK3 protein are identified. The active site of JNK3 can be identified using methods known in the art including, for example, analysis of the amino acid sequence of a molecule, and from a study of complexes formed by JNK3 with a native ligand (e.g., ATF2 or c-Jun). Chemical or X-ray crystallographic methods can be used to identify the active site of JNK3 by the location of a bound ligand such as c-Jun or ATF2.

The three-dimensional structure of the active site can be determined. This can be done using known methods, including X-ray crystallography, which can be used to determine a complete molecular structure. Solid or liquid phase NMR can be used to determine certain intra-molecular distances. Other methods of structural analysis can be used to determine partial or complete geometrical structures. Geometric structure can be determined with a JNK3 protein bound to a natural (e.g., c-Jun or ATF2) or artificial ligand which may provide a more accurate active site structure determination.

Computer-based numerical modeling can be used to complete an incomplete or insufficiently accurate structure. Modeling methods that can be used are, for example, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected from force fields known in physical chemistry. Information on incomplete or less accurate structures determined as above can be incorporated as constraints on the structures computed by these modeling methods.

Having determined the structure of the active site of a JNK3 protein, either experimentally, by modeling, or by a combination of methods, candidate modulating compounds can be identified by searching databases containing compounds along with information on their molecular structure. The compounds identified in such a search are those that have structures that match the active site structure, fit into the active site, or interact with groups defining the active site. The compounds identified by the search are potential JNK3 modulating compounds.

These methods may also be used to identify improved modulating compounds from an already known modulating compound or ligand. The structure of the known compound is modified and effects are determined using experimental and computer modeling methods as described herein. The altered structure is compared to the active site structure of a JNK3 protein to determine or predict how a particular modification to the ligand or modulating compound will affect its interaction with that protein. Systematic variations in composition, such as by varying side groups, can be evaluated to obtain modified modulating compounds or ligands of preferred specificity or activity.

Given the teachings herein, additional experimental and computer modeling methods useful to identify modulating compounds based on identification of the active sites of a JNK3 protein and related transduction and transcription factors an be developed by those skilled in the art.

Examples of molecular modeling systems are the QUANTA programs, e.g., CHARMm, MCSS/HOOK, and X-LIGAND, (Molecular Simulations, Inc., San Diego, Calif.). QUANTA provides a modeling environment for two dimensional and three dimensional modeling, simulation, and analysis of macromolecules and small organics. Specifically, CHARMm analyzes energy minimization and molecular dynamics functions. MCSS/HOOK characterizes the ability of an active site to bind a ligand using energetics calculated via CHARMm. X-LIGAND fits ligand molecules to electron density patterns of protein-ligand complexes. The program also allows interactive construction, modification, visualization, and analysis of the behavior of molecules with each other.

Articles reviewing computer modeling of compounds interacting with specific proteins can provide additional guidance. For example, see, Rotivinen et al., Acta Pharmaceutical Fennica 97:159–166, 1988; Ripka, New Scientist 54–57 (Jun. 16, 1988); McKinaly and Rossmann, Ann. Rev. Pharmacol. Toxicol. 29:111–122, 1989; Perry and Davies, OSAR: Quantitative Structure-Activity Relationships in Drug Design pp.189–193 (Alan R. Liss, Inc., 1989); Lewis and Dean, Proc. R. Soc. Lond. 236:125–140, 141–162, 1989; and, regarding a model receptor for nucleic acid components, see Askew et al., Am. J. Chem. Soc. 111:1082–1090. Computer programs designed to screen and depict chemicals are available from companies such as MSI (supra), Allelix, Inc. (Mississauga, Ontario, Canada), and Hypercube, Inc. (Gainesville, Fla.). These applications are largely designed for drugs specific to particular proteins; however, they may be adapted to the design of drugs specific to identified regions of DNA or RNA. Commercial sources of chemical libraries can be used as sources of candidate compounds. Such chemical libraries can be obtained from, for example, ArQule, Inc. (Medford, Mass.).

In addition to designing and generating compounds that alter binding, as described above, libraries of known compounds, including natural products, synthetic chemicals, and biologically active materials including peptides, can be screened for compounds that are inhibitors or activators.

Compounds identified by methods described above may be useful, for example, for elaborating the biological function of JNK3 gene products and in treatment of disorders in which JNK3 activity is deleterious. Assays for testing the effectiveness of compounds such as those described herein are further described below.

In Vitro Screening Assays for Compounds that Bind to JNK3 Proteins and Genes

In vitro systems can be used to identify compounds that can interact (e.g., bind) to JNK3 proteins or genes encoding those proteins. Such compounds may be useful, for example, for modulating the activity of JNK3 polypeptides or nucleic acids, elaborating their biochemistry, or treating disorders caused or exacerbated by JNK3 expression. These compounds may themselves disrupt normal function or can be used in screens for compounds that disrupt normal function.

Assays to identify compounds that bind to JNK3 proteins involve preparation of a reaction mixture of the protein and the test compound under conditions sufficient to allow the two components to interact and bind, thus forming a complex that can be detected and/or isolated.

Screening assays for molecules that can bind to a JNK3 protein or nucleic acid can be performed using a number of methods. For example, a JNK3 protein, peptide, or fusion protein can be immobilized onto a solid phase, reacted with the test compound, and complexes detected by direct or indirect labeling of the test compound. Alternatively, the test compound can be immobilized, reacted with JNK3 polypeptide, and any complexes detected. Microtiter plates can be used as the solid phase and the immobilized component anchored by covalent or noncovalent interactions. Non-covalent attachment may be achieved by coating the solid phase with a solution containing the molecule, and drying. Alternatively, an antibody specific for JNK3 is used to anchor the molecule to the solid surface. Such surfaces may be prepared in advance of use, and stored. JNK3 antibodies can be produced using conventional methods such as those described in Coligan et al. (Current Protocols in Immunology, John Wiley & Sons, Inc., 1994, see Volume 1, chapter 2).

In the assay, the non-immobilized component is added to the coated surface containing the immobilized component under conditions that permit interaction and binding between the two components. The unreacted components are then removed (e.g., by washing) under conditions such that any complexes formed will remain immobilized on the solid phase. The detection of the complexes can be accomplished by a number of methods known to those in the art. For example, the nonimmobilized component of the assay may be prelabeled with a radioactive or enzymatic label and detected using appropriate means. If the non-immobilized entity was not prelabeled, an indirect method is used. For example, if the non-immobilized entity is a JNK3 polypeptide, an antibody against JNK3 is used to detect the bound molecule, and a secondary, labeled antibody is used to detect the entire complex.

Alternatively, a reaction can be conducted in a liquid phase, the reaction products separated from unreacted components, and complexes detected (e.g., using an immobilized antibody specific for a JNK3 protein).

Cell-based assays can be used to identify compounds that interact with JNK3 proteins. Cell lines that naturally express such proteins or have been genetically engineered to express such proteins (e.g., by transfection or transduction with JNK3 DNA) can be used. For example, test compounds can be administered to cell cultures and the phosphorylation of ATF2 or c-Jun measured as described infra. A decrease in the amount of phosphorylation of a JNK3 substrate in the presence of the test compound compared to controls that do not contain the test compound indicates that the test compound is an inhibitor of JNK3 activity.

Inhibitors of JNK3 expression that act on the JNK3 promoter can be identified using a chimeric gene in which genomic sequences including the JNK3 promoter are fused to a reporter, for example firefly luciferase. Cultured cells (including neurons) transformed with this DNA are screened for the expression of luciferase activity. Compounds that inhibit luciferase activity in this high throughput assay can be confirmed by direct measurement of the endogenous JNK3 protein (by Western blotting) and JNK3 mRNA (by Northern blotting) using methods known in the art (for example, see Ausubel et al., *Current Protocols in Molecular Biology*, John Wiley & Sons, 1994).

Candidate inhibitory compounds can be tested further in cell or tissue cultures as well as animal models. For example, cells expressing JNK3 are incubated with a test compound. Lysates are prepared from treated and untreated cells and Western blotted according to known methods. The blots are probed with antibodies specific for JNK3. A decrease in the amount of JNK3 expression in cultures treated with the test compound compared to untreated controls indicates that the test compound is a candidate for a drug to treat disorders associated with JNK3 expression.

Assays for Compounds that Interfere with JNK3/JNK3 Substrate Interactions

Molecules that disrupt the interaction between JNK3 and its substrates can be identified using assays that detect protein-protein interactions. For example, the yeast two-hybrid method detects protein interactions in vivo. However, an in vitro assay is preferable because candidate molecules may not be permeable to the yeast cell wall. An example of an in vitro assay for such test molecules that disrupt the interaction between JNKC3 and a substrate includes the use of immobilized JNK3 or immobilized substrate (e.g., c-Jun) and incubation of the immobilized component with cell lysates or purified proteins in the presence and absence of a test molecule. In general, the test molecule is tested over a range of a 100 fold molar excess over the most abundant component (e.g., the component immobilized or in solution). If the test molecule is predicted to interact with the immobilized component of the assay, then it can be pre-incubated with that component before adding the cell lysate or purified protein. After washing away unbound material, the bound proteins are detected with antibodies (e.g., ELISA or Western blot) or through the use of labeled proteins (e.g. radioactive or fluorescent) using methods known in the art. Test molecules that decrease the amount of substrate bound to JNK3 are thus identified as molecules that interfere with JNK3/JNK3 substrate interactions.

Assays for Compounds that Ameliorate the Effects of JNK3 in vivo

Compounds identified as above, or other candidate compounds that inhibit JNK3 activity in vitro may be useful for treating disorders involving JNK3 activity. These compounds can be tested in in vivo assays, for example, in animal models of disorders involving JNK3 activity. For example, transgenic mouse models of ALS have been described (Bruijn and Cleveland, Neuropathol. Appl. Neurobiol. 22:373–387, 1996; Dal Canto and Gurney, Brain Res. 676: 25–40, 1995; Cleveland et al., Neurology 47: Suppl 2, S54–61) as have transgenic models of Alzheimer's disease such as the PDAPP mouse and others (for examples, see Loring et al., Neurobiol. Aging 17:173–182, 1996). MPTP (1-methyl-4-phenyl-1,2,3,6-tetrahydropyridine)-induced dopaminergic neurotoxicity has been used as a model for Parkinson's disease in rodents and nonhuman primates (for example, Przedborski et al., Proc. Nat'l. Acad. Sci. USA 93:4565–4571, 1996).

Test compounds predicted to inhibit JNK3 activity are administered to animals, e.g., as described above, that serve as models for the various disease paradigms. Treated animals are then assayed for inhibition of JNK3 activity. Such assays may be indirect or inferential, for example, improved health or survival of the animal indicates the efficacy of a test compound. Assays can also be direct, for example, a decrease in JNK3 or c-Jun expression can be measured by Northern analysis of neural tissue removed from an animal treated with a test compound. A decrease in the amount of JNK3 mRNA present in the sample from treated animals compared to untreated controls indicates that the test compound is inhibiting JNK3 expression. A decrease in the amount of c-Jun indicates that the test compound is inhibiting JNK3 expression or activity.

Antisense Constructs and Therapies

Treatment regimes based on an "antisense" approach involve the design of oligonucleotides (either DNA or RNA) that are complementary to JNK3 mRNAs. These oligonucleotides bind to the complementary mRNA transcripts and prevent translation. Absolute complementarily, although preferred, is not required. A sequence "complementary" to a portion of an RNA, as referred to herein, is a sequence sufficiently complementary to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence, up to and including the AUG initiation codon, are generally most efficient for inhibiting translation. However, sequences complementary to the 3' untranslated sequences of mRNAs have also been shown to be effective for inhibiting translation (Wagner, Nature, 372:333, 1984). Thus, oligonucleotides complementary to either the 5' or 3' non-translated, non-coding regions of a JNK3 could be used in an antisense approach to inhibit translation of the endogenous human homolog of JNK3 mRNA. Oligonucleotides complementary to the 5' untranslated region of the mRNA should include the complement of the AUG start codon. Examples of candidate antisense sequences for the 5' and 3' regions are; 5'-AAG AAA TGG AGG CTC ATA AAT ACC ACA GCT-3' (SEQ ID NO:17) and 5'-ATT GGA AGA AGA CCA AAG CAA GAG CAA CTA-3' (SEQ ID NO:18), respectively.

While antisense nucleotides complementary to the coding region of a JNK3 gene could be used, those complementary to transcribed untranslated regions are most preferred. Examples of this type of candidate sequence are 5'-TAA GTA AGT AGT GCT GTA TGA ATA CAG ACA-3' (SEQ ID NO:19) and 5'-TAC TGG CAA TAT ATT ACA GAT GGG TTT ATG-3' (SEQ ID NO:20).

Antisense oligonucleotides complementary to mRNA coding regions are less efficient inhibitors of translation, but could be used in accordance with the invention. Whether designed to hybridize to the 5', 3', or coding region of a JNK3 mRNA, antisense nucleic acids should be at least six nucleotides in length, and are preferably oligonucleotides ranging from 6 to about 50 nucleotides in length. In specific aspects, the oligonucleotide is at least 10 nucleotides, or at least 50 nucleotides in length.

Regardless of the choice of target sequence, in vitro studies are usually performed first to assess the ability of an antisense oligonucleotide to inhibit gene expression. In general, these studies utilize controls that distinguish between antisense gene inhibition and nonspecific biological effects of oligonucleotides. In these studies levels of the target RNA or protein are usually compared with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide, and that the nucleotide sequence of the oligonucleotide differs from the antisense sequence no more than is necessary to prevent specific hybridization to the target sequence.

The oligonucleotides can be DNA or RNA, or chimeric mixtures or derivatives or modified versions thereof, single-stranded or double-stranded. The oligonucleotide can be modified at the base moiety, sugar moiety, or phosphate backbone, for example, to improve stability of the molecule or hybridization. The oligonucleotide may include other appended groups such as peptides (e.g., for targeting host cell receptors in vivo), or agents facilitating transport across the cell membrane (as described, e.g., in Letsinger et al., Proc. Natl. Acad. Sci. USA 86:6553, 1989; Lemaitre et al., Proc. Natl. Acad. Sci. USA 84:648, 1987; PCT Publication No. WO 88/09810) or the blood-brain barrier (see, for example, PCT Publication No. WO 89/10134), or hybridization-triggered cleavage agents (see, for example, Krol et al., BioTechniques 6:958, 1988), or intercalating agents (see, for example, Zon, Pharm. Res. 5:539, 1988). To this end, the oligonucleotide can be conjugated to another molecule, e.g., a peptide, hybridization-triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide can also comprise at least one modified sugar moiety selected from the group including, but not limited to, arabinose, 2-fluoroarabinose, xylulose, and hexose.

The antisense oligonucleotide can also include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The antisense oligonucleotide can include an α-anomeric oligonucleotide. An α-anomeric oligonucleotide forms specific double-stranded hybrids with complementary RNA in which, contrary to the usual β-units, the strands run parallel to each other (Gautier et al., Nucl. Acids. Res. 15:6625, 1987). The oligonucleotide is a 2'-0-methylribonucleotide (Inoue et al., Nucl. Acids Res. 15:6131, 1987), or a chimeric RNA-DNA analog (Inoue et al., FEBS Lett. 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448, 1988).

The antisense molecules should be delivered to cells that express JNK3 proteins in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, an approach may be used in which a recombinant DNA construct comprises an antisense oligonucleotide placed under the control of a strong pol III or pol II promoter. The use of such a construct to transfect target cells in a patient will result in the transcription of sufficient amounts of single stranded RNAs that will form complementary base pairs with the endogenous JNK3 transcripts and thereby prevent translation of that mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Suitable promoters include, but are not limited to: the SV40 early promoter region (Bernoist et al., Nature 290:304, 1981); the promoter contained in the 3' long terminal repeat of Rous sarcoma virus (Yamamoto et al., Cell 22:787–797, 1988); the herpes thymidine kinase promoter (Wagner et al., Proc. Natl. Acad. Sci. USA 78:1441, 1981); and the regulatory sequences of the metallothionein gene (Brinster et al., Nature 29G:39, 1988). Constructs may also be contained on an artificial chromosome (e.g., mammalian artificial chromosome; MAC; Harrington et al., Nature Genet. 15:345–355, 1997).

The production of a JNK3 antisense nucleic acid molecule by any gene therapeutic approach described above results in a cellular level of JNK3 protein that is less than the amount present in an untreated individual.

Ribozymes

Ribozyme molecules designed to catalytically cleave JNK3 mRNAs can also be used to prevent translation of these mRNAs and expression of JNK3 mRNAs (see, e.g., PCT Publication WO 90/11364; Saraver et al., Science 247:1222, 1990). While various ribozymes that cleave mRNA at site-specific recognition sequences can be used to destroy specific mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., Nature 334:585, 1988). Preferably, the ribozyme is engineered so that the cleavage recognition site is located near the 5' end of the JNK3 mRNA, i.e., to increase efficiency and minimize the intracellular accumulation of non-functional mRNA transcripts.

Examples of potential ribozyme sites in human JNK3 include 5'-UG-3' sites which correspond to the initiator methionine codon at, for example, in human JNK3, about nucleotides 224–226, the codon for a downstream potential initiation site (nucleotides 338–340), and additional codons in the coding region, including nucleotides 698–670; 740–742; and 935–937.

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., Science 224:574, 1984; Zaug et al., Science, 231:470, 1986; Zug et al., Nature 324:429, 1986; PCT Application No. WO 88/04300; and Been et al., Cell 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in JNK3 proteins.

As in the antisense approach, the ribozymes can be composed of modified oligonucleotides (e.g., for improved stability, or targeting), and should be delivered to cells which express a JNK3 gene in vivo, e.g., the brain and spinal cord. A preferred method of delivery involves using a DNA construct "encoding" the ribozyme under the control of a strong constitutive pol III or pol II promoter, so that transfected cells will produce sufficient quantities of the ribozyme to destroy endogenous JNK3 mRNAs and inhibit translation. Because ribozymes, unlike antisense molecules, are catalytic, a lower intracellular concentration is required for efficiency.

For any of the above approaches, the therapeutic JNK3 antisense or ribozyme nucleic acid molecule construct is preferably applied directly to the target area (e.g., the focal site of activity in a seizure disorder, the hippocampus in Alzheimer's disease, the substantia nigra in patients with Parkinson's disease), but can also be applied to tissue in the vicinity of the target area or even to a blood vessel supplying the target area.

For gene therapy, antisense, or ribozyme JNK3 expression is directed by any suitable promoter (e.g., the human cytomegalovirus, simian virus 40, or metallothionein promoters), and its production is regulated by any desired mammalian regulatory element. For example, if desired, enhancers that direct preferential gene expression in cells under excitotoxic induction can be used to direct antisense JNK3 expression in a patient with a seizure disorder.

JNK3 antisense or ribozyme therapy is also accomplished by direct administration of the antisense JNK3 or ribozyme RNA to a target area. This mRNA can be produced and isolated by any standard technique, but is most readily produced by in vitro transcription using an antisense JNK3 DNA under the control of a high efficiency promoter (e.g., the T7 promoter). Administration of antisense JNK3 RNA to target cells is carried out by any of the methods for direct administration of therapeutic compounds described herein.

Methods of Treating Disorders Involving JNK3 Expression or Activity

The invention also encompasses the treatment of disorders, especially in mammals, such as humans, in which JNK3 plays a damaging role. A number of disorders of the nervous system involving excitotoxicity, such as seizure disorders (e.g., epilepsy), dementias such as meurodegenerative disorders (e.g., Alzheimer's disease, Huntington disease), cerebrovascular disorders such as ischemia, motor neuron disease (including ALS), injuries caused by extreme heat or cold, trauma (e.g., irradiation, spinal cord injury, pressure, and ionic imbalance), metabolic imbalance (e.g., hypoglycemia) and Parkinson's disease, can be treated by the methods described herein. Without limiting the invention by committing to any particular theory, a substantial number of neurologic disorders are attributable, at least in part, to excitotoxicity which is mediated by the JNK3 pathway. Thus, inhibitors of this pathway, identified as described above, are useful for treatment of disorders involving excitotoxicity.

Therapy can be designed to reduce the level of endogenous JNK3 gene expression, e.g., using antisense or ribozyme approaches to inhibit or prevent translation of a JNK3 mRNA; triple helix approaches to inhibit transcription of the gene; or targeted homologous recombination to inactivate or "knock out" a gene or its endogenous promoter. The antisense, ribozyme, or DNA constructs described herein can be administered directly to the site containing the target cells; e.g., specific regions of the brain or the spinal cord. Antibodies or fragments of antibodies that recognize JNK3 or a JNK3 substrate, and that have been modified to be expressed or otherwise enter the cell can also be used therapeutically.

Effective Dose

Toxicity and therapeutic efficacy of the compounds of the invention, e.g., compounds that modulate JNK3 expression or activity, can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma can be measured, for example, by high performance liquid chromatography.

Formulations and Use

Pharmaceutical compositions for use in accordance with the present invention can be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

The preferred methods of administering the compositions of the invention are by direct delivery of the compounds to the central nervous system, preferentially to the brain, especially near to or directly at the site of the disorder, e.g., the hippocampus in the case of Alzheimer's disease, the substantia nigra in the case of Parkinson's disease, and the focal site for seizure disorders. Accordingly, administration may be into a ventricle, intrathecal, or intracerebral ventricular. For example, an Omaya reservoir-shunt with in-line filter can be surgically placed into the cisternal space. A therapeutic compound in an appropriate excipient (e.g., phosphate-buffered saline) is instilled into the shunt by injection on a prescribed basis.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds can be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds can also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that particularly useful routes of administration will be nasal or by direct infusion into the central nervous system.

EXAMPLES

Example 1

JNK3 Expression

A 351-bp sequence derived from the 5' region of the mouse JNK3 cDNA (nucleotides 62–412) was labelled with [$^{32}$P] by random priming and used as a probe to determine the tissue expression pattern of the JNK3 gene. Northern blot analysis was performed by standard methods on 2 mg samples of poly(A)$^+$ mRNA isolated from testis, kidney, skeletal muscle, liver, lung, spleen, brain, and heart. All Northern blots were probed with [$^{32}$P]-labelled β-actin as a control to ensure loading of similar amounts of RNA in each lane. A strong signal corresponding to a 2.7 kb transcript, as well as a weak signal corresponding to a 7.0 kb transcript, were detected in brain. A weak signal corresponding to a 2.7 kb transcript was also detected in the heart. A signal corresponding to a 2.4 kb transcript was detected in the testis. JNK3 expression was not detected in the other tissues examined.

In situ hybridization analysis has indicated that JNK3 is expressed in many regions of the brain (Martin et al., supra). Total RNA (10 mg) was therefore isolated from different regions of mouse brain (cerebellum, cerebral cortex, hippocampus, midbrain, thalamus, and brainstem) using the TRIzol reagent (Gibco-BRL), and analyzed by Northern blot using the JNK3 probe described above. A signal corresponding to a 2.7 kb transcript was detected in all sections of the brain examined, and was most abundant in the hippocampus.

Example 2

Targeted Disruption of the JNK3 Gene

To generate JNK3-deficient mice, a targeting vector was designed to replace an internal 4 kb MscI-SpeI JNK3 genomic fragment with a PGKneo cassette. A map of the JNK3 gene, the JNK3 targeting vector, and the predicted structure of the mutated JNK3 gene are shown diagrammatically in FIG. 6. Restriction enzyme sites are indicated (B, BamHI; Hp, HpaI; M, MscI; Nco, NcoI; R, EcoRI; Spe, SpeI). A 10-kb NotI-EcoRI (the NotI site was vector-derived) JNK3 fragment was cloned from a λ FixII phage library of a 129/Sv mouse strain (Stratagene Inc.). The targeting vector was constructed by inserting a 4.0 kb MscI fragment from the 5' end of the JNK3 genomic fragment, a 1.6 kb PGK-neo cassette (Negishi et al., Nature 376:435–438, 1995) and a 1.8-kb SpeI-NcoI fragment of the 3' end of the JNK3 fragment into pBluescript KS vector (Stratagene Inc.) using appropriate linkers. The targeting vector contains a 2.6-kb PGK tk cassette (Negishi et al., supra) flanking the 5' end of the JNK3 genomic sequence for negative-selection of mutant ES cells (Mansour et al., 336:348–352, 1988). The region replaced in the JNK3 gene by the targeting vector encompasses one and a half exons encoding amino acids 211 to 267 of JNK3 (as shown in FIG. 5B). This region includes the tripeptide dual phosphorylation motif Thr-Pro-Tyr (TPY) that is characteristic of the JNK group and required for protein kinase activity (Dèrijard et al., supra). The two hatched boxes shown in the JNK3 locus correspond to subdomains VIII and IX (encoding amino acid residues 189–267 in the JNK3 protein shown in FIG. 5B) of JNK3.

The targeting vector was linearized with NotI and electroporated into W9.5 embryonic stem (ES) cells. Genomic DNA from transfectants resistant to G418 (200 mg/ml) (Gibco BRL) and gancyclovir (2 mM) (Syntex, Pala Alto, Calif.) were isolated and screened by Southern blot analysis. Southern blot analysis of 104 independent G418- and gancyclovir-resistant clones revealed three clones containing the desired homologous recombination event (targeting frequency 2.9%). Chimeric mice were generated by injecting these ES cells into C57BL/6 (B6) mouse blastocysts.

Southern blots of EcoRI-restricted DNA derived from the tails of these chimeric mice were probed with the radiolabeled 351 bp JNK3 probe. EcoRI digestion resulted in a 12 kb band corresponding to the wild-type (endogenous allele), and a 4.2 kb band corresponding to the mutant (disrupted allele).

Two clones mediated germline transmission of the disrupted JNK3 allele into the next generation of mice. Heterozygotes (+/−) were intercrossed to generate homozygous mutant mice (−/−) that were identified by Southern blot analysis of genomic DNA. Total RNA isolated from mouse brain was examined by Northern blot analysis. The blot was probed with a random-primed $^{32}$P-labeled mouse JNK3 cDNA probe, then stripped and sequentially reprobed with mouse JNK1 and β-actin cDNA probes. The major JNK3 transcript in brain is 2.7 kb, and the JNK1 transcripts in mouse brain are 2.3 and 4.4 kb. Blots hybridized with a JNK3 cDNA probe detected transcripts in wild-type (+/+), but not in homozygous knockout (−/−) mice.

Reverse transcriptase-polymerase chain reaction (RT-PCR) analysis was used to confirm that JNK3 transcripts were absent in the homozygous JNK3 (−/−) brain. A JNK1 probe (447 bp) was amplified from mouse brain RNA by RT-PCR (Yang et al., supra) using the amplimers 5'-GTGTGCAGCTTATGATGCTATTCTTGAA-3' (SEQ ID NO:21) and 5' CGCGTCACCACATACGGAGTCATC-3' (SEQ ID NO:22). RT-PCR detection (Yang et al., supra) of JNK3 mRNA in mouse tissues was performed by RT-PCR using the amplimers: 5'-CTGGAGGAGTTCCAAGATG-TCTACT-3' (SEQ ID NO:23) and 5'-TGGAAAGA-GCTTGGGGAAGGTGAG-3' (SEQ ID NO:24) to yield a specific 537 bp DNA product. RNA isolated from mouse brain was amplified with primers specific for HPRT as a control. These experiments confirmed the absence of JNK3 transcripts in the homozygous JNK3 (−/−) brain.

Protein kinase assays were performed to show that JNK3 (−/−) mouse brain was deficient in JNK3 activity. In these experiments, JNK3 kinase activity in brain lysates was measured after immunodeletion of JNK1 and JNK2 by in-gel protein kinase assays using the substrate GST-cJun (Dèrijard et al., supra). When mouse hippocampal lysates (30 μg) from wild type (+/+) and homozygous knockout (−/−) brains were assayed, the 55 kD and 46 kD JNK3 isoforms were detected in wild type but not JNK3 (−/−) mice, confirming that JNK3 (−/−) mouse brain was deficient in JNK3 kinase activity. Together, these data demonstrate that the targeted disruption of the JNK3 gene resulted in a null allele.

The JNK3(−/−) mice were fertile and of normal size. Histological surveys of a variety of tissues revealed no apparent abnormality using hematoxylin and eosin (H & E) staining of heart, lung, thymus, spleen, lymph nodes, liver, kidney, and skeletal muscle. JNK3(−/−) and wild-type mouse brains were examined by immunocytochemical analysis of a pyramidyl neuronal marker (MAP-2), interneuronal markers calbindin and parvalbumin, an astrocyte marker (glial fibrillary acidic protein; GFAP; Hsu et al., J. Histochem. Cytochem. 29:577–580, 1981), and Nissl's stain (Hsu et al., supra). These studies revealed that JNK3(−/−) mice had apparently normal development and structural organization of the brain. A comparable number of motor neurons were found in the facial nucleus in wild-type and JNK3(−/−) mice (2150–2300 neurons per nucleus at postnatal day 10, n=4). The neurons were identified by morphology and were counted by a double-blind assay of serial sections throughout the facial nuclei of wild-type and JNK3 (−/−) mice. Thus, there is no apparent developmental abnormality, including cell death, in JNK3 (−/−) mice.

Example 3

JNK3 Deficient Mice are Resistant to KA-Induced Seizures

Figure 7:
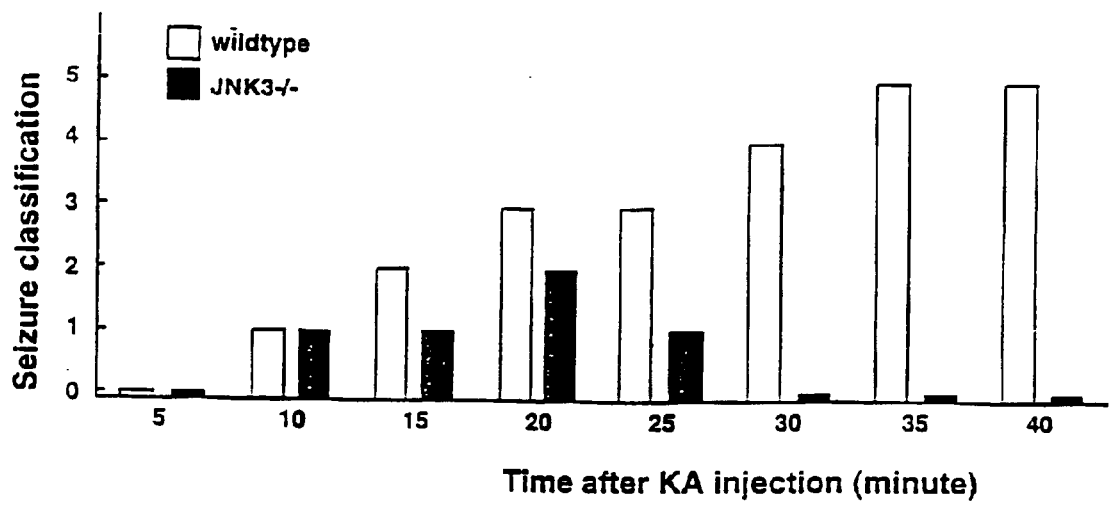
FIG. 7 is a bar graph showing the temporal responses of wild type and JNK3(−/−) mice to kainic acid (KA) injection.
Figure 8:
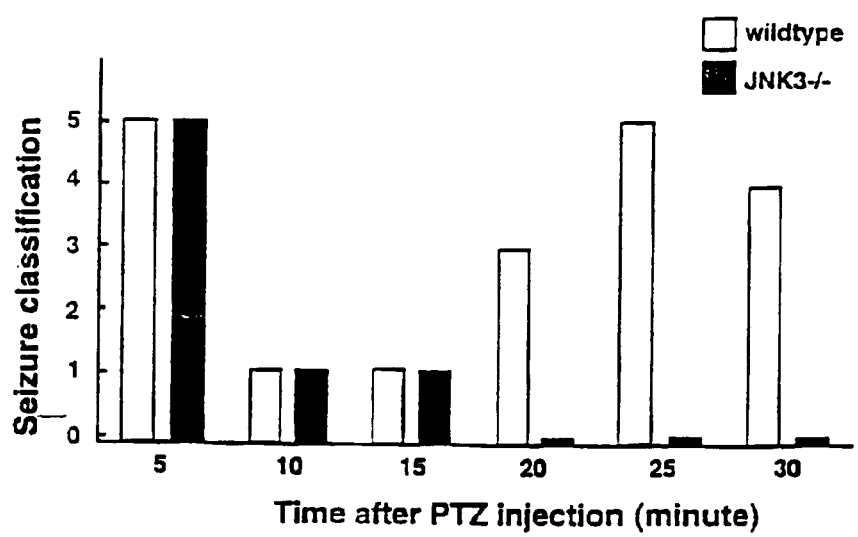
FIG. 8 is a bar graph showing the temporal responses of wild type and JNK3(−/−) mice to pentetrazole (PTZ) injection.

JNK3(−/−) mice and their wild-type littermates were injected intraperitoneally (i.p.) with 30 mg/kg KA to induce seizures (Ben-Ari, supra). In wild-type mice, the administration of KA first induced "staring spells" with abnormal body posture, then progressed to head nodding ("wet-dog shakes"), fore-paw tremor, rearing, loss of postural control, and eventually, continuous convulsions. The seizure activities typically subsided one hour after injection. Wild-type and heterozygous mice developed motor symptoms of seizures, including rearing, at 30 to 40 minutes post-injection. The JNK3 (−/−) mice, in contrast, developed much milder symptoms, mainly consisting of "staring" spells and occasional myoclonic tremors. At this dose, JNK3 (−/−) mice did not develop grand mal seizures and recovered much faster than did wild-type and heterozygous mice. JNK3(−/−) mice developed seizures of comparable severity to wild-type mice only at higher dosages of KA (45 mg/kg, i.p.). However, at this high dose of KA, more than 60% of wild-type mice died from continuous tonic clonic convulsions, while all of the JNK3(−/−) mice survived. These results indicate that JNK3(−/−) mice were resistant to the effect of the excitotoxin KA. Further, JNK3(−/−) mice recovered from the drug administration more rapidly than wild-type mice (FIG. 7). Seizure classifications as shown in FIGS. 7 and 8 are: 1, arrest of motion; 2, myoclonic jerks of the head and neck, with brief twitching movements; 3, unilateral clonic activity; 4, bilateral forelimb tonic and clonic activity; and 5, generalized tonic-clonic activity with loss of postural tone, often resulting in death.

Example 4

Resistance to Pentetrazole (PTZ)-Induced Seizures

Since the resistance to KA-induced seizures varied between littermates (+/+ and +/− are less resistant than −/− mice), the observed differential susceptibility cannot be attributed to a difference between mouse strains (Schauwecker and Steward, Proc. Nat. Acad. Sci. USA 94:4103–4108, 1997). However, the resistance of JNK3 deficient mice to KA-induced seizures could be due to decreased drug penetration across the blood-brain barrier or an increased GABA (gamma-aminobutyric acid) inhibitory postsynaptic potential (IPSP), or the ablation of a specific signal transduction pathway mediated by the JNK3 protein kinase. To distinguish between these possibilities, the response of JNK3 (−/−) and wild-type mice to another epileptogenic agent, pentetrazole (PTZ) (Sigma), was examined. PTZ was selected due to its ability to induce seizures by blocking the GABA-IPSPs (Ben-Ari et al., Neurosci. 6:1361–1391, 1981).

JNK3(−/−) mice and wild-type littermates developed seizures of comparable severity at all tested dosages of PTZ (30, 40, 50, 60 mg/kg, i.p.; FIG. 8). Moreover, unlike the slow progression of motor symptoms seen in the KA-induced seizures, PTZ induced abrupt general tonic-clonic seizures within five minutes after injection, presumably reflecting that its epileptogenic mechanism works solely through extracellularly inhibition of the GABA-IPSP. Thus, the differential susceptibility to KA toxicity in JNK3 (−/−) mice can neither be explained as a consequence of poor drug delivery to the nervous system nor by potent GABA-IPSPs in the neural circuit. Furthermore, we examined the expression of the kainate-type glutamate receptor subunits GluR5-7 (Pharmingen cat. No. 60006E) by immunocytochemistry using standard methods.

Pyramidal neurons in the hippocampal CA1 subfield were most prominently labeled by the Glu5-7 antibody. Both wild-type and JNK3(−/−) mice showed prominently labeled apical dendrites arising from lightly labeled somata in the CA1 subfield of the hippocampus, a pattern similar to the primate hippocampus (Good et al., Brain Research 624:347–353, 1993). In addition to kainate-type subunit GluR5-7, the expression pattern of the GluR1 subunit that is essential to various glutamate receptor subtypes and the intracellular calcium-binding proteins parvalbumin and calbindin that may buffer the influx of extracellular calcium were also indistinguishable between JNK3(−/−) and wild-type mice. Together, these results indicate no apparent structural abnormality that might be responsible for the resistance of JNK3(−/−) mice to KA-induced excitotoxicity.

Example 5

Attenuation of KA-Induced Phosphorylation of c-Jun

The systemic administration of KA in wild-type mice may induce a stress-response pathway mediated by the JNK3 protein kinase. To explore this possibility, the expression of the immediate-early genes c-fos and c-jun (Morgan et al., Annu. Rev. Neurosci. 14:421–451, 1991; Smeyne et al., Nature 363:166–169, 1993; Kasof et al., J. Neurosci. 15:4238–4249, 1995) was examined to determine whether KA imposed an equivalent level of noxious stimulation on wild-type and JNK3(−/−) mice. Total RNA was extracted from the hippocampi of mice sacrificed before and at 0.5, 2, 4, or 8 hours after KA injection (30 mg/kg, i.p.), and Northern blots were probed with murine c-fos and c-jun probes. The c-Jun probe was a 207 bp fragment corresponding to nucleotides 888–1094 (FIG. 9) of the murine c-Jun cDNA. The c-Fos probe was a 347 bp fragment of the murine c-Fos gene (exon 4; base pairs 2593–2939) (FIG. 10). Both JNK3(−/−) and wild type mice exhibited a comparable level of rapid induction of c-fos and c-jun transcripts, which gradually declined four hours after injection.

To further define this phenomenon, the distribution of KA-induced c-Fos and c-Jun immunoreactivity along the synaptic circuit of the hippocampus was examined. In these experiments, homozygous mutant and control wild-type mice were killed and fixed by transcardial perfusion of 4% paraformaldehyde at 2 or 6 hours after the injection of KA (30 mg/kg, i.p.). Brains from both groups were removed, post-fixed for one hour, and sectioned on a Vibratome (40 mm thick). Tissue sections were processed by immunocytochemistry to detect the expression of c-June (Santa Cruz, cat# sc-45), c-Fos (Santa Cruz, cat# sc-52), and phospho-specific c-Jun (Ser-73) (New England Biolabs, #9164S). Sections were floated in a solution of the primary antibody (diluted 200× in PBS) and incubated overnight at room temperature. Secondary antibody incubation, avidin-biotin conjugated peroxidase (Vectastain Elite ABC kit, Vector Lab.), and DAB (3, 3'-diaminobenzidine, Sigma) reactions were performed using standard procedures (Hsu et al., supra). In the absence of KA, there was no detectable c-Fos expression and only a few c-Jun-positive cells within the dentate gyrus. Two hours after KA injection (30 mg/kg, i.p.), there was a large increase in c-Fos immunoreactivity throughout the hippocampal region that was the same in both wild-type and JNK3(−/−) mice. Simultaneously, there was an increase in the number of c-Jun-positive cells in the dentate gyrus and the CA3 region of the hippocampus in both wild type and JNK3(−/−) mice. By six hours after KA injection, the expression of c-June extended to the CA1 region in both wild-type and JNK3(−/−) mice. The induction of c-Fos and C-Jun is generally accepted as an indicator of neuronal activity following noxious stimulation (Morgan et al., supra). The comparable induction level, time-course, and distribution of c-Jun and c-Fos-labeled cells suggests that JNK3(−/−) and wild type mice were subject to an equivalent level of noxious stress by systemic administration of KA.

C-Jun is activated by phosphorylation of the $NH_2$-terminal activation domain by JNK. The expression of phosphorylated c-Jun provides another measure of whether JNK-like activity was present in JNK3(−/−) mice. The expression of phosphorylated c-Jun was examined using an antibody raised against c-Jun phosphorylated at Ser-73, one of the sites phosphorylated by JNK (Whitmarsh et al., supra; Dèrijard et al., supra; Kyriakis et al., supra). Prior to challenge with KA, no cells were labeled by the antibody in either wild type or JNK3(−/−) mice. By two hours after KA injection, there was a high level of phosphorylated c-Jun in the dentate gyrus and the CA3/CA4 region of the hippocampus in wild-type mice. In contrast, only a trace amount of phosphorylated c-Jun was detected in the JNK3(−/−) mice. Thus, there was either a decreased level or less sustained phosphorylation of c-Jun in the JNK3(−/−) mice.

In addition, there was a dynamic change of the distribution of phosphorylated c-Jun in the wild type mouse hippocampus. By six hours after KA injection, the expression of phosphorylated c-Jun subsided in the dentate gyrus and progressed to a restricted area in the hippocampal CA3 region. Under higher magnification, it was apparent that the expression of phosphorylated c-Jun surrounded a focus of cell destruction. In contrast, no labeling of phosphorylated c-Jun was detected in the JNK3(−/−) mice at the same time point. The hippocampal CA3 region is well documented as the most vulnerable structure to the KA excitotoxicity, presumably due to both a high KA binding affinity (Berger et al., supra) and a potent excitatory synaptic connection between CA3 pyramidal neurons (Westbrook et al., Brain Research 273:97–109, 1983). These results indicate that JNK3 is required for the phosphorylation of c-Jun induced by KA.

Example 6

Attenuation of KA-Induced AP-1 Transcriptional Activity

Since the phosphorylation of c-Jun is an important initial event during the induction of AP-1 transcriptional activity (Whitemarsh et al., supra; Yang et al., supra), whether the observed attenuation of c-Jun phosphorylation would lead to decreased induction of AP-1 transcriptional activity in JNK3 (−/−) mice was examined. JNK(-1-) mice were crossed with transgenic AP-1 luciferase (AP1-luc) mice (Rincon et al., Embo. J. 13:4370–4381, 1994) and progeny back crossed. The JNK3(−/−)/API-Luc(−/+) mice were used in experiments with JNK3(+/+) mice to compare the level of KA-induced AP-1 transcriptional activity in the presence or absence of JNK3. The AP1-luc mice contain the firefly luciferase gene under the control of four copies of a consensus AP-1 binding site in the context of the minimal rat prolactin promoter. It has been established that the expression of luciferase in these mice is due to the presence of the AP-1 regulatory element.

Figure 11:
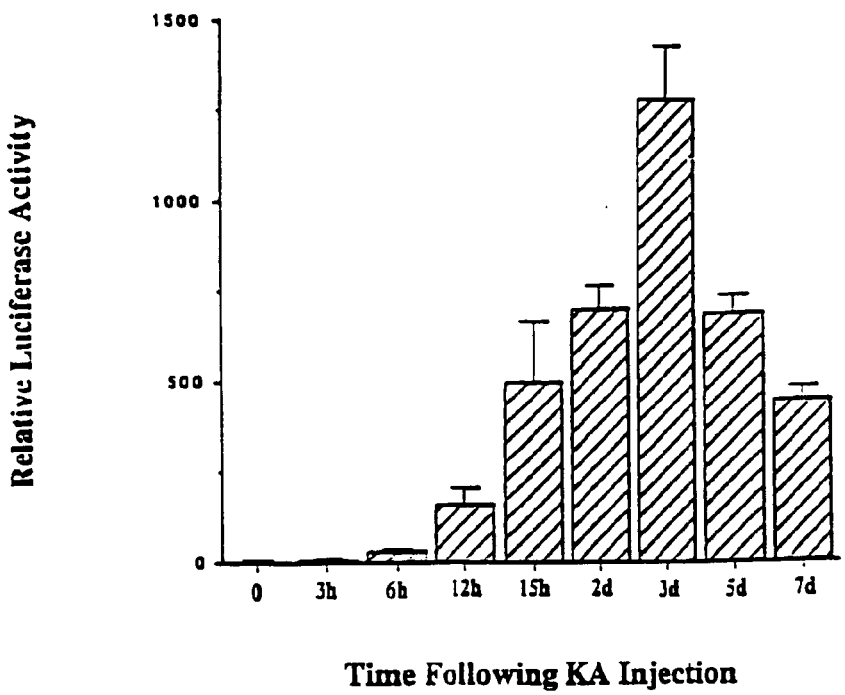
FIG. 11 is a bar graph showing the level of KA-induced AP-1 activity at various times after KA induction as reflected by luciferase activity in JNK3(−/−) mice crossed with transgenic AP-1 luciferase mice.

In the luciferase assay, mice were sacrificed at intervals after injection of KA (30 mg/kg, i.p.), and relative luciferase activity compared with that detected in hippocampal lysates obtained from mice injected with vehicle (saline). Mice were decapitated, brains were dissected, and brain tissues were immediately lysed in buffer containing 25 mM Hepes pH 7.4, 1% TRITON®X-100, 1 mM EDTA, 1 mM phenylmethyl sulfonyl fluoride, and 10 μg/ml leupeptin (Promega, Madison, Wis.). Luciferase activity was measured as described in Rincon and Flavell (Embo. J. 13:4370–4381, 1994). The injection of KA (30 mg/kg, i.p.) caused a large induction of AP-1 transcriptional activity in the hippocampus of wild-type mice, as evidenced by the induction of luciferase activity. Luciferase activity in wild type mice was detectable by six hours, gradually increased to the peak at three days, and persisted for at least seven days (FIG. 11). Control experiments demonstrated that the injection of vehicle (saline) did not cause induction of luciferase activity in the AP1-luc mice.

Figure 12:
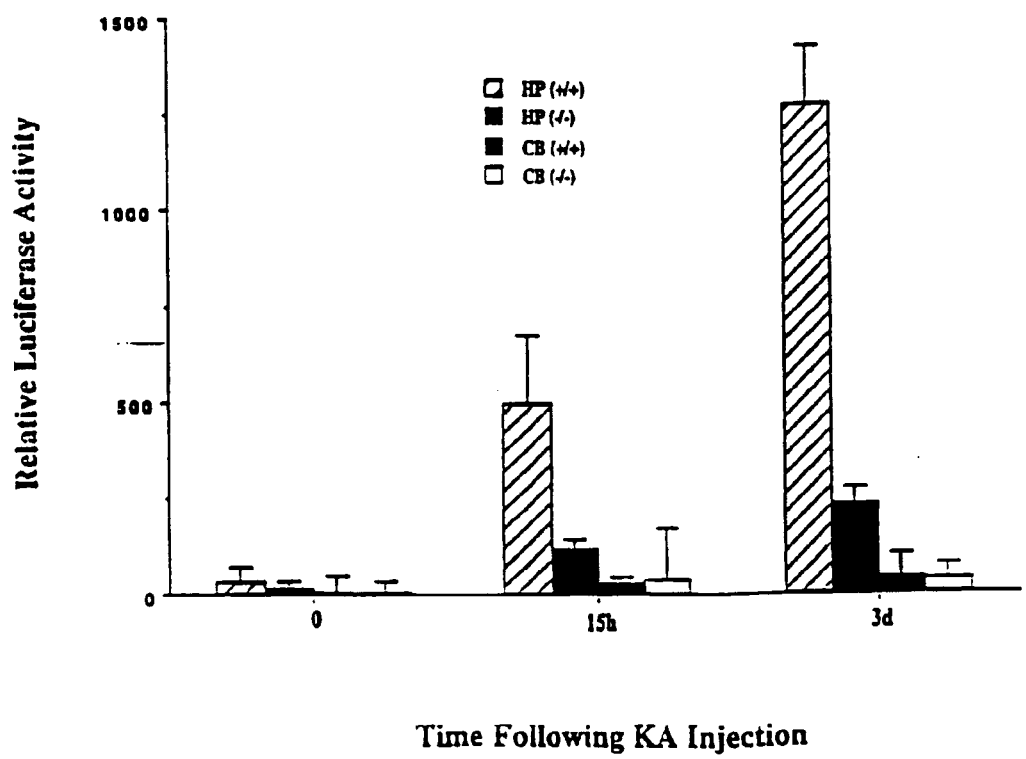
FIG. 12 is a bar graph showing the level of KA-induced AP-1 activity as reflected by the relative level of luciferase activity in hippocampus (HP) and cerebellum (CB) of JNK3 (−/−) mice and wild type(+/+) mice.

The relative luciferase activity in the hippocampus and cerebellum prepared from wild-type (+/+) and JNK3 (−/−) mice was measured following KA injection. The results are shown in FIG. 12. Each time point represents the mean of three to five (+SEM) individual animals. The induction of luciferase activity was most prominent in the hippocampus, where a markedly greater induction of phosphorylation of c-Jun was observed, as compared to the cerebellum and the cerebral cortex. The induction of AP-1 activity was significantly reduced in the JNK3 (−/−) mice with the AP1-luc transgene as compared to the wild type mice. At 15 hours after injection of KA, there was approximately four-fold greater AP-1 activity in the hippocampus of wild-type mice compared with JNK3(−/−) mice. At three days after injection, the AP-1 activity was more than six times higher in the hippocampus of wild-type compared with JNK3(−/−) mice. Together, these data demonstrate that the disruption of the JNK3 gene suppressed KA-induced phosphorylation of c-Jun and AP-1 transcription activity in the hippocampus in vivo.

Example 7

Resistance to KA-induced Apoptosis

One unique feature of KA among other epileptogenic agents is its potency in inducing neuronal cell death (Ben-Ari, supra; Schwob et al., supra). Since this property of cell destruction is paralleled by a sustained level of AP-1 transcriptional activity, it has been suggested that AP-1 mediates KA-induced-neuronal death (Kasof et al., supra; Schwarzschild et al., J. of Neurosci. 17:3455–3466, 1997). Wild-type and JNK3(−/−) mouse brains were therefore examined after treatment with KA to determine whether the attenuation of AP-1 transcriptional activity in JNK3 (−/−) mice altered the extent of neuronal damage (Ben-Ari, supra; Ben-Ari et al., supra; Schwob et al., Neurosci. 5:991–1014, 1980).

These experiments were performed as follows. Wild-type and JNK3 (−/−) mice were killed and fixed by transcardial perfusion of 4% paraformaldehyde and 1.5% glutaraldehyde three days after the injection of KA (30 mg/kg, i.p.). Semi-thin and thin sections of brain were prepared using a Vibratome and embedded in Epon. Tissue blocks were prepared using a microtome with a diamond tube for 1 μm-thick semithin sections examined by toluidine blue staining, and for ultrathin sections examined by electron microscopy. Nissl's stain was used for initial examination of damage to the hippocampus (Kluver et al., J. Neuropath. Exp. Neuro. 12:400–403, 1953). GFAP immunocytochemistry was also used to assess cell destruction in the hippocampus (Hsu et al., supra). Nissl's staining was also performed as described above. TUNEL assays, used to evaluate apoptosis, were performed using cryostat sections (50 μm) of cerebral hemispheres that were cryoprotected with sucrose. The TUNEL assay was modified from the terminal deoxynucleotidyl transferase (TdT)-mediated dUTP nick end labeling assay (Gavrieli et al., J. Cell. Biol. 119:493–501, 1992). Briefly, tissue sections, directly mounted on a salinated slide, were permeablized with 2% TRITON® X-100 (20 minutes at room temperature) and then incubated for nick end-labeling for 2 hours at 37° C. using 0.32 U/μl TdT (Boehringer Mannheim, cat# 220582) and 2 μM digoxigenin-11-dUTP (Boehringer Mannheim, cat# 1573152) in a final volume of 40 μl. The tissues were incubated with anti-digoxigenin antibody (Boehringer Mannheim, cat# 1333062) diluted 500-fold, and processed for immunocytochemistry using standard procedures (Hsu et al., supra).

The damage to the hippocampus caused by KA was initially examined by Nissl's stain. The KA-induced cell loss caused either a breach of staining of the pyramidal neurons in the CA3 region or a diffuse sparse staining throughout the CA1 subfield. To corroborate the cell destruction revealed by Nissl's stain, the TUNEL method was applied to detect apoptosis. Groups of small pyknotic nuclei and positively TUNEL-labeled cells were found in the hippocampal CA3 subfield devoid of Nissl's staining. Similarly, a high percentage of pyramidal neurons showing pyknotic nuclei and shattered apical dendrites and numerous strongly TUNEL-labeled cells were located in the hippocampal CA1 subfield which exhibited decreased Nissl's staining. Since the TUNEL method and the pyknosis morphology only indicated the extent of cell damage at one time point of a dynamic process, immunostaining of damage-induced GFAP was also used as an independent assessment of the extent of cell destruction in the hippocampus. Consistent with the patterns of Nissl's, toluidine, and TUNEL staining, an increased number of strongly GFAP-labeled astrocytes was found either in the hippocampal CA3 or CAl regions. Thus, a combination of Nissl's stain, GFAP immunocytochemistry, TUNEL method, and toluidine stain of semithin sections was used to classify the KA-induced damage in the mouse hippocampus.

A total of 17 wild-type and 18 JNK3(−/−) mice were examined. Results are shown in Table 1 (below). The table was compiled from two sets of data. First, wild-type (n=11) and JNK3 (−/−) (n=10) mice were sacrificed on the fifth day after a single injection of KA (30 mg/kg, i.p.). Second, wild-type (n=6) and JNK3 (−/−) (n=8) mice received an injection of KA (30 mg/kg, i. p.) for five consecutive days and examined two days following the final injection. The severity of the hippocampal damage in wild-type mice was comparable in experiments using both protocols. The ratio of no cell loss/CA3 lesion/CA3+CA1 lesion was 2/7/2 in the single-injection experiments, and 2/2/2 in the multiple injection experiments.

TABLE 1

Kainate-induced neuronal damage (number of animals)

| JNK3 genotype | +/+ | −/− |
| --- | --- | --- |
| No perceivable cell loss⸗ | 4 | 18 |
| Selective CA3 cell loss | 9 | 0 |
| Including CA1 cell loss | 4 | 0 |

The hippocampal CA3 region was the most susceptible to KA-induced damage in the wild-type mice (9/17; 53%). Cell loss was indicated by decreased crystal violet staining in the CA3 region. Using the TUNEL method (Gavrieli et al., supra), which identifies DNA fragmentation in the dying cells, groups of labeled cells were found in the damaged region. A cluster of pyknotic nuclei was found in the CA3 region in toluidine-stained semithin sections. As a result of KA-induced damage, there was selective glial proliferation confined to the CA3 region, as indicated by the strong immunostaining of GFAP. In some wild-type animals, massive cell loss was observed throughout the entire hippocampal CA1 region (4/17; 24%). Similarly, damage to the CA1 region was revealed by decreased crystal violet staining, positively TUNEL-labeled cells, pyknotic nuclei, shattered apical dendrites of pyramidal neurons, and both hypertrophy and proliferation of GFAP-positive astrocytes.

In contrast, there was no apparent hippocampal damage in any of the JNK3(-/-) mice examined (n=18). The pattern of the Nissl's stain, TUNEL assay, toluidine blue staining of semithin sections, and GFAP immunostaining of the hippocampal region in the JNK3(-/-) mice was indistinguishable from that of untreated wild-type mice. Moreover, although JNK2(-/-) mice developed seizures of comparable severity at the sublethal dose of 45 mg/kg KA (a dose that is lethal for more than 60% of wild-type mice due to continuous convulsions), cell damage was nevertheless found in a much smaller percentage of animals (2/15, 13%; p<0.005 by chi-square analysis, d.f.=1).

Methods of assessing apoptosis (e.g., TUNEL assay) can be used to evaluate whether JNK3 modulator is affecting apoptosis.

Example 8

Electron Microscopic Analysis of Ultrastructural Changes Associated with KA-Induced Neuronal Damage Cortical neurons in vitro undergo either apoptosis or necrosis depending on the extracellular concentration of the glutamate analog N-methyl-D-aspartate (NMDA) (Bonfoco et al., Proc. Natl. Acad. Sci. USA 92:7162–7166, 1995). The distinction between apoptosis versus necrosis in KA-induced neuronal damage is critical since necrosis is generally thought to represent a consequence of acute mechanical insult that is incompatible with an active cell death program involving de novo protein synthesis. The TUNEL results (supra) indicate the involvement of apoptosis. To further examine whether the neuronal death in vivo due to KA induction was apoptotic or necrotic, electron microscopy was employed to investigate the ultrastructural changes in the degenerated hippocampal neurons. The microscopic analysis suggested a series of morphological changes indicating neuronal damage in the wild-type mouse as a consequence of apoptosis. The initial event after KA injection (30 mg/kg i.p.) appeared to be compaction and segregation of chromatin in pyramidal neurons into electron-dense masses that abutted on the inner surface of the nuclear envelope. In contrast, the nuclei of the hippocampal neurons in the JNK3(-/-) mice following KA injection contained homogeneous electron-lucent euchromatin. At later stages, in wild type mice, there was convolution of the nuclear outline and condensation of the cytoplasm. The double-layered structure of the nuclear envelope in wild type mice remained largely intact in all of these morphological stages. Eventually the degenerated neurons disintegrated resulting in numerous membrane-bounded apoptotic bodies. These morphological features are all consistent with the hallmarks of apoptosis (Kerr et al., Br. J. Cancer 26:239–257, 1972). Thus, it appeared that KA triggered a genetic program within the damaged neuron leading to apoptosis, which was abrogated in JNK3-deficient neurons.

Figure 13:
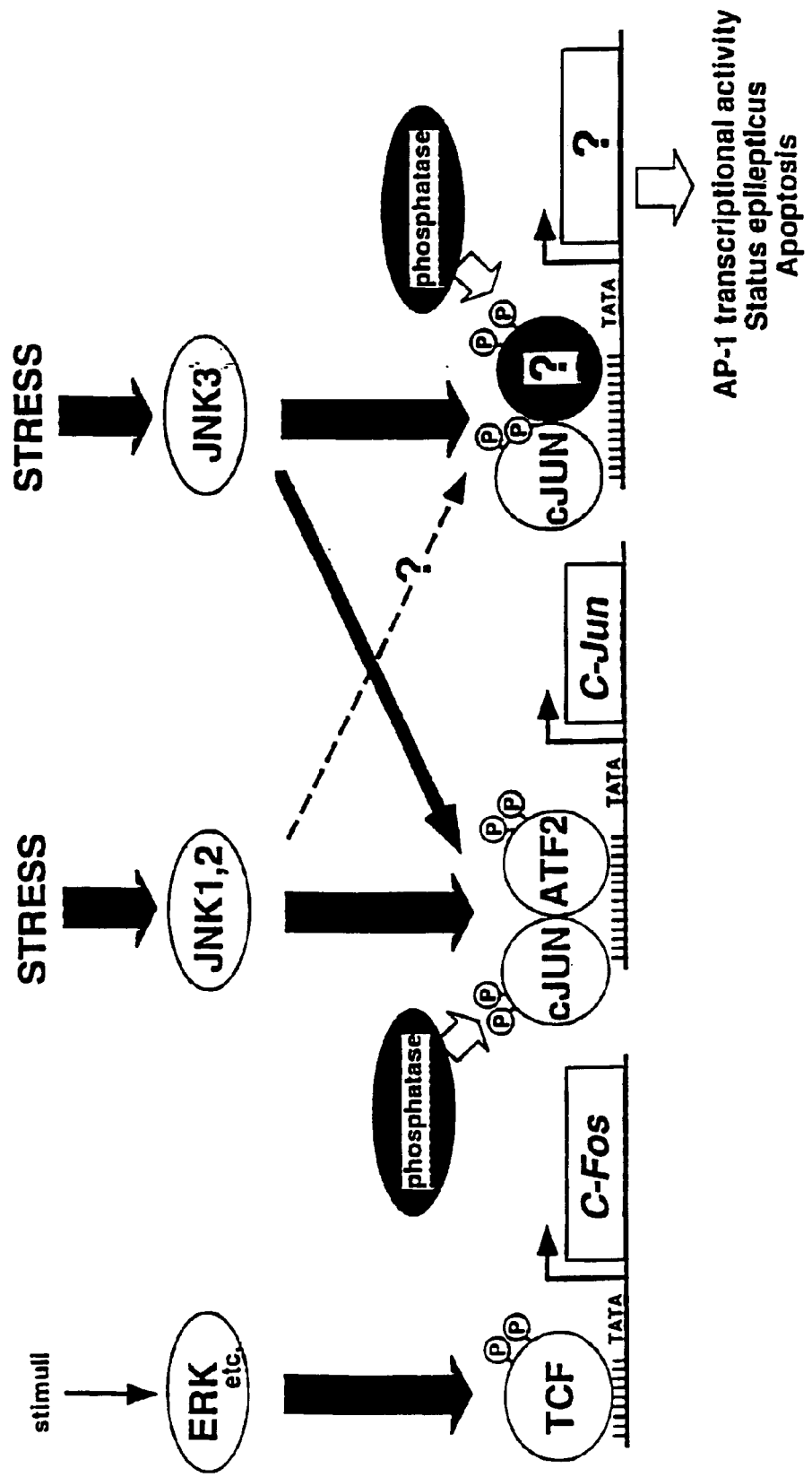
FIG. 13 is a diagram of the proposed chain of molecular events caused by KA leading to neuronal apoptosis.

These results suggest that KA-induced phosphorylation of the $NH_2$-terminal activation domain of c-Jun leads to increased AP-1 transcriptional activity and neuronal apoptosis. Without limitation to a particular theory, a proposed chain of molecular events caused by KA that lead to neuronal apoptosis is shown in FIG. 13.

Figure 14:
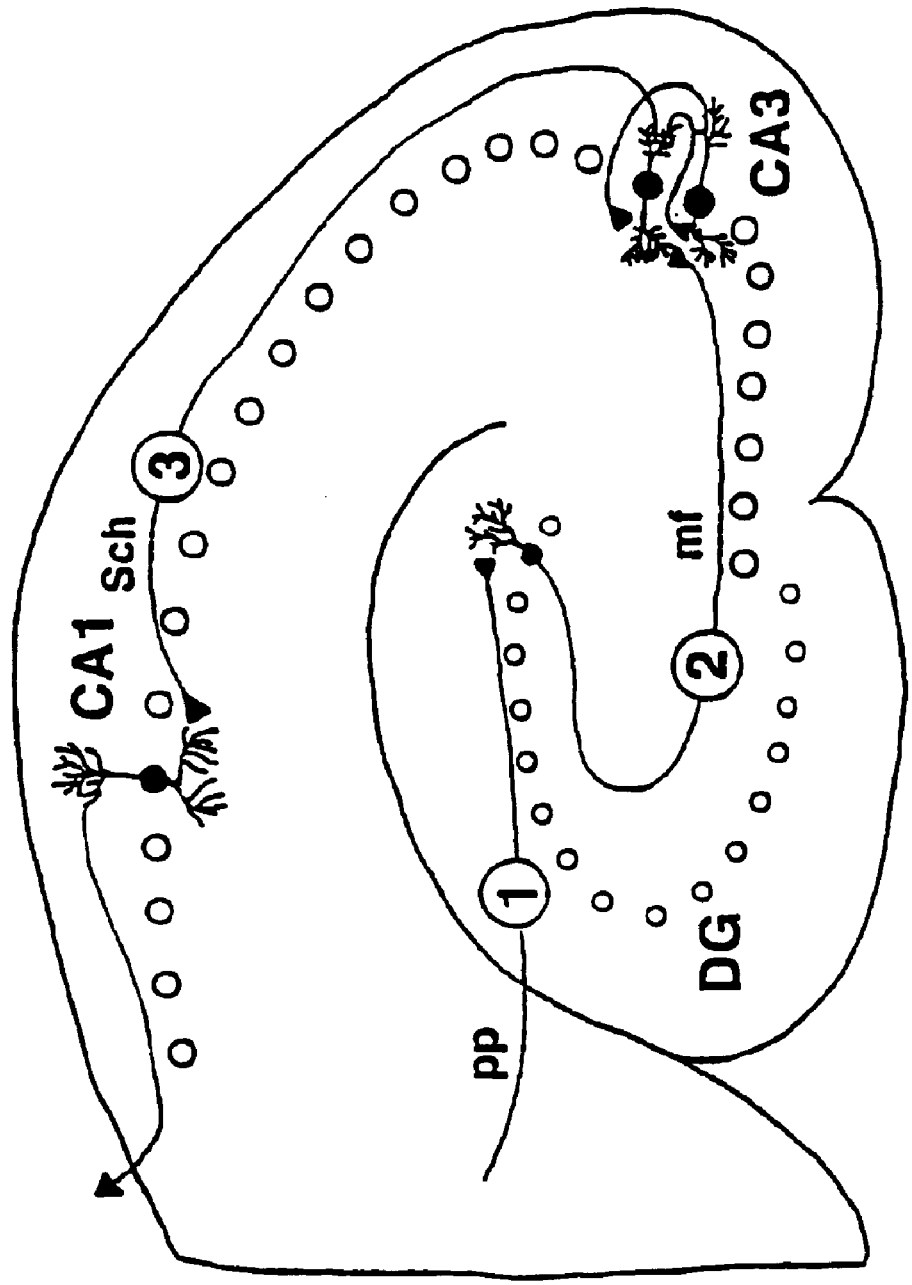
FIG. 14 is a diagram of the trisynaptic connection within the hippocampal formation.

Although systemic administration of KA causes cell damage predominantly localized in the hippocampal CA3 area, the significance of JNK3 in stress-induced neuronal apoptosis is not only restricted to this region. Several lines of evidence indicate that the particular vulnerability of the CA3 hippocampal neurons to KA is due to their unique cellular and synaptic properties. First, the hippocampal CA3 and CA4 regions have the highest density of KA-receptors (Berger et al., Neurosci. Lett. 39:237–242, 1983). Second, the recurrent synaptic excitation is particularly potent in the hippocampal CA3 region (Miles et al., J. Physiol. (London) 373:397–418, 1986). The recurrent excitation of the CA3 pyramidal neurons may sustain JNK3 signaling and therefore rapidly induce KA excitotoxicity. The observed progression of c-Jun phosphorylation from the dentate gyrus to the CA3 region is reminiscent of the synaptic circuitry of the hippocampus. A diagram of the trisynaptic connection within the hippocampal formation is shown in FIG. 14. The first synaptic relay (1) is from the afferent perforant path (pp) onto the granule cell of the dentate gyrus (DG). The second relay (2) follows the mossy fiber (mf) from the dentate gyrus to the CA3 hippocampal neurons. The third relay (3) is from the hippocampal CA3 to the CA1 region along the Schaffer collaterals (Sch). There are recurrent synaptic interactions of pyramidal neurons in the CA3 region.

Example 9

Assays for Detection of Inhibitors of JNK3 Protein Kinase Activity

Inhibitors of JNK3 can be identified in protein kinase assays. These assays can be performed using JNK3 purified from tissue (e.g., brain) or with recombinant enzyme. The recombinant JNK3 can be isolated from bacteria, yeast, insect, or mammalian cells using standard procedures. Assays of endogenous (natural) JNK3 are known in the art and assays of recombinant JNK3 have been described previously (Gupta et al., EMBO J. 15:2760–2770, 1996).

The protein kinase activity of JNK3 can be measured using ATP and protein substrates for JNK3 in an in vitro assay. These substrates include, but are not limited to, the transcription factors ATF2 and Elk-1 (Gupta et al., 1996, supra). The incorporation of phosphate into the substrate can be measured by several methods. One example is to measure the incorporation of radioactive phosphate (e.g., $^{32}P$) into the substrate. The incorporation into the substrate can be measured following removal of unincorporated radioactivity by precipitation with trichloroacetic acid and recovery on phosphocellulose paper or by polyacrylamide gel electrophoresis. The radioactivity can be monitored by scintillation counting, phosphorimager analysis, or by autoradiography. In general, methods for automated high throughput screens would not use radioactive materials. For this purpose a method is used to detect the phosphorylated substrate without a radioactive probe. In one approach the electrophoretic mobility of the substrate is examined. For example, ATF2 demonstrates a marked reduction in electrophoretic mobility following phosphorylation by JNK on Thr-69 and Thr-71 (Gupta et al., Science 267:389–393, 1995).

A second approach is to detect the phosphorylation of the substrate using immunochemical methods (e.g. ELISA). Antibodies that bind specifically to the phosphorylated substrates are prepared (monoclonal and polyclonal) and are commercially available (e.g., New England Biolabs, Promega Corp., and Upstate Biotechnology Inc.). The extent of substrate phosphorylation is then measured by standard ELISA assay using secondary antibodies coupled molecules suitable for to spectrophotometric or fluorometric detection using methods known in the art.

Molecules that inhibit JNK3 can be identified in a high throughput screen. A molecule that is a preferred candidate to treat excitotoxic disorders inhibits JNK3, but not other protein kinases, including related MAP kinases. Candidate molecules once identified can be optimized using combinatorial chemical methods or by the synthesis of related molecules. These molecules represent candidate drugs that can be tested for JNK3 therapy.

Example 10

Assays for Detection of Inhibitors of JNK3 Activation

The JNK protein kinases are activated by dual phosphorylation on Thr and Tyr within protein kinase sub-domain VIII (Davis, Trends Biochem. Sci. 19:470–473, 1994). These sites of activating phosphorylation are conserved in JNK3 (Gupta et al., 1996, supra). Molecules that inhibit the activation of JNK3 by interfering with the phosphorylation of JNK3 can be identified by measurement of JNK3 activation in the presence and absence of candidate molecules. Cells expressing JNK3, e.g., neuronal cells, neuroendocrine cells, or cells that are engineered to express recombinant JNK3 (Gupta et al., 1996 supra), are exposed to environmental stress (e.g., depolarization, excitotoxic agents, UV radiation, heat, and anoxia) to activate JNK3. The state of JNK3 activation can be assessed by several methods. For example, JNK3 can be isolated, washed free of the candidate inhibitor, and the activation state of JNK3 monitored by protein kinase assay (supra). Alternatively, the activation of JNK3 can be probed using immunological methods using antibodies that bind to the Thr and Tyr phosphorylated (activated) form of JNK3. Antibodies that bind specifically to the Thr and Tyr phosphorylated enzyme can be prepared (monoclonal and polyclonal) and are commercially available (e.g., from New England Biolabs and Promega Corp.). The extent of substrate phosphorylation can then be measured by a standard ELISA assay using secondary antibodies coupled to spectrophotometric or fluorometric detection.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that modulates excitotoxicity, the method comprising
   incubating a cell that can exhibit excitotoxicity with a compound that modulates JNK3 expression under conditions and for a time sufficient for the cell to exhibit excitotoxicity in the absence of the compound; and
   (b) measuring a level of excitotoxicity in the cell after incubating step (a);
   wherein a difference in the level of excitotoxicity measured in step (b) compared to the level of excitotoxicity in the absence of the compound indicates that the compound modulates excitotoxicity.

2. A method of identifying a compound that modulates excitotoxicity, the method comprising
   (a) incubating a cell that can exhibit excitotoxicity with a compound that modulates JNK3 activity under conditions and for a time sufficient for the cell to exhibit excitotoxicity in the absence of the compound; and (b) measuring a level of excitotoxicity in the cell after incubating step (a), wherein a difference in the level of excitotoxicity measured in step (b) compared to the level of excitotoxicity in the absence of the compound indicates that the compound modulates excitotoxicity.

3. A method of identifying a compound that modulates excitotoxicity, the method comprising (a) administering a compound that modulates JNK3 expression to an animal model of an excitotoxic disorder; and (b) measuring a level of excitotoxicity in the animal, wherein a difference in the level of excitotoxicity measured in step (b) compared to the level of excitotoxicity in the absence of the compound indicates that the compound modulates excitotoxicity.

4. A method of identifying a compound that modulates excitotoxicity, the method comprising:

(a) administering a compound that modulates JNK3 activity to an animal model of an excitotoxic disorder; and (b) measuring a level of excitotoxicity in the animal, wherein a difference in the level of excitotoxicity measured in step (b) compared to the level of excitotoxicity in the absence of the compound indicates that the compound modulates excitotoxicity.

5. The method of claim 1 or 2, wherein the method further comprises (i) incubating a control cell that can exhibit excitotoxicity in the absence of the compound under conditions and for a time sufficient for the cell to exhibit excitotoxicity;

(ii) measuring excitotoxicity in the cell after said incubating step (i); and (iii) comparing the level of excitotoxicity measured in step (b) with the level of excitotoxicity measured in step (ii).

6. A method of claim 1, 2, 3, or 4, wherein the compound decreases excitotoxicity.

7. The method according to claim 1, 2, 3, or 4, wherein the compound is a soluble peptide.

8. The method according claim 1, 2, 3, or 4, wherein the compound is a phosphopeptide.

9. The method according to claim 1, 2, 3, or 4, wherein the compound is a peptidomimetic.

10. The method according to claim 1, 2, 3, or 4, wherein the compound is a small organic molecule.

11. The method according to claim 1, 2, 3, or 4, wherein the compound is an inorganic molecule.

12. The method of claim 1 or 3, wherein the compound reduces JNK3 expression.

13. The method of claim 2 or 4, wherein the compound reduces JNK3 activity.

14. The method of claim 2 or 4, wherein the JNK3 activity is JNK3 substrate binding.

* * * * *